(12) United States Patent
Nam et al.

(10) Patent No.: US 12,024,546 B2
(45) Date of Patent: Jul. 2, 2024

(54) PEPTIDES AND ANTI-CANCER COMPOSITIONS INCLUDING THEREOF

(71) Applicant: GWANGJU INSTITUTE OF SCIENCE AND TECHNOLOGY, Gwangju (KR)

(72) Inventors: Jeong Seok Nam, Gwangju (KR); So Yeon Park, Gwangju (KR); Tae Young Jang, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 18/070,125

(22) Filed: Nov. 28, 2022

(65) Prior Publication Data

US 2023/0357362 A1 Nov. 9, 2023

(30) Foreign Application Priority Data

May 6, 2022 (KR) .................. 10-2022-0055955
Jul. 5, 2022 (KR) .................. 10-2022-0082526

(51) Int. Cl.
*C07K 14/00* (2006.01)
*A61P 35/00* (2006.01)
*C07K 14/78* (2006.01)

(52) U.S. Cl.
CPC .............. *C07K 14/78* (2013.01); *A61P 35/00* (2018.01)

(58) Field of Classification Search
CPC .................. C07K 14/78; A61P 35/00
See application file for complete search history.

(56) References Cited

U.S. PATENT DOCUMENTS

2010/0154071 A1* 6/2010 Fanidi .............. G01N 33/57415
424/139.1

OTHER PUBLICATIONS

National Institute of Cancer—understanding and related topics, accessed Aug. 18, 2019 at URL: https://www.cancer.gov/about-cancer/understanding/what-is-cancer.*
Enablement Decision Tree, Example F, situation 1.*
Nam JS, Hirohashi S, Wakefield LM. Dysadherin: a new player in cancer progression. Cancer Lett. Oct. 8, 2007;255(2):161-9. doi: 10.1016/j.canlet.2007.02.018. Epub Apr. 17, 2007.*
Yoshinori Ino et al., "Dysadherin, a cancer-associated cell membrane glycoprotein, down-regulates E-cadherin and promotes metastasis.", Proc Natl Acad Sci, Jan. 8, 2002, vol. 99, No. 1, pp. 365-370.
Jeong-Seok Nam et al., "Dysadherin: a new player in cancer progression.", Cancer Lett., Oct. 8, 2007, 255(2), pp. 161-169.

* cited by examiner

*Primary Examiner* — Jeanette M Lieb
(74) *Attorney, Agent, or Firm* — The PL Law Group, PLLC

(57) ABSTRACT

A peptide according to an embodiment may be used as an anti-cancer agent. The peptide has a binding activity to fibronectin and competitively binds to fibronectin with dysadherin. Therefore, the peptide may be used to prevent binding between dysadherin in a cell membrane of cancer cells and fibronectin in ECM, and may be used as an anti-cancer agent to weaken survival, migration or invasion of cancer cells.

6 Claims, 74 Drawing Sheets

Specification includes a Sequence Listing.

FIG. 1C

WT   gRNA #1
GGCTGCAAAGGCTGCTAGGCATCTCGGGGCGGG.....(5kb).....
(SEQ ID NO:111)

gRNA #2                                              gRNA #3
...TTGTTCCTGGGCTCGGTCACGTGGTAGTGCCCCGATGAGCGGATACAGAGACACAGGA
(SEQ ID NO:112)

Strain 661: null allele 5740 bp deletion
GGCTGCAAAGGCTGCTAGGCATCTC................................TGAGCGGATACAGAGACACAGGA
(SEQ ID NO:113)                                         (SEQ ID NO:114)

Strain 662: null allele 5751 bp deletion
GGCTGC................................CCCCGATGAGCGGATACAGAGACACAGGA
                                       (SEQ ID NO:115)

| Birth rate | | | |
|---|---|---|---|
| $Fxyd5^{+/-}$ x $Fxyd5^{+/-}$ | | | |
| | Observed | | Expected |
| | No. of mice | % | % |
| $Fxyd5^{+/+}$ | 11 | 22.45 | 25 |
| $Fxyd5^{+/-}$ | 25 | 51.02 | 50 |
| $Fxyd5^{-/-}$ | 13 | 26.53 | 25 |
| p-value = 0.913 | | | | n=49 mice from 7 litters

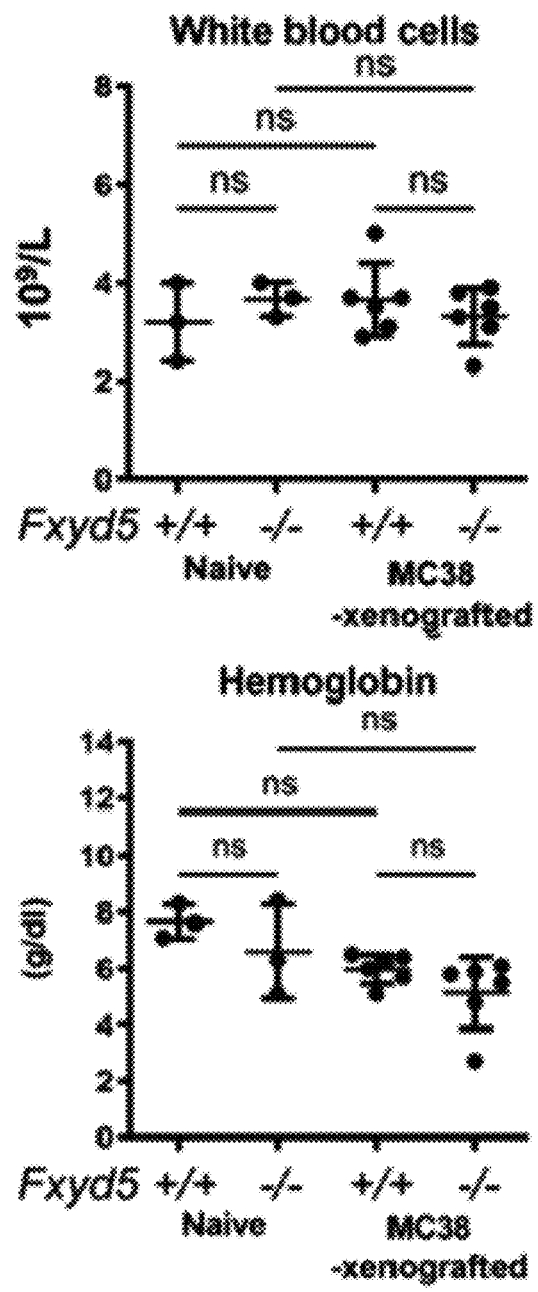

Multivariate Cox analysis (Dysadherin low vs high)
RFS ( II + III ): HR 2.569 (95% CI, 1.046-6.308),
p=0.040

Multivariate Cox analysis (Dysadherin low vs high)
OS ( II + III ): HR 3.863 (95% CI, 1.698-8.792), p=0.002

Signaling networks affected by Dys KO

FIG. 13A

Extracellular domain of Dysadherin

AA 22 — AA 145

N#01: AA 22-42
N#02: AA 33-52
N#03: AA 43-63
N#04: AA 54-74
N#05: AA 64-84
N#06: AA 75-94
N#07: AA 85-105
N#08: AA 96-115
N#09: AA 106-125
N#10: AA 116-135
N#11: AA 126-145

N#01: HHHHHH-QTLKDTTSSSSADSTIMDIQV (SEQ ID NO: 100)
N#02: HHHHHH-ADSTIMDIQVPTRAPDAVYT (SEQ ID NO: 101)
N#03: HHHHHH-PTRAPDAVYTELQPTSPTPTM (SEQ ID NO: 102)
N#04: HHHHHH-LQPTSPTPMPADETPQPQT (SEQ ID NO: 103)
N#05: HHHHHH-PADETPQPQTQQLEGTDGP (SEQ ID NO: 104)
N#06: HHHHHH-TQQLEGTDGPLVTDPETHKS (SEQ ID NO: 105)
N#07: HHHHHH-LVTDPETHKSKAAHPTDDTT (SEQ ID NO: 106)
N#08: HHHHHH-KAAHPTDDTTTLSERPSPST (SEQ ID NO: 107)
N#09: HHHHHH-TLSERPSPSTDVQTDPQTLK (SEQ ID NO: 108)
N#10: HHHHHH-DVQTDPQTLKPSGFHEDDPF (SEQ ID NO: 109)
N#11: HHHHHH-PSGFHEDDPFFYDEHTLRKR (SEQ ID NO: 110)

*HHHHHH: 6XHis (His-tagged)
*Ni: Nickel-NTA (His-binding resin)
*FN: Fibronectin

E

Endogenous FAK activation

Scale bar: 10 μm

PEPTIDES AND ANTI-CANCER COMPOSITIONS INCLUDING THEREOF

CROSS-REFERENCE TO RELATED APPLICATION AND CLAIM OF PRIORITY

This application claims the benefit under 35 USC § 119 of Korean Patent Application Nos. 10-2022-0055955, filed on May 6, 2022 and 10-2022-0082526, filed on Jul. 5, 2022, in the Korea Intellectual Property Office, the entire disclosure of which is incorporated herein by reference for all purposes.

BACKGROUND

1. Field

The present invention relates to a novel peptide and an anti-cancer composition including the same, which may be used in the medical field for prevention or treatment of cancer.

2. Background Description

Dysadherin is a cancer-associated antigen and cell membrane glycoprotein with an FXYD motif. While dysadherin is overexpressed in a broad range of human cancers, including thyroid, esophageal, gastric, colorectal, pancreatic, cervical, testicular, breast, and head and neck tumors, dysadherin surface expression is limited in normal cells, and dysadherin is rarely expressed on non-neoplastic cells. Dysadherin has been identified as a strong inducer of cancer invasion and metastasis. According to clinical studies, it has indicated that high dysadherin expression in tumor tissues is significantly correlated with clinicopathological variables such as distant metastasis, recurrence, and low survival rate. However, dysadherin-associated molecular mechanism remains ambiguous, and particularly, the potential physiological relevance of dysadherin to tumorigenesis has not yet been determined.

Extracellular matrix (ECM) molecules trigger a variety of critical signaling cues and play a key role in the regulation of cellular phenotype and behavior. During tumor development, reciprocal interaction between ECM and cancer cells constantly occurs and leads to changes in cell structure, adhesion properties, and response to signals from ECM proteins. Some of these changes in cellular phenotype are accomplished by the cells' availability to sense mechanical forces, which are then converted into biochemical signals within the cell, thereby leading to a number of cellular mechanisms being activated, including cell adhesion, proliferation, survival, and migration.

The inventors of the present invention conducted comprehensive bioinformatics analyses to discover novel therapeutic agents for treatment of cancer, and found an association between dysadherin and ECM-cell signaling. The present inventors developed an effective peptide for cancer treatment by analyzing dysadherin-interacting ECM proteins and downstream signaling pathways, and therefore, the present invention has been completed on the basis of the above finding.

SUMMARY

A purpose of the present invention is to provide a peptide and a composition including the same, which are effective for prevention and treatment of cancer.

To achieve the above goals, the following technical solutions are adopted in the present invention.

1. A peptide including at least a portion of a sequence of SEQ ID NO: 1, wherein the portion has a length of 5aa or more.
2. The peptide according to the above 1, wherein the portion has a length of 10aa or more.
3. The peptide according to the above 1, which the peptide consists of any one of SEQ ID NOs: 2 to 7.
4. A pharmaceutical composition for prevention or treatment of cancer including at least a portion of a sequence of SEQ ID NO: 1, wherein the portion includes a peptide having a length of 5aa or more.
5. The pharmaceutical composition for prevention or treatment of cancer according to the above 4, wherein the portion has a length of 10aa or more.
6. The pharmaceutical composition for prevention or treatment of cancer according to the above 4, wherein the peptide includes a sequence selected from the group consisting of SEQ ID NOs: 2 to 7.
7. The pharmaceutical composition for prevention or treatment of cancer according to the above 4, wherein the peptide consists of sequences of SEQ ID NO: 2 or 5.
8. The pharmaceutical composition for prevention or treatment of cancer according to the above 4, wherein the cancer is colorectal cancer, breast cancer, colon cancer, small intestinal cancer, rectal cancer, ovarian cancer, cervical cancer, prostate cancer, testicular cancer, penile cancer, urothelial cancer, ureteral cancer, renal pelvic cancer, esophageal cancer, laryngeal cancer, gastric cancer, gastrointestinal cancer, skin cancer, keratoacanthoma, follicular carcinoma, melanoma, lung cancer, small cell lung carcinoma, non-small cell lung carcinoma (NSCLC), lung adenocarcinoma, squamous cell carcinoma of the lung, pancreatic cancer, thyroid cancer, papillary cancer, bladder cancer, liver cancer, bile duct cancer, bone cancer, hair cell cancer, oral cancer, lip cancer, tongue cancer, salivary gland cancer, pharyngeal cancer, kidney cancer, vulvar cancer, thyroid cancer, endometrial cancer, uterine cancer, brain cancer, central nervous system cancer, peritoneal cancer, hepatocellular carcinoma, Hodgkin disease or leukemia.
9. The pharmaceutical composition for prevention or treatment of cancer according to the above 4, wherein the cancer is colorectal cancer, liver cancer or breast cancer.

The peptide and pharmaceutical composition for prevention or treatment of cancer according to the present invention may effectively inhibit binding between dysadherin in a cell membrane of cancer cells and fibronectin of an extracellular matrix.

The peptide and pharmaceutical composition for prevention or treatment of cancer have excellent anti-cancer effects according to the present invention.

BRIEF DESCRIPTION OF THE DRAWINGS

FIGS. 1A-1G illustrate the genetic ratio of pups born in Fxyd5$^{+/-}$ mice and analysis of intestines of wild-type and Fxyd5$^{-/-}$ mice. (FIG. 1A) Schematic view showing the targeting of exons 2-7 of the Fxyd5 gene using 3 guide RNAs (gRNAs). Arrows indicate the 5'- and 3'-primer pairs used for genotyping. (FIG. 1B) Detection of the Fxyd5-deleted chromosome by PCR. Among the six pups from zygote injection, four showed deletion bands. Asterisks indicate pups harboring deleted alleles. (FIG. 1C) Sequencing analysis of strains 661 and 662. Strains 661 and 662 carried 5740-bp and 5751-bp deletions between the gRNA #1- and gRNA #3-targeted regions. Because the deleted region contained the first ATG sequence at exon 2 and most of the coding region, chromosomes harboring deletions in strains 661 and 662 were null. (FIG. 1D) Generation of Fxyd5-KO founder from strain 661. At least 5 successive breedings with C57BL/6J mice were conducted for the experiments. (FIG. 1E) The pups born from Fxyd5$^{+/-}$ litters followed the Mendelian ratio. Statistical values were estimated by the chi-square test. (FIGS. 1F,1G) H&E-stained images of wild-type or Fxyd5$^{-/-}$ mouse intestines. The lengths of crypts and villi were measured in mice with the indicated genotype (n=7/group). Data indicate the means±SEMs. Statistical comparisons of the two groups were carried out by Student's t-test. Ns indicates no significance.

(FIG. 2A) IF showing the acquisition of dysadherin expression in the intestinal tumor epithelium (EpCAM+) of Apc$^{Min/+}$;Fxyd5$^{+/+}$ mice and complete elimination of dysadherin expression in the intestinal tumor epithelium of Apc$^{Min/+}$;Fxyd5$^{-/-}$ mice. (FIG. 2B) Tumor incidence in Apc$^{Min/+}$;Fxyd5$^{+/+}$ and Apc$^{Min/+}$;Fxyd5$^{-/-}$ mice at the indicated ages (# of tumor-bearing mice/# of examined mice). (FIG. 2C) Number of intestinal tumors and total tumor load per mouse (Apc$^{Min/+}$;Fxyd5$^{+/+}$, n=12; Apc$^{Min/+}$; Fxyd5$^{-/-}$, n=20). (FIG. 2D) Left: schematic view of AOM/DSS-induced intestinal tumorigenesis model. Right: number of colonic tumors and total tumor load in 22-week-old AOM/DSS mice (Fxyd5$^{+/+}$, n=7;Fxyd5$^{-/-}$, n=7). (FIG. 2E) Representative images showing intestinal tumoroids derived from Apc$^{Min/+}$ mice subjected to knockdown of Fxyd5. (FIG. 2F) Effects of dysadherin knockdown on tumoroid viability and size (n=3/group). In all panels, data are reported as means±SEMs; *, , and * indicate p<0.05, <0.01, and <0.001, respectively; ns indicates no significance. Statistical comparisons between 2 groups were performed using Student's t-test or two-way ANOVA with the Bonferroni multiple comparison test.

(FIG. 3A) Number of intestinal tumors and total tumor load per mouse were quantified in 20-week-old Apc$^{Min/+}$ mice (Apc$^{Min/+}$;Fxyd5$^{+/+}$, n=12; Apc$^{Min/+}$;Fxyd5$^{+/-}$, n=14; Apc$^{Min/+}$;Fxyd5$^{-/-}$, n=20). (FIG. 3B) Representative images of immunohistochemical detection of Ki67 and cleaved-caspase 3 in the intestinal tumors of 20-week-old Apc$^{Min/+}$ mice. Nuclei were counterstained with hematoxylin. Graphs show the protein levels of Ki67 and cleaved-caspase3 in the intestinal tumors of 20-week-old Apc$^{Min/+}$ mice (Apc$^{Min/+}$;Fxyd5$^{+/+}$, n=8; Apc$^{Min/+}$; Fxyd5$^{-/-}$, n=8). (FIG. 3C) Representative images of hematoxylin and eosin stained intestinal tumor tissues from 20-week-old Apc$^{Min/+}$ mice. In control mice (ApC$^{Min/+}$; Fxyd5$^{+/+}$), tumor cells (arrowheads) invaded the muscularis mucosae (MM, dotted line) and muscularis propria (MP), reaching the serosa (Se). In dysadherin-deficient mice (Apc$^{Min/+}$;Fxyd5$^{-/-}$), tumor cells remained above the MM. (FIG. 3D) IF analysis of the intestines of 20-week-old Apc$^{Min/+}$ mice labeled for the epithelial marker EpCAM and α-smooth muscle actin (SMA). The stacked bar graph shows the percentage of invasive or noninvasive tumors among examined tumors per group. (FIG. 3E) The number of colonic tumors and total tumor load in 22-week-old AOM/DSS mice (Fxyd5$^{+/+}$, n=7;Fxyd5$^{+/-}$, n=7; Fxyd5$^{-/-}$, n=7). Mice were divided into 3 groups according to the diameter of the tumors in the intestines: small tumors, <3 mm; medium tumors, >3 mm and <5 mm; and large tumors, >5 mm. Tumor load was calculated according to the following formula: tumor load=(number of small tumors)×1+(number of medium tumors)×2+(number of large tumors)×3. In all panels, data indicate the means±SEMs; *, , and * indicate p<0.05, <0.01, and <0.001, respectively; ns indicates no significance. Statistical comparisons were performed using one-way ANOVA with Dunnett's multiple comparison tests for 3 or more groups. AOM: azoxymethane, DSS: dextran sulfate sodium. C-Caspase3: cleaved-Caspase 3, Dys: dysadherin, IOD: integrated optical density.

FIGS. 4A-4G illustrate effect of stromal depletion of dysadherin in a syngeneic mouse model. (FIG. 4A) Left: schematic view of syngeneic mouse model. Luciferase-labeled MC38 cells (C57BL/6 mice-derived colon carcinoma cell line) were inoculated s.c. into C57BL/6J mice (5×104/mouse). Middle and right: tumor growth was monitored by measuring luciferase activity until necropsy (Fxyd5$^{+/+}$, n=6;Fxyd5$^{-/-}$, n=6). (FIG. 4B) Tumor volumes were calculated according to the following formula: tumor volume=length×width2/2. (FIG. 4C) Left: Tumor weights were measured after necropsy. Right: representative images of MC38 tumors grown in Fxyd5$^{+/+}$ or Fyxd5$^{-/-}$ mice. (FIGS. 4D-4G) Immune cell and hematological parameters in naive control and MC38-inoculated mice with the indicated genotypes were compared. In all panels, data indicate the means±SEMs; *, , and * indicate p<0.05, <0.01, and <0.001, respectively; ns indicates no significance. Statistical comparisons between 2 groups were performed using Student's t-test or two-way ANOVA with the Bonferroni multiple comparison test, and for 3 or more groups using one-way ANOVA with Dunnett's multiple comparison tests.

(FIG. 5A) MC38 cells were transfected with scrambled siRNAs (siCTRL) and siRNAs targeting mouse Fxyd5 (siFxyd5). The Fxyd5 transcript level was determined by real-time RT-qPCR 96 h after transfection. Relative Fxyd5 levels were normalized to endogenous Hprt. (FIG. 5B) Intestinal tumoroids from Apc$^{Min/+}$ mice were dissociated into single cells, and siCTRL or siFxyd5 was transfected by electroporation (NEPA Gene, Chiba, Japan). The level of mRNA expression was determined 96 h after transfection. In all panels, data indicate the means±SEMs; *** indicates p<0.001. Statistical comparisons were performed using one-way ANOVA with Dunnett's multiple comparison tests for 3 or more groups.

(FIG. 6A) mRNA expression of dysadherin (FXYD5) was measured by real-time RT-qPCR in tumor tissues and matched adjacent normal tissues (total n=187, Stage I n=30, Stage II n=79, Stage III n=78). Statistical significance was determined by a paired Student's t-test. (FIG. 6B) Representative immunoblots showing dysadherin protein expression in tumor and matched normal adjacent tissues from 7 patients with CRC. (FIG. 6C) Representative imnunohistochemical staining of dysadherin in tumors and matched normal tissues from patients with CRC. (FIG. 6D) Graphs showing the integrated optical density (IOD) of dysadherin protein levels within the epithelium in the indicated group. Statistical significance was determined by a paired Student's t-test. (FIGS. 6E,6F) Kaplan-Meier survival analysis of patients with CRC. Patients were divided into four groups according to stage (stage II and III) and dysadherin expression (high and low). Statistical significance was determined by log-rank tests. (FIG. 6G) LDA was performed to compare the tumor-forming potential. Different numbers of SW480 cells with and without KO of dysadherin were inoculated s.c. into NOD.Cg-Prkdcscid/J mice (n=6/group). (FIG. 6H) Luciferase-labeled SW480 cells with and without KO of dysadherin were inoculated into the spleens of NOD.Cg-Prkdcscid/J mice (n=6/group). Metastatic tumor formation was observed via bioluminescence and necropsy. In all panels, data are reported as means t SEMs; *, , and * indicate p<0.05, <0.01, and <0.001, respectively. Statistical comparisons between 2 groups were performed using Student's t-test or two-way ANOVA with the Bonferroni multiple comparison test, or using one-way ANOVA with Dunnett's multiple comparison tests for 3 or more groups. EV: empty vector.

(FIG. 8A) Immunoblot analyses in a panel of human CRC cell lines. (FIG. 8B) Immunoblots confirming the establishment of dysadherin-KO and dysadherin-OE CRC cell lines. Numbers of viable cells at the indicated time points measured with an automated cell counter (n=5/group). (FIG. 8C) Survival potential measured by clonogenic assays (n=3/group). (FIG. 8D) Dysadherin-KO and dysadherin-OE cells were cultured in serum-free media for 72 h. Annexin V/PI staining and subsequent FACS analyses were performed to determine the population of apoptotic cells (n=3/group). (FIG. 8E) Boyden chamber assays without Matrigel matrix-coated membranes were performed to compare the chemotactic migration potential of dysadherin-KO or -OE cells (n=3/group). (FIG. 8F) Boyden chamber assays with Matrigel matrix-coated membranes were performed to compare the invasion potential (n=3/group). In all panels, data are reported as means±SEMs; *, , and * indicate p<0.05, <0.01, and <0.001, respectively. Statistical comparisons between 2 groups were performed using Student's t-test. EV: empty vector, PI: propidium iodide.

(FIG. 9A) Scheme showing groups of patients with CRC according to dysadherin expression. mRNA expression data from patient tumors were obtained from the GEO database (GSE21510), and patients were divided into 2 groups according to median dysadherin level (dysadherinhigh, n=52; dysadherinlow, n=52). The list of differentially expressed genes (DEGs) was obtained through R2 analyses with the GEO platform (p<0.001) and used for gene set enrichment analyses (GSEA) to determine the associated gene signatures. (FIG. 9B) Gene signatures related to features of cancer malignancy, such as poor outcome clusters, metastatic clusters, and cell migration clusters, were significantly enriched in the dysadherin-high tumors. (FIG. 9C) Significant enrichment of ECM receptor pathway genes, such as genes involved in ECM organization, ECM regulators, and integrin signaling, was observed in the dysadherin-high tumors of patients with CRC. (FIG. 9D) The list of DEGs (n=4,437, p<0.05) in dysadherin-KO SW480 cells was subjected to IPA. The bar graph shows the top 20 significant diseases and functions related to dysadherin KO. Cancer is most significantly affected by dysadherin KO. Dys: dysadherin, FDR: false discovery rate, NES: normalized enrichment score.

(FIG. 10A) GSEA was performed using the mRNA sequencing profiles of dysadherin-KO and control (EV-transfected) cells. Gene signatures associated with the ECM-integrin pathway were significantly enriched in control cells compared with dysadherin-KO cells. (FIGS. 10B,10C) Ingenuity Pathway Analysis was performed with the list of differentially expressed genes in dysadherin-KO cells to reveal the dysadherin-associated mechanism. (FIG. 10B) Disease and function analyses show significant reductions in tumor frequency, tumor incidence, and malignant tumor development upon dysadherin KO. Categories with p<0.05 and |z-score|>2 were considered statistically significant. (FIG. 10C) Upstream analysis indicates the potential link between integrin pathways and reduced cancer-related functions, with significant reductions in integrin target gene expression upon dysadherin KO, which collectively led to a decrease in tumor development (FIGS. 10D, 10E). The potential relationship between dysadherin and the integrin signaling pathway, validated by RT-qPCR analyses of integrin target genes and by IF in SW480 (FIG. 10D) and HCT116 (FIG. 10E) cell lines. RT-qPCR heatmaps show changes in integrin signaling target genes upon dysadherin KO (FIG. 10D) and OE (FIG. 10E). IF staining for human active β1 integrin (12G10) and dysadherin in dysadherin-KO or -OE CRC cells. (FIG. 10F) IF staining for murine active β1 integrin (9EG7) and dysadherin in intestinal tumor tissues of $Apc^{Min/+}$;$Fxyd5^{+/+}$ and $Apc^{Min/+}$;$Fxyd5^{-/-}$ mice (n=8/group). *** indicates p<0.001. Dys: dysadherin, FC: fold change, FDR: false discovery rate, MFI: mean fluorescence intensity, NES: normalized enrichment score, EV: empty vector.

(FIG. 11A) Schematic flow for identification of dysadherin-binding proteins based on co-immunoprecipitation (co-IP) with anti-dysadherin (M53) monoclonal antibody and subsequent liquid chromatography with tandem mass spectrometry (LC-MS). LC-MS identified a total of 301 proteins in the co-IP samples. After exclusion of 20 keratins as accidental or unavoidable contaminants of proteomics assays, functional annotation of the remaining 281 proteins was performed by DAVID functional annotation analysis (https://david.ncifcrf.gov/), which showed the significant enrichment of the ECM proteins. Fibronectin was one of the ECM proteins significantly enriched by co-IP. (FIG. 11B) Confirmation of purified recombinant dysadherin constructs generated from E. coli. (FIG. 11C) Schematic of the dysadherin open reading frame (ORF) sequence used to establish HCT116 cell lines overexpressing wild-type (full length) or mutant dysadherin. Arrows indicate the binding sites of primer sets that were designed to detect mutant forms of dysadherin. Right: confirmation of wild-type or mutant dysadherin OE by RT-qPCR analysis (n=3/group). (FIG. 11D) IF analyses for visualizing His-tagged dysadherin (green) and fibronectin (red). His-tagged wild-type or mutant dysadherin was transfected into HCT116 cells, and the localization of dysadherin was visualized by staining with an anti-His antibody. OE of wild-type or ΔC-mutant dysadherin increased the colocalization of dysadherin and fibronectin on the cellular membrane, while OE of ΔN-mutant dysadherin did not. (FIG. 11E) IF staining for fibronectin and dysadherin in SW480 cells with and without dysadherin KO. (FIG. 11F) IF staining for fibronectin and dysadherin in intestinal tumor tissues from $Apc^{Min/+}$;$Fxyd5^{+/+}$ and $Apc^{Min/+}$;$Fxyd5^{-/-}$ mice. Data indicate the means±SEMs; *** indicates p<0.001 and ns indicates no significance. Statistical comparisons between 3 groups were performed using one-way ANOVA with Dunnett's multiple comparison tests. Statistical comparisons between 2 groups were performed using Student's t-test. Dys: dysadherin, FN, fibronectin, Full: full length, GO: gene ontology, IgG: immunoglobulin G, MFI: mean fluorescence intensity, SDS-PAGE: sodium dodecyl sulfate polyacrylamide gel electrophoresis, ΔC: ΔC-mutant, ΔN: ΔN-mutant.

FIGS. 12A-11E illustrate the extracellular domain of dysadherin directly binds fibronectin. (FIG. 12A) Co-IP with anti-dysadherin antibody (M53) and subsequent immunoblot analyses validate the binding of dysadherin to endogenous fibronectin in CRC cells.

FIG. 13A schematically shows the candidate sites and the sequences of peptides used to verify which could be bound with fibronectin.

(FIGS. 14A-14D) Cancer cell adhesion to various ECM proteins was determined by measuring the relative number of bound cells on culture plates coated with the indicated proteins 1 h after cell seeding. Both HCT116 and SW480 cells showed greater adhesive capacity with higher concentrations of ECM coating. Dysadherin OE increased the number of cells that adhered to fibronectin, while dysadherin KO reduced the number of adherent cells. The extent of cell adhesion to laminin or collagen was not affected by dysadherin OE or KO. Upper: representative images of adhered cells stained with crystal violet. Bottom: graphs show the relative cell number determined by measuring absorbance at OD 595 nm (n=3/group). (FIG. 14E) Activation of FAK (p-FAK) in SW480 cells 1 h after cell seeding on culture plates with or without fibronectin coating, visualized by IF. (FIG. 14F) The gene silencing effects of siRNAs targeting fibronectin (siFN1) were confirmed by RT-qPCR analyses 96 h after transfection. Cells transfected with scrambled siRNAs (siC-TRL) were used as the control. (FIG. 14G) Immunoblot analyses show a reduction in fibronectin protein levels in siFN1-transfected cells without an effect on dysadherin protein levels. (FIG. 14H) FAK activation in 4-day cultures of CRC cells after gene silencing of fibronectin. In all panels, data indicate the means±SEMs; *** indicates p<0.001 and ns indicates no significance. Statistical comparisons were performed using two-way ANOVA with the Bonferroni multiple comparison test for 2 groups, or using oneway ANOVA with Dunnett's multiple comparison tests for 3 or more groups. BSA: bovine serum albumin, COL1: collagen type 1, Dys: dysadherin, FN: fibronectin, LM: laminin, OD: optical density.

(FIG. 15A) Activation of FAK (p-FAK) in HCT116 cells with and without OE of dysadherin 1 h after cell seeding on culture plates with or without fibronectin coating, visualized by IF. (FIG. 15B) IF staining for p-FAK and dysadherin in intestinal tumor tissues from $Apc^{Min/+}$;$Fxyd5^{+/+}$ and $Apc^{Min/+}$;$Fxyd5^{-/-}$ mice. Graph shows fibronectin protein levels in the indicated groups (n=8/group). (FIGS. 15C,15D) The extent of FAK activation was determined in CRC cells with and without KO (SW480 cells) and OE (HCT116 cells) of dysadherin at the indicated time points after cell seeding on fibronectin-coated culture dishes. (FIG. 15E,15F) FAK activation was measured in 4-day cultures of CRC cells without fibronectin coating. (FIG. 15G) The survival potential of HCT116 cells overexpressing wild-type (full-length) or mutant dysadherin compared in clonogenic assays (n=3/group). (FIG. 15H) Comparison of invasion potential of HCT116 cells overexpressing wild-type or mutant dysadherin by Boyden chamber assay. In all panels, data are reported as means±SEMs; *** indicates p<0.001. Statistical comparisons between 2 groups were performed using Student's t-test. Dys: dysadherin, FN: fibronectin, MFI: mean fluorescence intensity, ΔC: ΔC-mutant, ΔN: ΔN-mutant, T-FAK: [definition], EV: empty vector.

(FIG. 16A) The number of viable cells was measured with an automated cell counter (Countess II, ThermoFisher Scientific, Waltham, MA, USA) at the indicated time points (n=3/group) in HCT116 cells overexpressing wildtype (full length) or mutant dysadherin. EV-transfected cells were used as controls. Deletion of the extracellular domain of dysadherin (ΔN-mutant) abrogated the dysadherin-induced increase in tumor growth, while the ΔCmutant did not. (FIG. 16B) To determine the effect of fibronectin and FAK signaling on cancer cell growth, dysadherin-OE or control cells were transfected with control siRNA (siCTRL) or siRNAs targeting fibronectin (siFN1). At 24 h after transfection, cells were detached, reseeded, and incubated for 12 h for cell attachment. Then cells were incubated for 36 h with or without FAK inhibitor treatment (VS-4718, 3 μM). The relative cell numbers were determined by MTT assays (n=3/group). (FIG. 16C) Immunoblot confirming the inhibitory effects of FAK inhibitor (VS-4718) on fibronectin-induced FAK activation. Cells were seeded on fibronectin-coated culture plates with or without VS-4718, at 1 or 3 μM. After 4 h, the cells were lysed and whole-cell extracts were subjected to immunoblot analyses to visualize the FAK activation status. (FIG. 16D) The migration potential of HCT116 cells overexpressing wild-type or mutant dysadherin were compared by wound healing assays. To determine the effect of fibronectin and FAK signaling on cancer cell migration, cells were transfected as described in (FIG. 16B). At 24 h after transfection, cells were detached and reseeded for a wound healing assay. The black dotted line indicates initial wound area, and the blue line indicates the cell boundaries determined after a 48-h incubation in serum-free media. FAK inhibitor (VS-4718, 1 μM) was added at the initial time point of the wound healing assay. Bar graphs show the percentage of wound closure (n=3/group). (FIG. 16E) The survival potential of HCT116 cells overexpressing wildtype dysadherin or EV were compared. Cells were transfected with control siRNA (siCTRL) or siRNA targeting fibronectin (siFN1). The next day, cells were incubated for 24 h with or without FAK inhibitor (VS-4718, 3 μmol/L) then detached and reseeded for clonogenic assays (n=3/group). (FIG. 16F) Comparison of invasion potential of HCT116 cells overexpressing wild-type dysadherin or EV by Boyden chamber assays. Fibronectin knockdown was performed as described in e. The transfected cells were detached and reseeded on the upper chamber with or without FAK inhibitor (3 μmol/L) in serum-free media. After a 24-h incubation, the cells that invaded through to the bottom of the membrane were fixed, stained with crystal violet, and counted under a phase-contrast microscope (n=3/group). (FIG. 16G) IF staining for dysadherin and fibronectin or p-FAK in CRC patient tumors. Patients were classified as high or low expressors of dysadherin. Graphs show the protein levels of fibronectin or p-FAK within tumor epithelium in the indicated groups (n=3/group). Statistical comparisons between 2 groups were performed using Student's t-test. EV: empty vector, FN: fibronectin, Full: full length, ΔC: ΔC-mutant, ΔN: ΔN-mutant.

(FIG. 17A) The extent of mechanical force exerted by CRC cells was measured by collagen gel contraction assays. Contractile index implies the percentage gel contraction$^{perturbation}$/percentage gel contraction$^{control}$. Thus, an increase in the contractile index is an increase in contraction. Images show CRC cell-induced gel contraction after 48 h of cell seeding. Graph shows the extent of dysadherin KO- or OE-induced gel contraction relative to control cells. (FIGS. 17B,17C) IF analysis of mechanotransduction by visualizing paxillin-positive focal adhesions (FIG. 17B) and YAP (FIG. 17C) in CRC cells with dysadherin OE or KO. Hydrogels with a defined elastic modulus (0.5 kPa and 12 kPa) were used as a positive control for mechanical force. (FIG. 17D) RT-qPCR validation for YAP target gene expression in CRC cells upon dysadherin OE or KO.

DETAILED DESCRIPTION

Figure 1A:
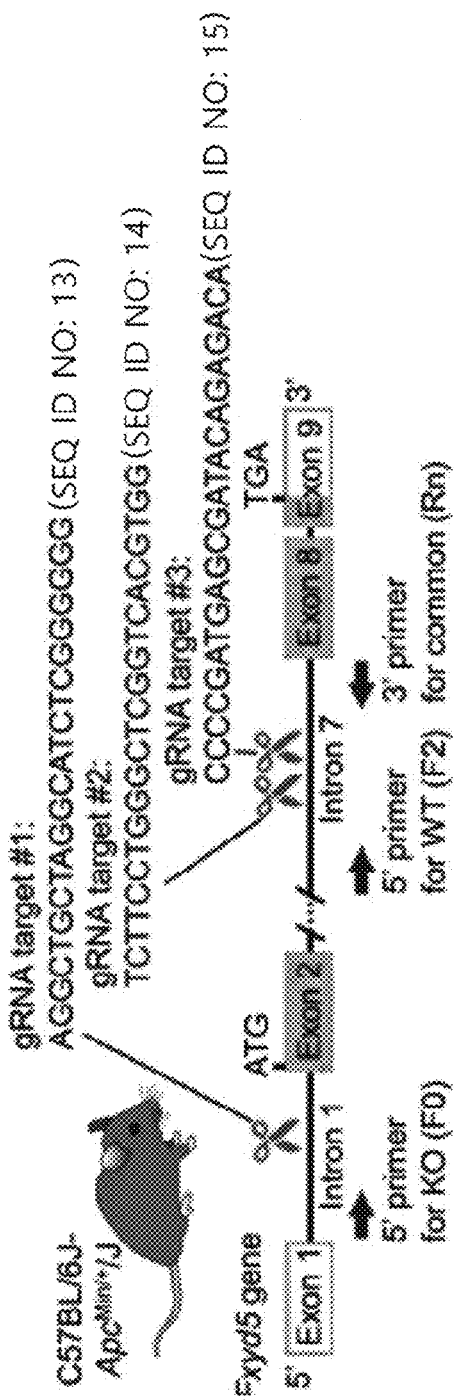
Figure 1B:
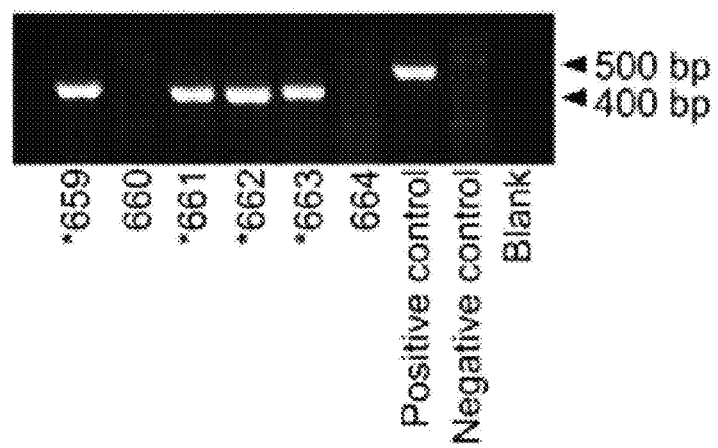
Figures 1D, 1E:
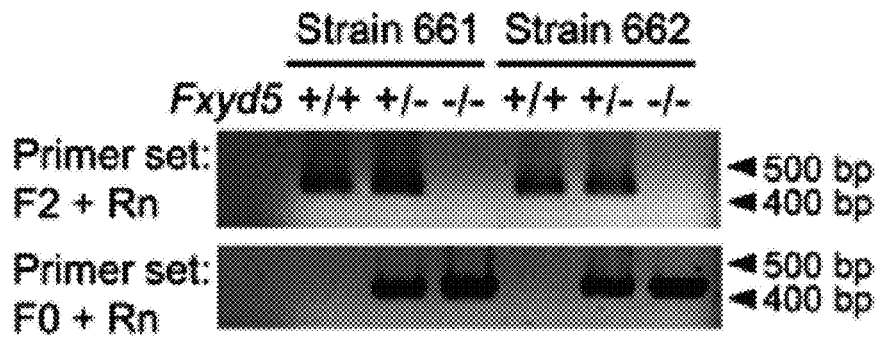

Hereinafter, the present invention will be described in detail.

The present invention relates to a peptide including at least a portion of a sequence of SEQ ID NO: 1 (AA 64-115 of FIG. 12B herein), wherein the portion has a length of 5aa or more.

The peptide may include 5aa or more sequences starting from any one of the sequence of SEQ ID NO: 1, that is, all portions that can be optionally cleaved from SEQ ID NO: 1, or may consist of the entire sequence of SEQ ID NO: 1. A portion of the sequence of SEQ ID NO: 1 may be a contiguous amino acid sequence.

The peptide may have a length of 5 to 52aa, 5 to 30aa, 5 to 20aa, 5 to 15aa, 10 to 20aa, or 10 to 15aa, but it is not limited thereto.

The portion may have a length of 10aa or more.

Specifically, the peptide may consist of any one of SEQ ID NOs: 2 to 7. The SEQ ID NOs: 2 to 7 are portions of an extracellular domain of dysadherin, and correspond to sequences N #04 to N #09 depicted in FIG. 12B of the present application, respectively.

The peptide may consist of or include, for example, a sequence selected from the group consisting of PADETPQPQTQ (SEQ ID NO: 8), TQQLEGTDGP (SEQ ID NO: 9), LVTDPETHKS (SEQ ID NO: 10), KAAHPTDDTT (SEQ ID NO: 11) and TLSERPSPST (SEQ ID NO: 12) in a portion of the sequence of SEQ ID NO: 1.

The portion is a motif portion that can be bound to fibronectin in peptide of SEQ ID NO: 1.

The peptide may have 80% or more, 90% or more, 95% or more, 97% or more, or 99% or more homology to the sequence as long as it maintains binding property to fibronectin.

The peptide may inhibit binding between dysadherin and fibronectin by competitively binding to fibronectin with dysadherin.

The peptide may be used for the prevention or treatment of cancer by weakening survival, migration or invasion of cancer cells.

Specifically, the peptide has a binding activity to fibronectin and competitively binds to fibronectin with dysadherin, such that it can prevent binding between dysadherin in the cell membrane of cancer cells and fibronectin in ECM. The peptide inhibits adhesion between cancer cells which are strengthened by the binding, and subsequent biochemical signal transduction, for example, FAK and YAP activations, thereby weakening survival, migration or invasion of the cancer cells.

Dysadherin is cell membrane glycoprotein which is overexpressed in a broad range of cancers. Types of cancer that can be used therapeutically with the peptide is not particularly limited, and may be, for example, colorectal cancer, breast cancer, colon cancer, small intestinal cancer, rectal cancer, ovarian cancer, cervical cancer, prostate cancer, testicular cancer, penile cancer, urothelial cancer, ureteral cancer, renal pelvic cancer, esophageal cancer, laryngeal cancer, gastric cancer, gastrointestinal cancer, skin cancer, keratoacanthoma, follicular carcinoma, melanoma, lung cancer, small cell lung carcinoma, non-small cell lung carcinoma (NSCLC), lung adenocarcinoma, squamous cell carcinoma of the lung, pancreatic cancer, thyroid cancer, papillary cancer, bladder cancer, liver cancer, bile duct cancer, bone cancer, hair cell cancer, oral cancer, lip cancer, tongue cancer, salivary gland cancer, pharyngeal cancer, kidney cancer, vulvar cancer, thyroid cancer, endometrial cancer, uterine cancer, brain cancer, central nervous system cancer, peritoneal cancer, hepatocellular carcinoma, Hodgkin disease or leukemia, and preferably colorectal cancer, liver cancer or breast cancer.

A method for manufacturing the peptide is not particularly limited, and the peptide may be obtained by synthesis or by transforming a gene that expresses the peptide in microorganisms.

The peptide may be administered to an animal, including a human, to be treated for prevention or treatment of cancer.

The peptide may be administered in a prophylactically or therapeutically effective amount.

As used herein, the term "effective amount" refers to an amount of peptide that can exhibit the above-described effects. The effective amount of the peptide may vary depending on the commercialized form, etc., but a daily dose may be, for example, 0.0001 to 100 mg/kg based on an amount of the peptide.

The administration means introducing the peptide into a subject by any suitable method known in the art. The administration route of the composition of the present invention is not particularly limited as long as it can reach the target tissue, and may be administered through various oral or parenteral routes.

For example, the composition of the present invention may be administered by topical administration around the tumor, intraperitoneal, intravenous, intramuscular, subcutaneous, intradermal, oral, intranasal, intrapulmonary or rectal administration, but it is not limited thereto.

When administering the peptide, it may be administered together with one or more active ingredients that exhibit the same or similar function, or may be administered with a compound that maintains/increases solubility and/or absorption of the active ingredient.

In addition, the present invention relates to a pharmaceutical composition for the prevention or treatment of cancer, which includes at least a portion of a sequence of SEQ ID NO: 1, wherein the portion includes a peptide having a length of 5aa or more.

The portion may have a length of 10aa or more.

Specifically, the peptide may include any one of SEQ ID NOs: 2 to 7. The SEQ ID NOs: 2 to 7 correspond to sequences N #04 to N #09 depicted in FIG. 12B of the present application, respectively.

The peptide may include, for example, a sequence selected from the group consisting of PADETPQPQTQ (SEQ ID NO: 8), TQQLEGTDGP (SEQ ID NO: 9), LVTD-PETHKS (SEQ ID NO: 10), KAAHPTDDTT (SEQ ID NO: 11) and TLSERPSPST (SEQ ID NO: 12) in a portion of the sequence of SEQ ID NO: 1.

As described above, at least a portion of the sequence of SEQ ID NO: 1, for example, any one of SEQ ID NOs: 2 to 7, or a peptide including a sequence selected from the group consisting of SEQ ID NOs: 8-12 inhibits survival, migration or invasion of cancer cells by preventing binding between dysadherin and fibronectin, such that it can be used for prevention or treatment of cancer. Further, the composition includes the peptide, such that it may have a preventive or therapeutic effect on cancer, which is equal to or higher than that of the peptide.

A length of the peptide, and additionally included sequences, etc. are not limited, as long as it includes a motif portion which binds to fibronectin.

The peptide may include a plurality of portions of the sequence of SEQ ID NO: 1, and the plurality of sequences may be the same as or different from each other.

In addition to the above sequence, the peptide may further include other peptide sequences having an anti-cancer effect or enhancing the effects of the peptide.

For example, in addition to the portion of the sequence of SEQ ID NO: 1, the peptide may further include other peptide sequences derived from dysadherin, specifically, a peptide sequence at a site where dysadherin binds to an extracellular matrix material in regulating tumor formation. The extracellular matrix material may be, for example, one selected from materials listed in Table 5. The peptide may include a linker for linking the peptides.

The peptide may include His-tag, which is an amino acid sequence with which histidines are overlapped. In this case, by allowing it to bind to nickel better, the peptide may be easily purified by affinity chromatography using nickel resin. For example, 6 to 8 histidines may be used.

The composition may be administered in combination with compositions including the peptides, respectively.

The composition of the present invention may be formulated and used in the form of oral formulations such as powder, granules, tablets, capsules, suspension, emulsion, syrup, aerosol, etc., external applications, suppositories, and sterile injection, but it is not limited thereto.

Carriers, excipients and diluents able to be contained in the composition may include, for example, lactose, dextrose, sucrose, dextrin, maltodextrin, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil, but they are not limited thereto. Such formulations are produced using diluents or excipients such as fillers, extenders, binders, wetting agents, disintegrants, surfactants, etc., which are typically used in the art, but they are not limited thereto.

Solid formulations for oral administration may include tablets, pills, powder, granulates, capsules, etc., without limitation thereof, and such solid formulations may be prepared by admixing the compound as described above with at least one excipient, for example, starch, calcium carbonate, sucrose, lactose, gelatin and the like. Further, in addition to simple excipients, lubricants such as magnesium stearate, talc, etc. may also be used.

Liquid formulations for oral use may include suspending agents, oral liquids, emulsions, syrup and the like. Other than simple diluents commonly used in the art such as water and liquid paraffin, various excipients such as wetting agents, sweeteners, fragrances, preservatives, etc. may be used.

Formulations for parenteral administration may include sterile aqueous solution, non-aqueous solvent, suspending agents, emulsions, freeze-dried preparations, suppositories and the like. The non-aqueous solvents or suspending agents used herein may include propylene glycol, polyethylene glycol, vegetable oil such as olive oil, injectable ester such as ethyl oleate, etc. As a base of the suppository, witepsol, macrogol, tween 60, cacao butter, laurin, glycerogelatin, and the like may be used.

On the other hand, the composition of the present invention may further contain a component well known to have an anti-cancer effect by itself or assist the anti-cancer effect, thereby obtaining a more desirable anti-cancer effect.

Hereinafter, the present invention will be described in detail with reference to examples.

Methods

1. Study Design

Prior approval for animal studies was obtained from the Institutional Animal Care and Use Committee (IACUC) of the Gwangju Institute of Science and Technology (GIST, No. GIST 2018-049). For all analyses, sample sizes were determined in accordance with the 3 R (replacement, reduction, and refinement). Humane end points were predefined as impaired breathing and/or hunching with 10% or more weight loss. Outcome assessment was performed blindly without reference to genotype. Reporting is consistent with the ARRIVE guidelines. In vitro experiments were all performed on three separate occasions. In vitro analyses were not blinded. Outliers were included in all experiments. Analysis of dysadherin expression in patients with CRC was preapproved by the Institutional Review Board at GIST (No. 20200108-BR-50-07-02). All work related to human tissues was conducted in accordance with the Helsinki Declaration. Written informed consent was obtained from all participants prior to the study. This was a retrospective study using tissue microarray (TMA) slides, and therefore, study size calculation was not performed. Histological assessment was performed blindly and scored automatically using Image-Pro Premier 9.2 software (Media Cybernetics Inc., Rockville, MD, USA) in a blinded manner without any clinical information. The data of clinical relevance are reported consistently with the REMARK guidelines.

2. Chemicals and Reagents

10× cell lysis buffer (#9803), 3× sodium dodecyl sulfate (SDS) sample buffer (#7722), and Protein A agarose beads (#9863) were purchased from Cell Signaling Technology (Beverly, MA, USA). Fluorescence-activated cell sorting (FACS) Lysing™ Solution was purchased from BD Biosciences (San Diego, CA, USA). TRIzol reagent was purchased from Ambion (Austin, TX, USA). VS-4718 was purchased from Tocris Bioscience (Ellisville, MO, USA). Anti-dysadherin monoclonal antibody (M53) was kindly gifted by Dr. Yoshinori Ino (National Cancer Center Research Institute, Tokyo, Japan).

3. Generation of Fxyd5 Knockout (KO) Mice

The $Fxyd5^{-/-}$ mice were purchased from Vitalstar (Beijing, China). Ear tagging was used for identification of mice and recordkeeping throughout the research project. Briefly, Fxyd5, mice were generated using CRISPR/Cas9 technology. Three guide RNAs (gRNA sequences: AGGCTGCTAGGCATCTCGGGGGG(SEQ ID NO: 13), TCTTCCTGGGCTCGGTCACGTGG (SEQ ID NO: 14), and CCCCGATGAGCGATACAGAGACA(SEQ ID NO: 15)) were used to cut the genomic DNA at Fxyd5 introns 1 and 7, which resulted in the deletion of exons 2-7, which contain the ATG start codon and most of the coding sequences. Four strains harboring the Fxyd5 mutation (gene targeting efficiency: 4/6=66.66%) were identified. Strain 661, a heterozygote strain carrying 5740-bp deletions of Fxyd5 (Fxyd5 null), was selected as a founder. Using strain 661, at least 5 backcrosses with C57BL/6J were conducted to minimize off-target effects. No sex-specific differences were observed. The list of primers used for genotyping is provided in Table 1A-D.

TABLE 1A

| Target | Sequence | | Applications | |
|---|---|---|---|---|
| Mouse Fxyd5 | GCAGTTAGTTCTGTTCTGTGCCTCG | | 5' primer (F0) for KO Genotyping | (SEQ ID NO: 16) |
| Mouse Fxyd5 | ATGGTGACTGAGGATCAGGGTCTTG | | 5' primer (F2) for WT. Genotyping | (SEQ ID NO: 17) |
| Mouse Fxyd5 | GCACACCTATAACCTCAAGCCTCAG | | 3' primer (Rn) for KO and WT, Genotyping | (SEQ ID NO: 18) |
| Mouse HPRT | F: | GCCTAAGATGAGCGCAAGTTG | Real-time RT-qPCR, Endogenous control | (SEQ ID NO: 19) |
|  | R: | TACTAGGCAGATGGGCACAGG |  | (SEQ ID NO: 20) |
| Mouse Fxyd5 | F: | GAAAGGTACCXXTGCAGTKT | Real-time RT-QPCR | (SEQ ID NO: 21) |
|  | R: | ACCAGCAGTCGCCGTTTC |  | (SEQ ID NO: 22) |
| Human FXYD5 (N-term) | F: | TCCCACTGATGACACCACGA | For WT and ΔC, Real-time RT- | (SEQ ID NO: 23) |
|  | R: | AAACCAGATGGCTTGAGGG |  | (SEQ ID NO: 24) |
| Human FXYD5 (C-term) | F: | GTCGCAGGTGTGCTGTTCAT | For WT and ΔN, qPCR | (SEQ ID NO: 25) |
|  | R: | CTGCAATGATTCCGCCATAACC | Real-time RT- | (SEQ ID NO: 26) |
| Human SPARC | F: | AGACAGGGGTACCTGTGGG | Real-time RT-qPCR | (SEQ ID NO: 27) |
|  | R: | CACATGGGGGTGTTGCTCTC |  | (SEQ ID NO: 28) |
| Human MMP2 | F: | AAGGATGGCAAGTACGGCTT | Real-time RT-qPCR | (SEQ ID NO: 29) |
|  | R: | AAACTTGCAGGGCTGTCCTT |  | (SEQ ID NO: 30) |
| Human CD40 | F: | AATGCCTTCCTTGCGGTGA4 | Real-time RT-qPCR | (SEQ ID NO: 31) |
|  | R: | TCTCACAGGGCTCACTCGTA |  | (SEQ ID NO: 32) |
| Human CCL5 | F: | TCAAGACAGCACGTGGACCT | Real-time RT-AFCR | (SEQ ID NO: 33) |
|  | R: | CGGGCAATGTAGGCAAAGCA |  | (SEQ ID NO: 34) |

TABLE 1B

| | | | | |
|---|---|---|---|---|
| Human MMP9 | F: GTGGAAATCTCTGGGGCCTG | | Real-Sme RT- | (SEQ ID NO: 35) |
| | R: ATGTTGTGGTGGTGCCACTT | | qPCR | (SEQ ID NO: 36) |
| Human TNF | F: CAGGCAGGTTCTCTTCCTCTCA | | Real-time RT- | (SEQ ID NO: 37) |
| | R: AGGAGAAGAGGCTGAGGAACAA | | qPCR | (SEQ ID NO: 38) |
| Human FOS | F: CAGACTACGAGGGGTCATCC | | Real-time RT- | (SEQ ID NO: 39) |
| | R: CGTGGGAATGAAGTTGGCAC | | qPCR | (SEQ ID NO: 40) |
| Human GPX4 | F: ACGCCCGATACGCTGAGT | | Real-time RT- | (SEQ ID NO: 41) |
| | F: TCACGCAGATCTTGGTGAACATA | | qPCR | (SEQ ID NO: 42) |
| Human RAC2 | F: ATCAGCTACACCACCAACGC | | Real-time RT- | (SEQ ID NO: 43) |
| | R: ACGTCCGTCTGTGGATAGGA | | qPCR | (SEQ ID NO: 44) |
| Human MMP14 | F: CGTTGGACTCTCAGGAATGAGG | | Rex-time RT- | (SEQ ID NO: 45) |
| | R: TTCTGCGTGTCCATCCACTGGT | | qPCR | (SEQ ID NO: 46) |
| Honda CHRD | F: CGCATCAGTCGACACATTGC | | Rex-time RT- | (SEQ ID NO: 47) |
| | R: CGTCACTGCTTGTCCCTACC | | qPCR | (SEQ ID NO: 48) |
| Human COL2A1 | F: CATCGCACCCTCTCACAGTT | | Rex-time RT- | (SEQ ID NO: 49) |
| | R: GTGTCTGCCTTGACCCAAAG | | qPCR | (SEQ ID NO: 50) |
| Human CDKN1A | F: ACTTTGTCACCGAGACACCA | | Real-time RT- | (SEQ ID NO: 51) |
| | R: CAGCAGAGCAGGTGAGGTG | | qPCR | (SEQ ID NO: 52) |
| Human IGFBP2 | F: TGCACATCCCCAACTGTGAC | | Real-time RT- | (SEQ ID NO: 53) |
| | R: TGTAGAAGAGATGACACTCGGG | | qPCR | (SEQ ID NO: 54) |
| Human CEBPB | F: TGATAAACTCTCTGCTTCTCCCT | | Real-time RT- | (SEQ ID NO: 55) |
| | R: GTTGCGTCAGTCCCGTGT | | qPCR | (SEQ ID NO: 56) |
| Human JUNB | F: ACCACGACGACTCATACACAG | | Real-time RT- | (SEQ ID NO: 57) |
| | R: CGAGCCCTGACCAGAAAAGT | | qPCR | (SEQ ID NO: 58) |

TABLE 1C

| | | | |
|---|---|---|---|
| Human FN1 | F: AGCAAGCCCGGTTGTTATGA | Real-time RT- | (SEQ ID NO: 59) |
| | R: CCCACTCGGTAAGTGTTCCC | qPCR | (SEQ ID NO: 60) |
| Human PPL4 | F: TGCCATCGCCAAGGAGTAG | Real-time RT- | (SEQ ID NO: 61) |
| | R: TGCACAGACGGTCACTCARA | qPCR, Endogenous control | (SEQ ID NO: 62) |
| Human SGK1 | F: CGGAATGTTCTGTTGAAGAATGTG | Real-time RT- | (SEQ ID NO: 63) |
| | R: TGTCAGCAGTCTGGAAAGAGAAGT | qPCR | (SEQ ID NO: 64) |
| Human BIRC5 | F: AGCCCTTTCTCAAGGACCACC | Real-time RT- | (SEQ ID NO: 65) |
| | R: TTGAAGCAGAAGAAACACTGGGC | qPCR | (SEQ ID NO: 66) |
| Human ETV5 | F: CAGTCAACTTCAAGAGGGTTGG | Real-time RT- | (SEQ ID NO: 67) |
| | R: TGCTCATGGCTACAAGACGAC | qPCR | (SEQ ID NO: 68) |
| Human MTSS1 | F: ACCATCATCAGCGACATGAA | Real-time RT- | (SEQ ID NO: 69) |
| | R: CACATCCTGGTGAGAGCAGA | qPCR | (SEQ ID NO: 70) |
| Human VIM | F: ACCCGCACCAACGAGAAGGT | Real-time RT- | (SEQ ID NO: 71) |
| | R: ATTCTGCTGCTCCAGGAAGGG | qPCR | (SEQ ID NO: 72) |
| Human NDRG1 | F: AAGATGGGCGACTGTGGC | Real-time RT- | (SEQ ID NO: 73) |
| | R: TCAGGGGTCATGCTA | qPCR | (SEQ ID NO: 74) |
| Human TNS1 | F: TCAAGTGGAAGAACTTGTTTGCTT | Real-time RT- | (SEQ ID NO: 75) |
| | R: CACCACAATATAGTGGAGGCACA | qPCR | (SEQ ID NO: 76) |
| Human CDC20 | F: GCCCACCAAGAAGGAACATC | Real-time RT- | (SEQ ID NO: 77) |
| | R: TTTTCCACTGAGCCGAAGGA | qPCR | (SEQ ID NO: 78) |
| Human DUT | F: GTCTCCTCGCTCGCCTTCT | Real-time RT- | (SEQ ID NO: 79) |
| | R: GGTGAAATGGCGGGTGTCT | qPCR | (SEQ ID NO: 80) |
| Human TGM2 | F: AGAAGAGCGAAGGGACGTACTG | Real-time RT- | (SEQ ID NO: 81) |
| | R: AGTCTACCACGTCGGCATTGAC | qPCR | (SEQ ID NO: 82) |

TABLE 1D

| | | | |
|---|---|---|---|
| Human CTGF | F: CCAATGACA ACGCCTCCTG | Real-time | (SEQ ID NO: 83) |
| | R: TGGTGCAGC CAGAAAGCTC | RT-qPCR | (SEQ ID NO: 84) |
| Human CAVIN2 | F: AAGAGCGCA TGGATAGGCAG | Real-time | (SEQ ID NO: 85) |
| | R: AAGAGCGCA TGGATAGGCAG | RT-qPCR | (SEQ ID NO: 86) |
| Human FLNA | F: CATCAAGTA CGGTGGTGACG | Real-time | (SEQ ID NO: 87) |
| | R: ACATCCACCT CTGAGCCATC | RT-qPCR | SEQ ID NO: 88 |

4. Animal Models

All mice used in this study were housed under specific pathogen-free conditions and cared for in accordance with international guidelines preapproved by the IACUC at GIST. The exact number of mice for each experiment is noted in the description of the Figures. To examine the impact of dysadherin deficiency on intestinal tumor development, we developed a new murine model by crossing female dysadherin-KO (Fxyd5$^{-/-}$) mice with male Apc$^{Min/+}$ mice on a C57BL/6J background. Apc$^{Min/+}$ mice were purchased from Jackson Laboratory (Bar Harbor, ME, USA) and the Fxyd5$^{-/-}$ mice were purchased from Vitalstar (Beijing, China). Ear tagging was used for identification of mice and record keeping throughout the research project. To compare the status of tumor development between Apc$^{Min/+}$;Fxyd5$^{-/-}$ and Apc$^{Min/+}$;Fxyd5$^{+/+}$ mice, male mice were sacrificed at the ages of 4, 6, 8, and 20 weeks, and the intestinal tracts were opened longitudinally and carefully examined for tumors in a blinded manner without any genotype information. To prepare the chemically induced intestinal tumor mouse model, 8-week-old male wild-type (Fxyd5$^{-/+}$) and Fxyd5$^{-/-}$ mice were treated with a single intraperitoneal injection of 10 mg/kg AOM (day 0). One week later, the mice were treated with 2.0% DSS in drinking water for 1 week, and then the DSS-containing drinking water was exchanged for plain water for 2 weeks. This 3-week DSS treatment course was performed a total of 4 times for 12 weeks. After 1 additional week, the mice were sacrificed, and the status of CRC development was evaluated as described above.

5. Apc$^{Min/+}$ Mouse Polyp-Derived Tumoroid Culture

Single cells were isolated from the intestinal polyps of 20-week-old Apc$^{Min/+}$ mice and cultured as described in a previous report with slight modifications(Shimamura T, Sakamoto M, Ino Y, Sato Y, Shimada K, Kosuge T, et al. Dysadherin overexpression in pancreatic ductal adenocarcinoma reflects tumor aggressiveness: relationship to e-cadherin expression. Journal of clinical oncology. 2003; 21: 659-67.). Briefly, mouse intestines containing polyps were incubated with ethylenediamine tetraacetic acid (EDTA) chelation buffer for 60 min on ice. After chelation, the detached normal intestinal epithelial cells were removed by centrifugation, while tumor cells remained attached to the mesenchyme. Intestinal fragments with tumor cells were then dissociated with collagenase. The isolated tumor cells were counted and pelleted and a total of 20,000 cells or 100 cells were then mixed with 50 μL or 10 μL of Matrigel (Corning Matrigel. Growth Factor Reduced Basement Membrane Matrix, #356231, Corning, NY, USA) and plated in 24-well plates or 96-well plates, respectively. After the polymerization of Matrigel, 500 mL of IntestiCult™ Organoid Growth Medium (Mouse, #06005, STEMCELL Technology) was added. Beginning on the day of seeding, growth and morphology of organoids were observed daily, and the viability of organoids was evaluated by performing a resazurin-based Cell Titer Blue assay (Promega, Leiden, The Netherlands) on the seventh day of organoid culture. The mean diameter of tumoroids from each well was measured using Image-Pro Premier 9.2 software (Media Cybernetics Inc., Rockville, MD, USA). For generation of the Fxyd5 knockdown tumoroids, isolated tumor cells were transfected with siRNA against the Fxyd5 gene using a NEPA21 superelectroporator (NEPAGENE, Chiba, Japan). The transfected cells were then cultured and monitored as described above. The list of siRNA sequences used for Fxyd5 knockdown is provided in Table 2.

TABLE 2

| Target | | Sequence | |
|---|---|---|---|
| Mouse Fxyd5 | SIRNA #1 | Sense: CUCACU AGU GGG AAG UGU A(dTdT) | (SEQ ID NO: 89) |
| | | Antisense: UAC ACU UCC CAC UAG UGA G(dTdT) | (SEQ ID NO: 90) |
| Mouse Fxyd5 | SIRNA #2 | Sense: CACAUG GUC UCU CUU CCA U(dTdT) | (SEQ ID NO: 91) |
| | | Antisense: AUG GAA GAG AGA CCA UGU G(dTaT) | (SEQ ID NO: 92) |
| Mouse Fxyd5 | SIRNA #3 | Sense: CUG GAU CGA AUU GAG AAC A(dTdT) | (SEQ ID NO: 93) |
| | | Antisense: UGU UCU CAU UCG AAU CCA G(dTdT) | (SEQ ID NO: 94) |
| Human FN1 | SIRNA#1 | Sense: CUCCAUGAUCUGGGACUG(dTdT) | (SEQ ID NO: 95) |
| | | Antisense: ACAGUCCCAGAUCAUGGA(dTdT) | (SEQ ID NO: 96) |
| Human FN1 | SIRNA#2 | Sense: CAGACUUACGGUGGCAACU(dTdT) | (SEQ ID NO: 97) |
| | | Antisense: AGUUGCCACCGUAAGUCU(dTdT) | (SEQ ID NO: 98) |

6. Histological Assessment

All tissue samples were formalin-fixed and paraffin-embedded or frozen in optimal cutting temperature compound (Leica Microsystems, Buffalo Grove, IL, USA) within 30 min after removal from mice. Paraffin-embedded or compound-embedded tissue blocks were manually sectioned with a microtome to obtain 4-5 μm thick sections. Paraffin sections were dewaxed and stained with hematoxylin (Dako, Carpinteria, CA, USA) and eosin (Millipore, Billerica, MD, USA) according to the supplier's instructions. Target proteins were visualized by immunohistochemistry (IHC) and immunofluorescence (IF). Proteins were visualized using the specific antibodies described in Table 3A-3C.

TABLE 3A

| Target | Conjugate | Catalog # (company/provider) | Application |
|---|---|---|---|
| Mouse Ki-67 | — | MA5-14520 | IHC |
| Mouse cleaved-Caspase 3 | — | 9661S (Cell Signaling Technology) | IHC |
| Human Dysadherin | — | M53 (Dr. Ino) | IHC |
| VECTASTAIN® ABC Kit, Rabbit IgG | — | PK-6101 (Vector Laboratories) | IHC |
| VECTASTAIN® ABC Kit, Mouse IgG | — | PK-6102 (Vector Laboratories) | IHC |
| Human Dysadherin | — | M53 (Dr. Ino) | Immunoblot |
| Human E-cadherin | — | 14472S (Cell Signaling Technology) | Immunoblot |
| Human β-actin | — | A5316 (Sigma-Aldrich) | Immunoblot |
| Human Fibronectin | — | ab2413 (Abcam) | Immunoblot |
| Human GAPDH | — | 5174S (Cell Signaling Technology) | Immunoblot |
| Human p-FAK (Y397) | — | 700255 (ThermoFisher) | Immunoblot |
| Human total FAK | — | 3285S (Cell Signaling Technology) | Immunoblot |
| Human Pan-cadherin | — | 4068S (Cell Signaling Technology) | Immunoblot |
| Human YAP | — | ab205270 (Abcam) | Immunoblot |
| Human p-YAP (S217) | — | ab76252 (Abcam) | Immunoblot |
| His-Tag | — | MA1-21315 (ThermoFisher) | Immunoblot |

TABLE 3B

| Goat anti-mouse, Light chain-specific | HRP | 91196S (Cell Signaling Technology) | Immunoblot |
|---|---|---|---|
| Goat anti-mouse | HRP | 554002 (BD Pharmigen™) | Immunoblot |
| Goat anti-rabbit | HRP | 554021 (BD Pharmigen™) | Immunoblot |
| Annexin V | FITC | 556547 (BD Pharmigen™) | FACS |
| Human Dysadherin | — | M53 (Dr. Ino) | IF |
| Human Dysadherin | APC | M53 (Dr. Ino) | IF |
| Human active integrin β1 (12G10) | — | ab202641 (Abcam) | IF |
| Human Fibronectin | — | ab2413 (Abcam) | IF |
| Human EpCAM | — | 93790S (Cell Signaling Technology) | IF |
| Human EpCAM | Alexa488 | 14-9326-82 (eBioscience™) | IF |
| Human F-actin | Alexa555 | A34054 (ThermoFisher) | IF |
| Human p-FAK (Y397) | — | 700255 (ThermoFisher) | IF |
| Human Paxillin | — | AHO0492 (ThermoFisher) | IF |
| Human YAP | — | ab205270 (Abcam) | IF |
| Mouse active integrin β1 (9EG7) | — | 550531 (BD Pharmigen™) | IF |
| Mouse Dysadherin | — | SC-30606 (SantaCruz) | IF |
| Mouse Fibronectin | — | ab2413 (Abcam) | IF |
| Mouse a-SMA | — | A2547 (Sigma-Aldrich) | IF |
| Mouse EpCAM | — | 93790S (Cell Signaling Technology) | IF |
| Mouse p-FAK (Y397) | — | 700255 (ThermoFisher) | IF |

TABLE 3C

| His-tag | — | MA1-21315 (ThermoFisher) | IF |
|---|---|---|---|
| Donkey anti-mouse | Alexa488 | A21202 (ThermoFisher) | IF |
| Donkey anti-rabbit | Alexa555 | A31572 (ThermoFisher) | IF |
| Donkey anti-goat | Alexa488 | A11055 (ThermoFisher) | IF |
| Goat anti-mouse | Alexa555 | A21422 (ThermoFisher) | IF |
| Donkey anti-rat | Alexa555 | A48270 (ThermoFisher) | IF |
| Donkey anti-rabbit | Alexa488 | A21206 (ThermoFisher) | IF |
| Phalloidin | Alexa555 | A34055 (ThermoFisher) | IF |

IHC, immunohistochemistry;
IF, immunofluorescence;
FACS, fluorescence-activated cell sorting;
HRP, horseradish peroxidase;
FITC, fluorescein isothiocyanate;
APC, adenomatous polyposis coli Nuclei were counterstained with hematoxylin (Dako, Carpinteria, CA, USA) for IHC or 4',6-diamidino-2-phenylindole (DAPI, Sigma-Aldrich) for IF. Secondary antibodies conjugated with horseradish peroxidase (HRP, Dako) or with fluorescent dyes (Life Technologies, Carlsbad, CA, USA) were used to visualize target proteins. For IHC, target proteins were visualized by the DAB reaction and observed with light microscopy (Leica Microsystems) at 400× magnification. DAB intensity was automatically quantified with Image-Pro Premier 9.2 software (Media Cybernetics Inc., Rockville, MD, USA) in 3 random spots per every tissue sample in a blinded manner without any genotype information. The integrated optical density (IOD) of the target protein was calculated by multiplying the area and average density. Fluorescence signals were visualized using an Axio Imager 2 (Carl Zeiss, Oberkochen, Germany) or confocal LSM880 microscope (Carl Zeiss) at a total magnification of 400× or 1000×. Relative expression levels of the target protein were measured based on fluorescence intensity as described above and normalized to DAPI intensity.

7. Real-Time Reverse Transcriptase Quantitative Polymerase Chain Reaction (RT-qPCR)

Total RNA was isolated using TRIzol reagent (Invitrogen). The purity of RNA was verified by measuring 260/280 and 260/230 absorbance ratios. cDNA templates were synthesized from 0.5 μg of total RNA using the PrimeScript™ 1st strand cDNA Synthesis Kit (Takara Biomedicals, Kusatsu, Japan) with random primers. Power SYBR Green PCR Master Mix and Step-One Real-time PCR systems (Applied Biosystems, Foster City, CA, USA) were used for the PCR amplification of cDNAs. The list of primers used for RT-qPCR is provided in Table 1A-1C.

8. Clinical Analysis and Statistics

TMA slides from 123 patients with CRC were immunostained to detect dysadherin using a specific monoclonal antibody (M53). The TMA slides contained 3 tumor tissue cores and 2 matched normal tissue cores from each patient. After heat-induced epitope retrieval, the slides were permeabilized and incubated with primary antibodies (1:500) at 4° C. overnight. Following repeated washing steps, the slides were incubated with anti-mouse biotinylated antibody (Vector ABC Kit, Vector Laboratories, Burlingame, CA, USA) for 30 min at room temperature, and dysadherin expression was visualized by the DAB reaction and observed under light microscopy (Leica Microsystems, Buffalo Grove, IL, USA). The expression of dysadherin in the CRC epithelium was automatically quantified with Image-Pro Premier 9.2 software (Media Cybernetics Inc., Rockville, MD, USA) in a blinded manner without any clinical information. Three spots per core were randomly selected, and the IOD of dysadherin was calculated by multiplying the area and average density. The ratio of dysadherin expression in tumor tissues versus normal tissues (average IOD of 3 tumor tissue cores/average IOD of 2 normal tissue cores)

was used to determine the association of dysadherin expression with clinicopathological variables. Patients were divided into two group according to the IOD values; dysadherin-high (>75%, n=27) and dysadherin-low (<75%, n=96). The statistical significance of differences was assessed using the chi-square test or Fisher's exact test for categorical data, and continuous variables were compared using the independent samples t-test. Recurrence-free survival (RFS) was defined as the time from the date of surgery to the date of recurrence or death, whichever occurred first, and patients who were alive at the last follow-up were recorded at that time If neither event had occurred at the time of analysis, the patient was censored. Overall survival (OS) was calculated from the diagnosis of disease to death from any cause, and patients who were alive at last follow-up were recorded at that time. Survival was calculated using the Kaplan-Meier method, and comparisons were made using log-rank tests. Factors associated with RFS and OS were identified by univariate and multivariate Cox proportional hazards regression models with hazard ratios and 95% confidence intervals. Statistical analyses were performed using SPSS version 21.0 (IBM Corporation, Armonk, NY, USA); all p-values were two-sided, and p<0.05 was used as an indicator of statistical significance.

9. Cell Lines

HCT116 (KCLB Cat #10247, RRID:CVCL_0291), SW480 (KCLB Cat #10228, RRID:CVCL_0546), LoVo (KCLB Cat #10229, RRID:CVCL 0399), HCT15 (KCLB Cat #10225, RRID:CVCL 0292), LS174T (KCLB Cat #10188, RRID:CVCL_1384), and HT29 (KCLB Cat #30038, RRID:CVCL_0320) cell lines were purchased from the Korean Cell Line Bank (Seoul, Republic of Korea). The SW48 cell line (ATCC Cat #CCL-231, RRID:CVCL_1724) was purchased from American Type Culture Collection (Rockville, MD, USA). The MC38 C57BL6 murine intestinal tumor cell line (RRID:CVCL_B288) was purchased from Kerafast (Boston, MA, USA). All cells were cultured according to the supplier's instructions. The cells were routinely tested for *mycoplasma* contamination every 6 months using the e-Mycom™ *Mycoplasma* detection kit (iNtron Biotechnology, Seongnam, Republic of Korea), and all experiments were performed within 20 passages from the first thaw.

10. Syngeneic Mouse Model Using Murine Colon Carcinoma Cell Line

Luciferase-labeled MC38 cells (C57BL/6J mice-derived colon carcinoma cell line) were inoculated subcutaneously (s.c.) into 8-week-old male $Fxyd5^{+/+}$ or $Fxyd5^{-/-}$ C57BL/6J mice ($5 \times 10_4$/mouse). Tumor growth was monitored by measuring luciferase activity for 18 days from cell inoculation until necropsy ($Fxyd5^{+/-}$, n=6; $Fxyd5^{-/-}$, n=6). After necropsy, tumor volumes were calculated according to the following formula: tumor volume=length×width$_2$/2. Blood was collected from the abdominal vena cava, stored in EDTA blood collection tubes, and subjected to hematological test using an Exigo Veterinary Hematology Analyzer (Boule Medical, Stockholm, Sweden). Age-matched naïve C57BL/6J mice were used as the control group ($Fxyd5^{-/+}$, n=3; $Fxyd5^{-/-}$, n=3).

11. Protein Isolation and Immunoblot Analysis

Tissues or cells were homogenized in RIPA buffer for 20 min on ice. Protein concentrations were determined based on bicinchoninic acid (BCA) assay using the BCA Protein Assay kit (Thermo Fisher Scientific, Waltham, MA, USA). Proteins were denatured with SDS (Sigma-Aldrich) by boiling at 95° C. for 5 min. Equal amounts of total protein (4-15 μg) were separated by 8% or 10% polyacrylamide gel electrophoresis (PAGE), and separated proteins were transferred to a polyvinylidene difluoride membrane (Millipore, Billerica, MA, USA). Membranes were blocked with 5% bovine serum albumin (Sigma-Aldrich) and incubated overnight at 4° C. with the indicated primary antibodies. Membranes were then incubated with HRP-conjugated secondary antibodies. Chemiluminescence of HRP was developed with ECL reagent (Atto, Tokyo, Japan) and detected with a digital imaging system (ProteinSimple, San Jose, CA). Antibodies used for immunoblot analyses are listed in Table 3.

12. Establishment of Dysadherin-Knockout (KO) or -Overexpressing (OE) Cell Lines A dysadherin-KO ($FXYD5^{-/-}$) SW480 cell line was generated by Transomic Technologies (Huntsville, AL, USA). Specific gRNA targeting different regions of the human FXYD5 gene was designed and cloned into the pCLIPAll (EFS-Puro) expression vector. SW480 cells were infected with lentiviral particles and selected with puromycin for 1 week. Dilution cloning was performed to obtain different monoclonal cell populations. The KO efficiencies of multiple clones were estimated by real-time RT-qPCR and immunoblotting, and a single clone showing the most potent KO efficiency was selected (gRNA sequence: GAGATGGGTCTTACCTC TGG(SEQ ID NO: 99)) and used for further experiments. For establishment of the dysadherin-OE cell line, HCT116 cells were transfected with dysadherin expression vector (pcDNA-L3HSV) and selected with G418 for 1 week. Dilution cloning was performed and OE of the dysadherin gene was confirmed by RT-qPCR and immunoblot analysis. For generation of HCT116 cell lines overexpressing mutant forms of dysadherin, coding sequences were synthesized and cloned into pcDNA™4/HisMax vector by Thermo Fisher Scientific. Vector transfection, stable cell line generation, and validation were performed as described above.

13. Clonogenic Assay

A clonogenic assay was performed as cells were seeded in 12-well plates (200 cells/well) and cultured for 14 days. The numbers of colonies greater than 50 μm in size were counted after staining with crystal violet (n=3/group).

14. Call Growth Assay

Cells were seeded in 6-well or 96-well plates and incubated for various time points. The numbers of viable cells were measured with an automated cell counter (Countess II, ThermoFisher Scientific, Waltham, MA, USA) or measured by staining with thiazolyl blue tetrazolium bromide (MTT, Sigma-Aldrich, St. Louis, MO, USA), and the absorbance was measured using a microplate spectrophotometer (BioTek Instruments Inc., Winooski, VT, USA).

15. Wound Healing Assay

Cells were seeded in culture inserts (Ibidi, GmbH, Martinsried, Germany). Cells were incubated for 48 h (endpoint) after wound scratch. Phase-contrast images of cells were captured using a camera attached to a microscope (Carl Zeiss) at a total magnification of 100×. The wound area at time zero or the endpoint was measured using Image-Pro Premier 9.2. The area of wound closure was calculated as a percentage of the initial wound area. To minimize the effect of differences in cell growth rate, cycloheximide, which inhibits protein synthesis and blocks mitotic entry, was added to the culture media during the period of wound closure.

16. Apoptosis Assay (Annein V+)

The rate of cell apoptosis was quantitatively analyzed by performing apoptosis assays using an Annexin VFluorescein Isothiocyanate (FITC) Apoptosis Detection Kit I (BD Biosciences). Cell suspensions ($1 \times 10_6$/mL) were prepared by washing cells twice with cold PBS. Then, 100 μL of the suspension was transferred to a tube to which 5 μL of FITC, annexin V, and propidium iodide were added. The mixture was incubated at room temperature for 15 min in the dark after gentle vortexing. After incubation, 400 μL of 1× binding buffer was added before analysis using flow cytometry. FACS analysis was performed using a BD Accuri™ flow cytometer (BD Biosciences). FACS data were analyzed using FlowJo software (TreeStar, San Carlos, CA, USA).

17. Boyden Chamber Assay

The Transwell system (8 μm pore size, Corning) was employed for migration and invasion assays. For the migration assay, $3\times10_5$ cells were seeded on the upper chambers in serum-free medium. For the invasion assay, $3\times10_5$ cells were seeded on the upper chamber of a Matrigel-coated Transwell system (8 μm pore size, Corning) in serum-free medium. The bottom chamber was filled with medium supplemented with 20% fetal bovine serum. After incubation for 24 h at 37° C., the cells that migrated or invaded the Matrigel through to the bottom of the insert membrane were fixed, stained with crystal violet, and counted under a phase-contrast microscope (Carl Zeiss, biological triplicates).

18. CRC Xenograft Mouse Model

To compare the tumor-forming potential of empty vector (EV)-transfected control cells and dysadherin-KO cells, an in vivo limiting dilution assay (LDA) was performed. Cells were inoculated s.c. into male NSG mice (NOD.Cg-Prkdc$_{scid}$ Il2rg$_{tm1Wjl}$/SzJ, #005557, Jackson Laboratory, Bar Harbor, ME, USA) at various cell dilutions (50000, 10000, 5000, 1000 cells/mouse, n=6/group). After 56 days, the incidence of tumors in mice was determined by definitive necropsy. LDA graphs were generated, and statistical values were calculated using online software provided by Walter+ Eliza Hall Bioinformatics (http://bioinf.wehi.edu.au/software/elda/). A splenic injection experiment was performed to estimate metastasis and distant organ colonization. In this model, EV-transfected control cells or dysadherin-KO cells were tagged with luciferase and inoculated into the spleens of NSG mice followed by splenectomy ($1\times10^6$ cells/mouse); surviving cells that had migrated out of the spleen and grew in distant organs would then contribute to the formation of liver metastases. We routinely monitored liver metastasis weekly by visualizing luciferase activity for 33 days. After sacrifice, the livers were removed to verify and quantify liver metastasis.

19. Bioinformatics Analyses Using an Open-Source Database

To compare the FXYD5 mRNA expression levels between normal and tumor tissues, gene expression data were obtained from an open-source database (R2: Genomic analysis and visualization platform, https://hgserver1.amc.nl/cgi-bin/r2/main.cgi). The differentially expressed gene (DEG) list was obtained using the R2 platform (GSE21510 dataset) by comparing two groups of patients with CRC (divided according to median dysadherin level; n=52/group). Total DEG lists (p<0.001) were applied as a ranked gene list. The GSEA of the ranked gene list was conducted using the Java implementation of GSEA obtained from http://www.broadinstitue.org/gsea/ (1,000 permutations; minimum term size: 15; maximum term size: 500, C2: all curated genes). The normalized enrichment score accounts for the differences in gene set size. The false discovery rate q-value was used to set the significance threshold.

20. RNA-Sequencing and Ingenuity Pathway Analysis (IPA)

RNA-sequencing was performed to find the altered gene expression signature between dysadherin-KO and control (EV-transfected) SW480 cells. Samples were prepared in biological triplicates, and an RNA-sequencing analysis was performed by LAS science (Seoul, Republic of Korea). Briefly, the mRNA sequencing library was prepared using the TruSeq Stranded mRNA Sample Preparation Kit and the Illumina NextSeq platform. The list of DEGs (n=4,437, p<0.05) altered in dysadherin-KO SW480 cells was subjected to IPA (Qiagen, Redwood City, CA, USA) to identify the potential diseases, functions, and upstream regulators that are significantly associated with dysadherin KO.

21. Identification of Dysadharin-Interacting Proteins

Potential dysadherin-interacting proteins were identified in whole-protein lysates of SW480 cells (KCB Cat #KCB 200848YJ) using M53 monoclonal antibody-based co-immunoprecipitation (co-IP). Incubation with isotype IgG control antibody was used as a negative control. Co-IP proteins were separated by sodium dodecyl sulfatepolyacrylamide gel electrophoresis (SDS-PAGE) and digested in-gel with trypsin. The peptide samples were purified and concentrated by using columns containing C18 reverse-phase resin. The peptides were identified by LC-MS. Raw mass spectrometric data were processed with Sorcerer 2-SEQUEST (Sage-N Research, Milpitas, CA, USA). A list of proteins enriched in the anti-dysadherin co-IP samples versus the IgG control IP samples was obtained by estimating the protein abundance through Top3 TIC method used in Scaffold 4 Q+S program (version 4.6.1, Proteome Software Inc., Portland, OR, USA).

22. Pull-Down Assay for Determination of Direct Protein-Protein Interaction

The coding sequences of wild-type or mutant forms of dysadherin were synthesized and cloned into pET151/ DTOPO vector by Thermo Fisher Scientific. OE of His-tagged dysadherin was achieved using E. coli grown in Luria-Bertani (LB) broth medium, supplemented with ampicillin. Isopropyl β-D-1-thiogalactopyranoside (IPTG, 0.5 mM) was added into the LB broth medium to induce the expression of the protein of interest, and the mixture was incubated for 5 h at 37° C. The cells were then lysed using RIPA buffer and purified using a Ni-NTA column (R90101, Thermo Fisher Scientific). The concentrated purified protein was measured using the BCA Protein Assay kit (Thermo Fisher Scientific). Purified proteins were visualized by separating in 10% SDS-polyacrylamide gels and staining with Coomasie Brilliant Blue. Purified fibronectin protein was purchased from Sigma Aldrich. The mixture of purified His-tagged dysadherin proteins (1 μg) and purified fibronectin protein (0.5 μg) was incubated with anti-His mouse monoclonal antibody (MA1-21315, Thermo Fisher Scientific) at 4° C. overnight. Protein G agarose beads (#37478, Cell Signaling Technology, Beverly, MA, USA) were added and samples were incubated for 6 h at 4° C. After the bead binding step, samples were centrifuged and the pellets were boiled in 3×SDS-PAGE loading buffer for immunoblotting. Presence of His-tagged dysadherin and fibronectin proteins were determined by immunoblot analysis using anti-His rabbit monoclonal antibody (#12698, Cell Signaling Technology) and anti-fibronectin rabbit polyclonal antibody (ab2413, Abcam, Cambridge, MA, USA). Pull-down assays of peptides were performed using Ni-NTA agarose beads (R90101, Thermo Fisher Scientific). His-tagged dysadherin protein was purchased from Abcam (ab140573) and peptides were synthesized by ANYGEN (Cheongju, Republic of Korea). The purity of each peptide was determined to be over 95% by LC-MS. The mixtures of purified fibronectin protein (0.5 μg, Abcam, F2006) and His-tagged dysadherin proteins (2 μg) or peptides (20 μg) were incubated in 500 μL of buffer containing 50 mM $NaH_2PO_4$ (pH 7.4), 250 mM NaCl, and 10 mM imidazole for 1 h on ice, followed by the addition of 15 μL of Ni-NTA agarose beads (R90101, Thermo Fisher Scientific) with end-to-end rotation for 1 h at 4° C. The beads were precipitated by centrifugation at 2,000×g for 3 min and then washed five times with 500 μL of binding buffer containing 30 mM imidazole. The beads were boiled in 3×SDS-PAGE loading buffer, and the proteins were separated by 15% SDS-PAGE. The presence of His-tagged dysadherin, dysadherin peptides, and fibronectin was determined by staining with Coomassie Brilliant Blue.

23. Collagen Gel Contraction Assay

CRC cells ($1\times10_6$ cells) were embedded in 1 mL collagen-I, yielding a final collagen I concentration of 1.5 mg/mL, and seeded in 12-well plates. When performing the gel contraction assay, the wells were pre-coated with 1% bovine serum albumin. We used high-concentration Corning collagen-I purified from rat tail (#354249). After 1 h of gelation at 37° C., the cells were washed once in normal medium for 1 h and reimmersed in fresh medium. The gel contraction was monitored after 48 h by taking photographs of the gels. The percentage of gel contraction was quantified using the formula: percentage gel contraction=100×((well areal-gel area)/well area)). To normalize the data points, we generated a contractile index using the formula: contractile index= (percentage gel contraction$_{perturbation}$/percentage gel contraction$_{control}$). Thus, an increase in the contractile index is an increase in contraction.

24. Statistical Analyses

All results are expressed as the mean±standard error of the mean. Statistical comparisons of data from 2 groups were carried out by Student's t-test or two-way ANOVA with the Bonferroni multiple comparison test, and statistical comparisons of 3 or more groups were carried out by one-way ANOVA with the Dunnett's multiple comparison test using GraphPad Prism (GraphPad Software Inc, San Diego, California, USA). The log-rank test was used for Kaplan-Meier analysis using SPSS version 21.0 (IBM Corp., Armonk, NY, USA). Asterisks are used to indicate statistical significance. *, , and * indicate p<0.05, <0.01, and <0.001, respectively.

Results

1. Deletion of Dysadherin Attenuates Intestinal Tumorigenesis

Figure 1F:
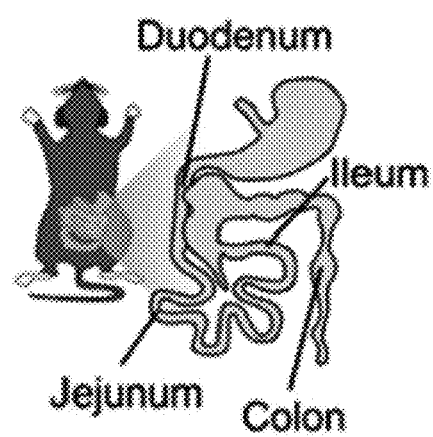
Figure 1F:
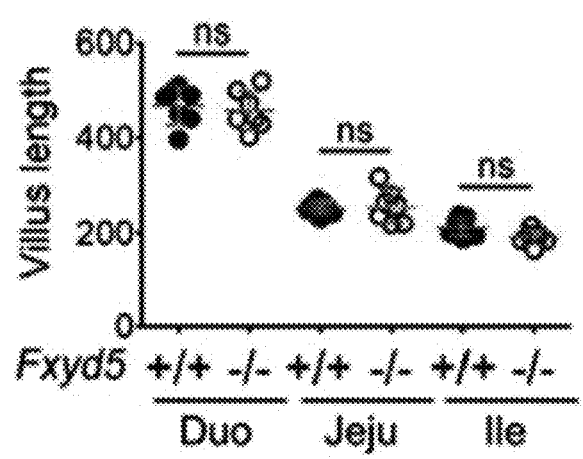
Figure 1G:
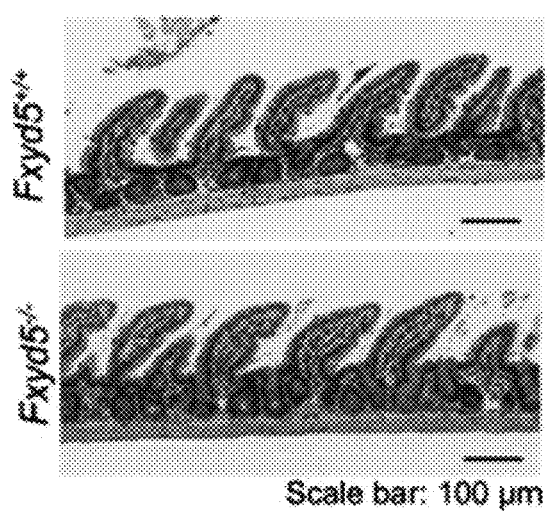
Figure 1G:
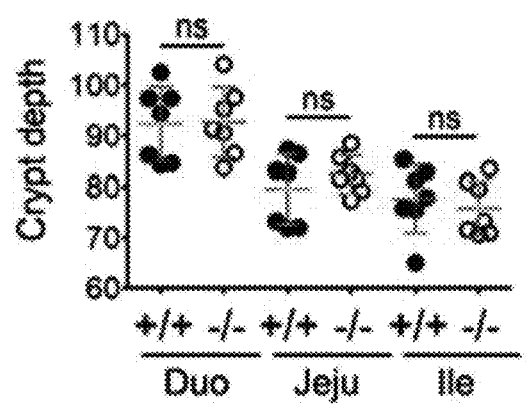
Figure 2A:
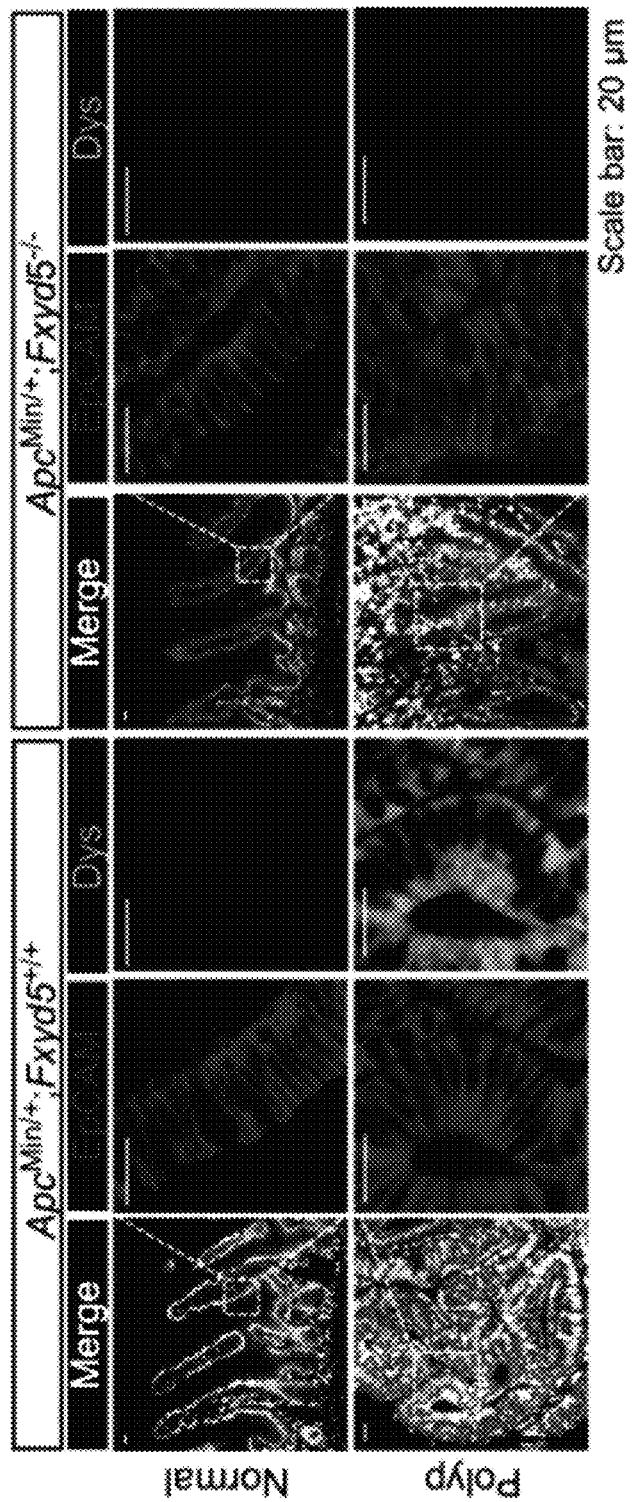
FIGS. 2A-2F illustrate dysadherin deficiency inhibits intestinal tumorigenesis.
Figure 2B:
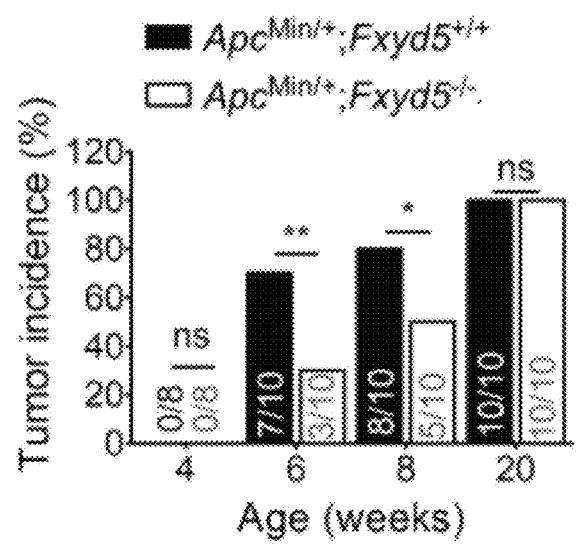
Figure 2C:
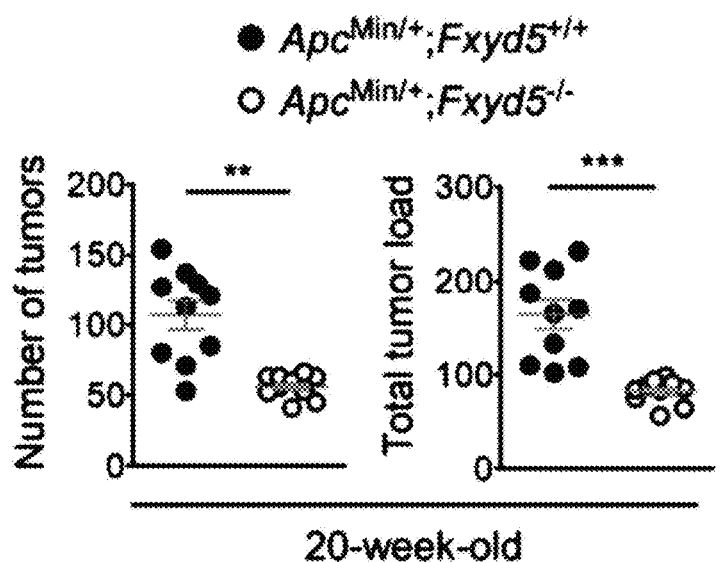
Figure 2D:
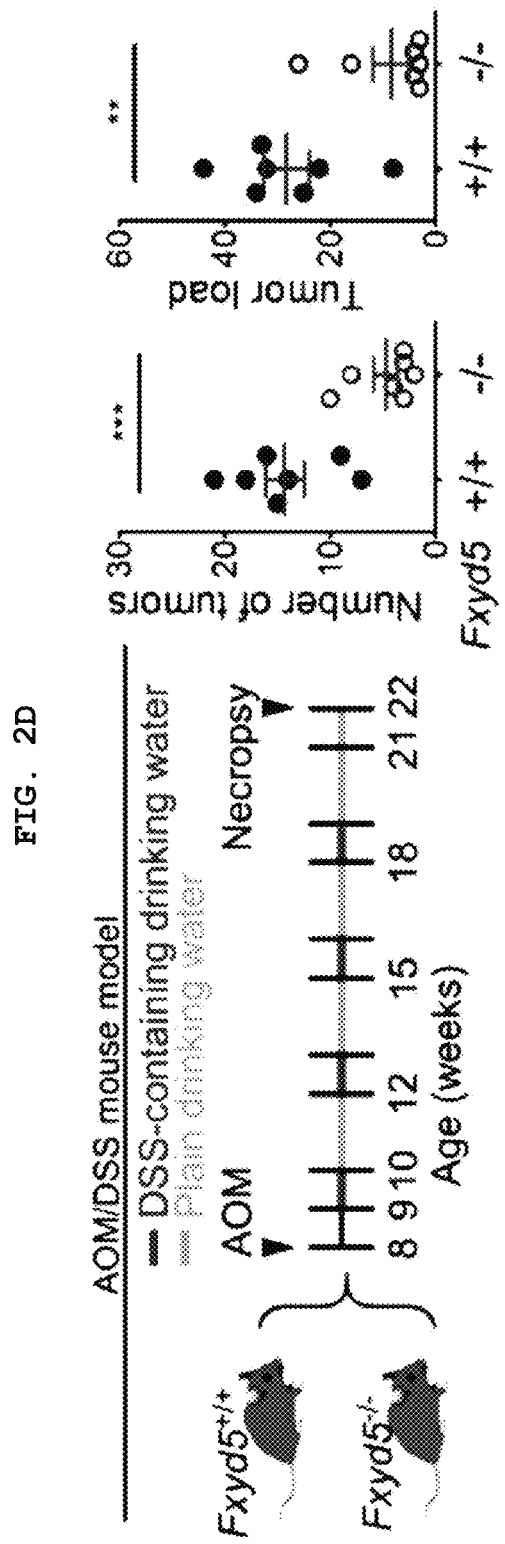
Figure 3A:
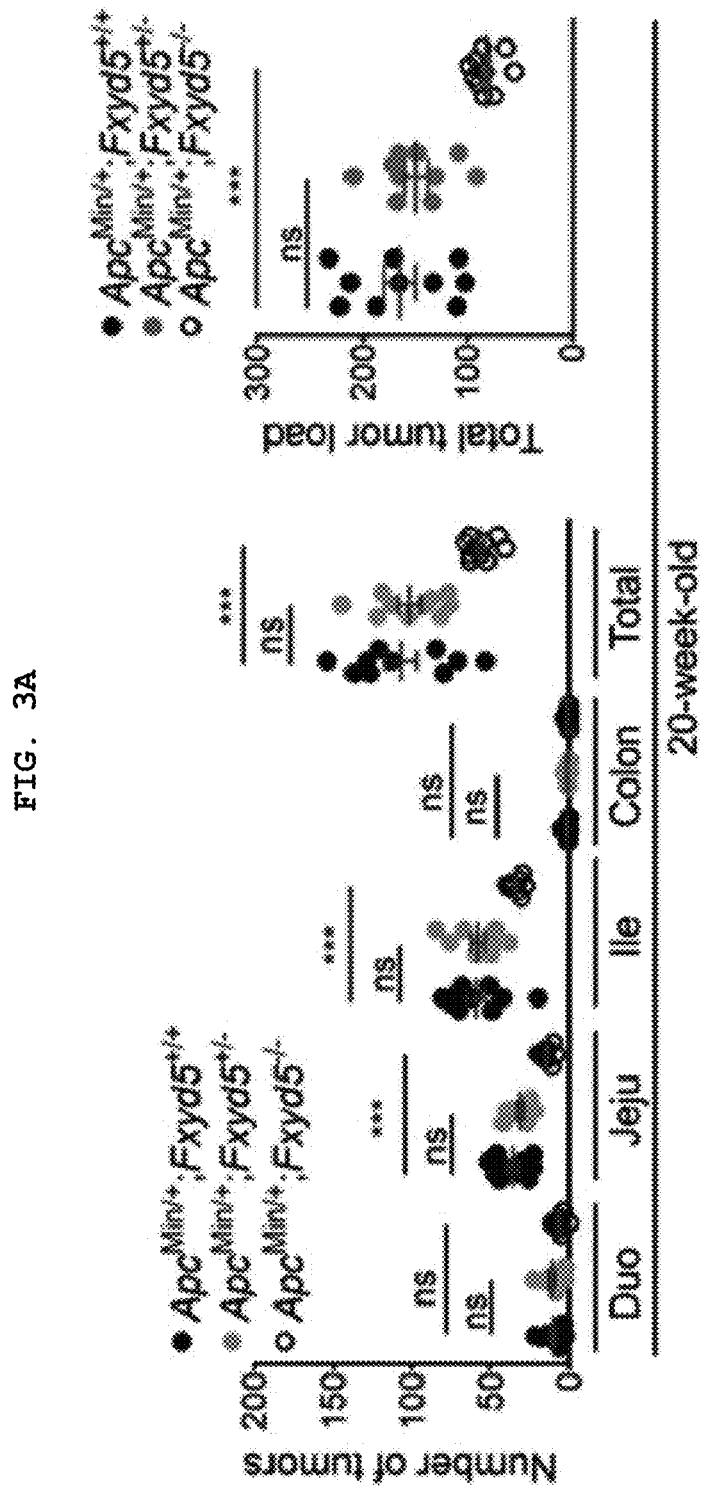
FIGS. 3A-3E illustrate the impact of dysadherin deficiency on intestinal tumorigenesis in Apc$^{Min/+}$ mice and AOM/DSS treated mice.
Figure 3B:
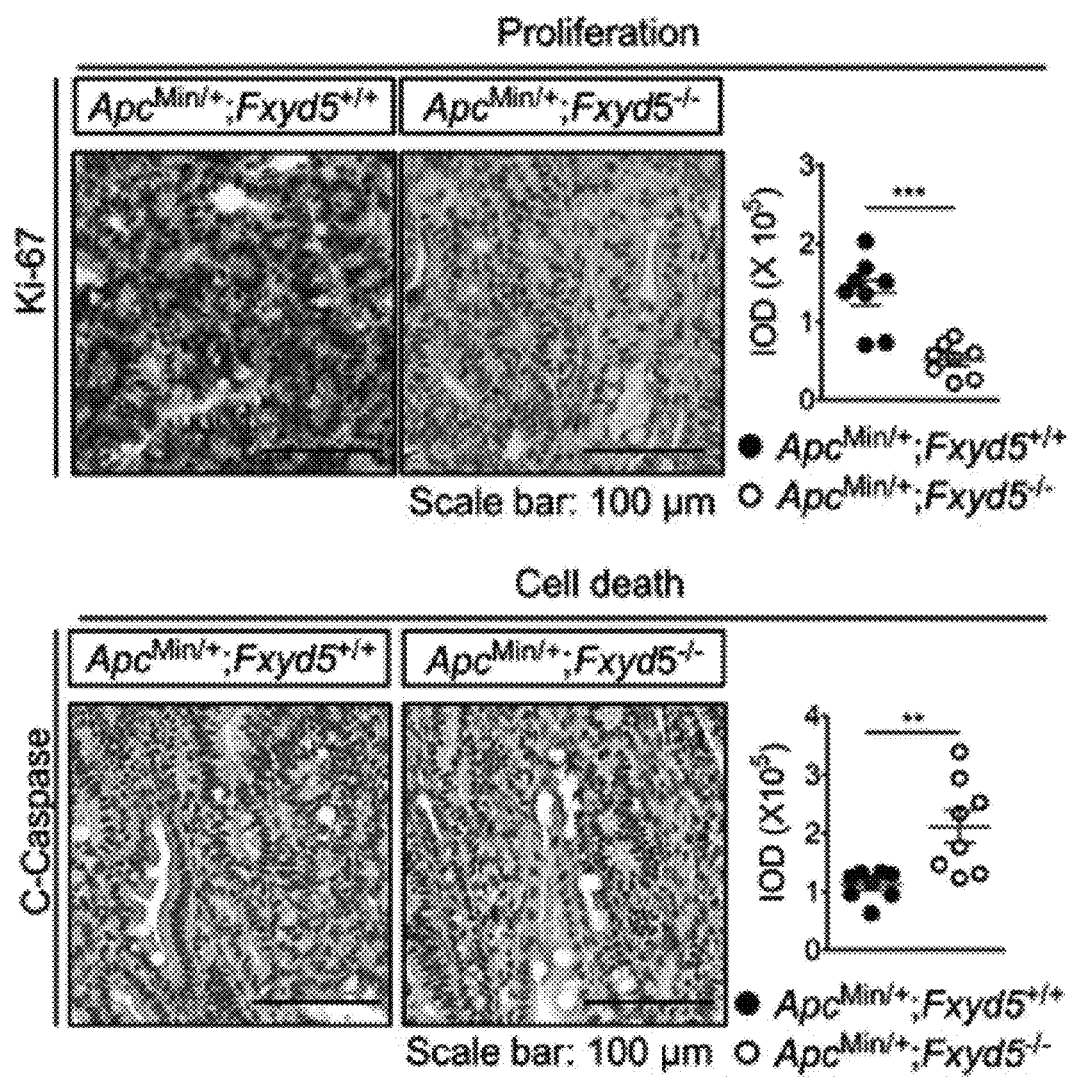
Figure 3C:
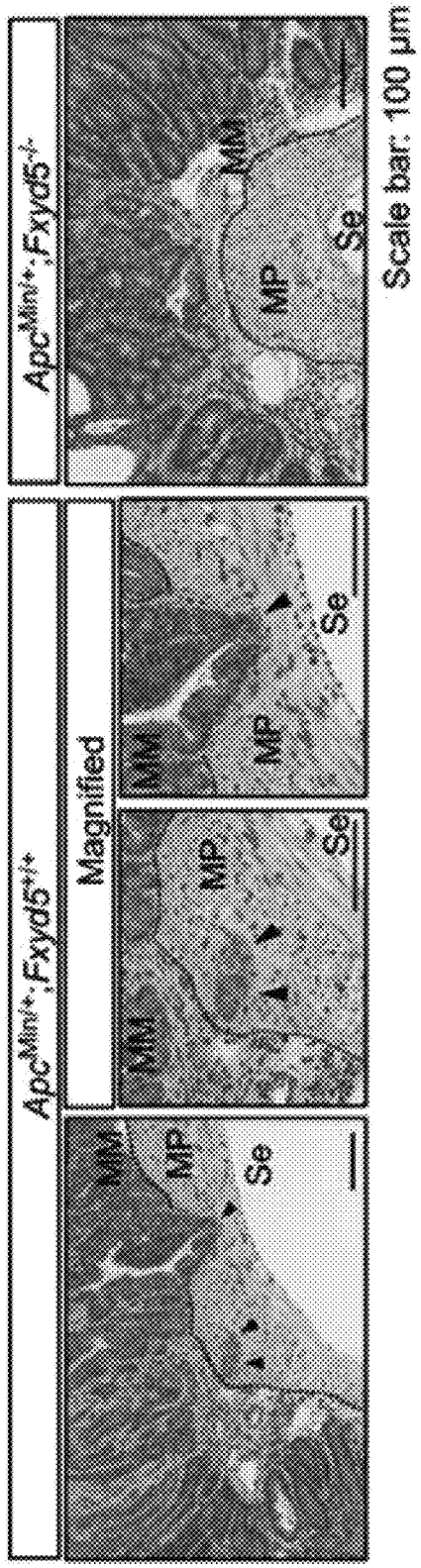
Figure 3D:
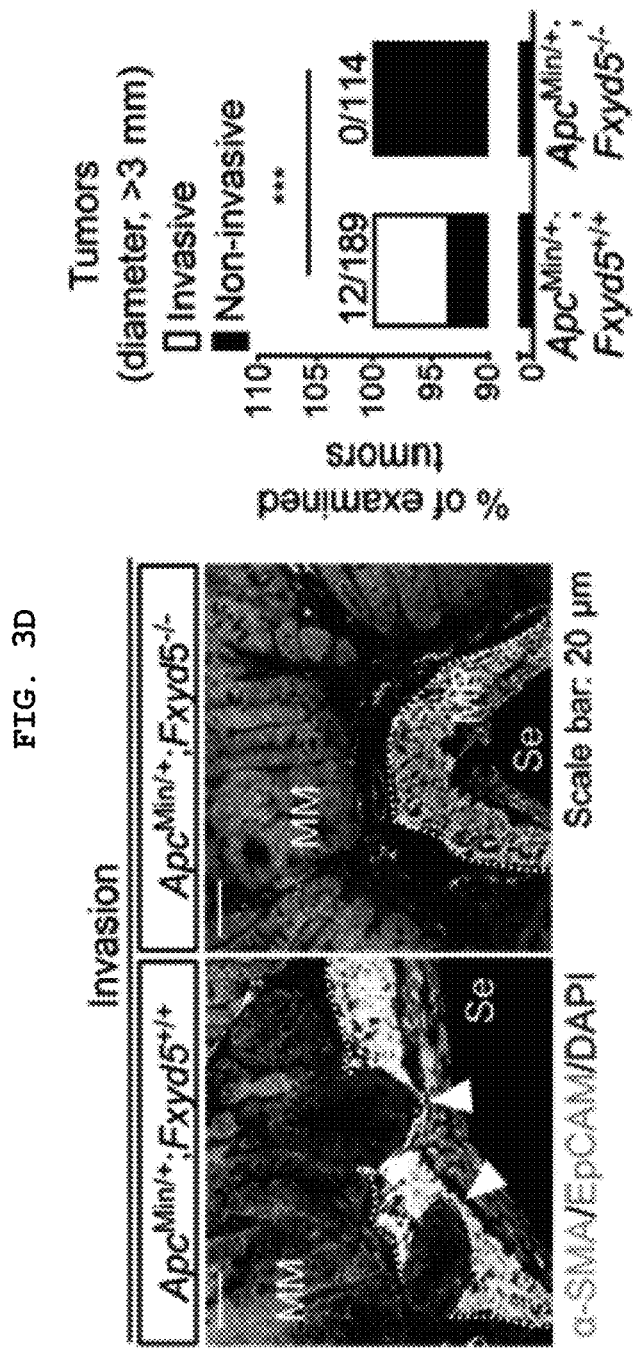
Figure 3E:
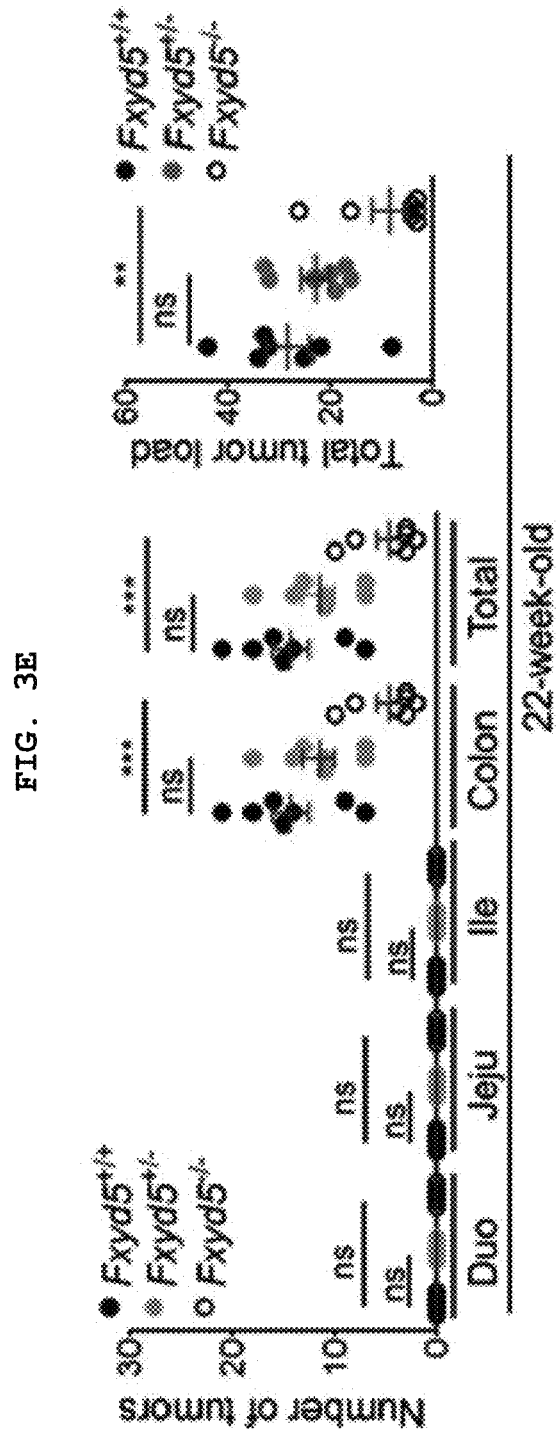

To verify the role of dysadherin in intestinal tumorigenesis, we established dysadherin-KO (Fxyd5$^{-/-}$) mice by deleting exons 2-7 of Fxyd5 with CRISPR/Cas9 technology (FIGS. 1A-1D). Fxyd5$^{-/-}$ mice were viable without any discernible phenotype, were born at a Mendelian ratio (FIG. 1E), and did not present with any intestinal abnormalities (FIGS. 1F-1G). In the Apc$^{Min/+}$ mouse model, histological assessment of Apc$^{Min/+}$ mice revealed the acquisition of dysadherin expression in epithelial cell adhesion molecule-positive (EpCAM.) epithelial cells residing within intestinal tumors, whereas no dysadherin expression was observed in epithelial cells within normal intestines (FIG. 2A). The complete absence of dysadherin expression in the intestinal tumor epithelium of Apc$^{Min/+}$;Fxyd5$^{-/-}$ mice was confirmed (FIG. 2A). Of note, dysadherin deletion did not completely block Apc$^{Min/+}$-driven intestinal tumorigenesis but delayed tumor development, as indicated by a decrease in tumor incidence in younger mice (6- and 8-week-old; FIG. 2B). Consistently, in older (20-week-old) mice, the number of tumors and total tumor load were significantly decreased by dysadherin deletion (FIG. 2C and FIG. 3A). Further histological analyses showed a reduction in cell proliferation and an increase in cell death in dysadherin-deficient tumor cells (Supplementary FIG. 3B). Approximately 6.3% of tumors from the 20-week-old Apc$^{Min/+}$ mice showed local invasion through a fissure of the mucosal muscle layer; however, all tumors in the Apc$^{Min/+}$;Fxyd5$^{-/-}$ mice remained above the mucosal muscle layer and thus presented with a noninvasive phenotype (FIGS. 3C,3D). In the azoxymethane/dextran sodium sulfate (AOM/DSS)-induced intestinal tumorigenesis mouse model, dysadherin deletion also significantly reduced both the number of tumors and total tumor load (FIG. 2D and FIG. 3E), suggesting that dysadherin expression contributes to intestinal tumorigenesis in both the genetically and chemically induced mouse models of intestinal cancer.

Figure 4A:
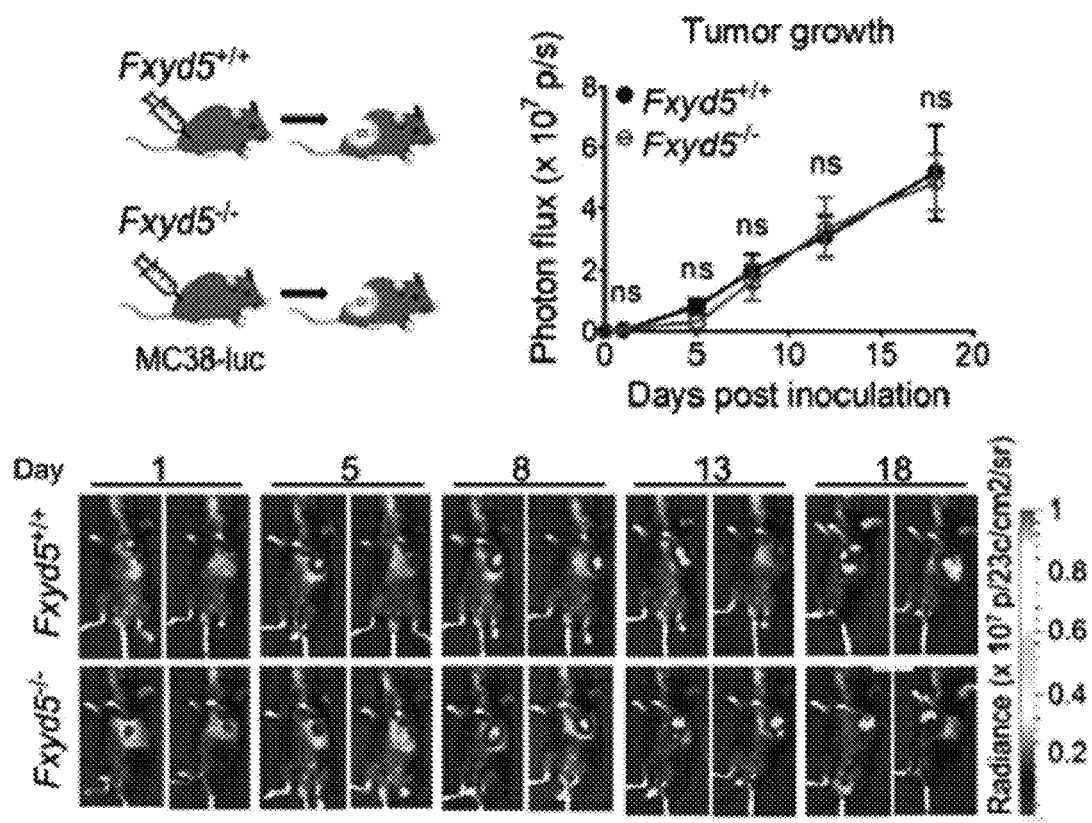
Figure 4B:
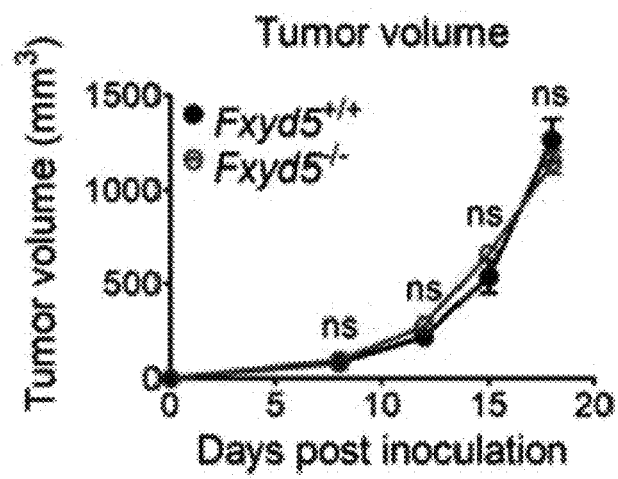
Figure 4C:
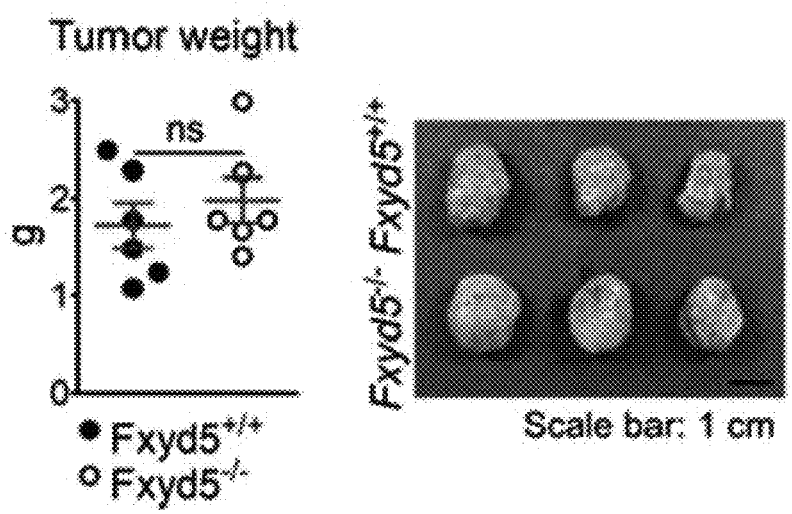
Figure 4E:
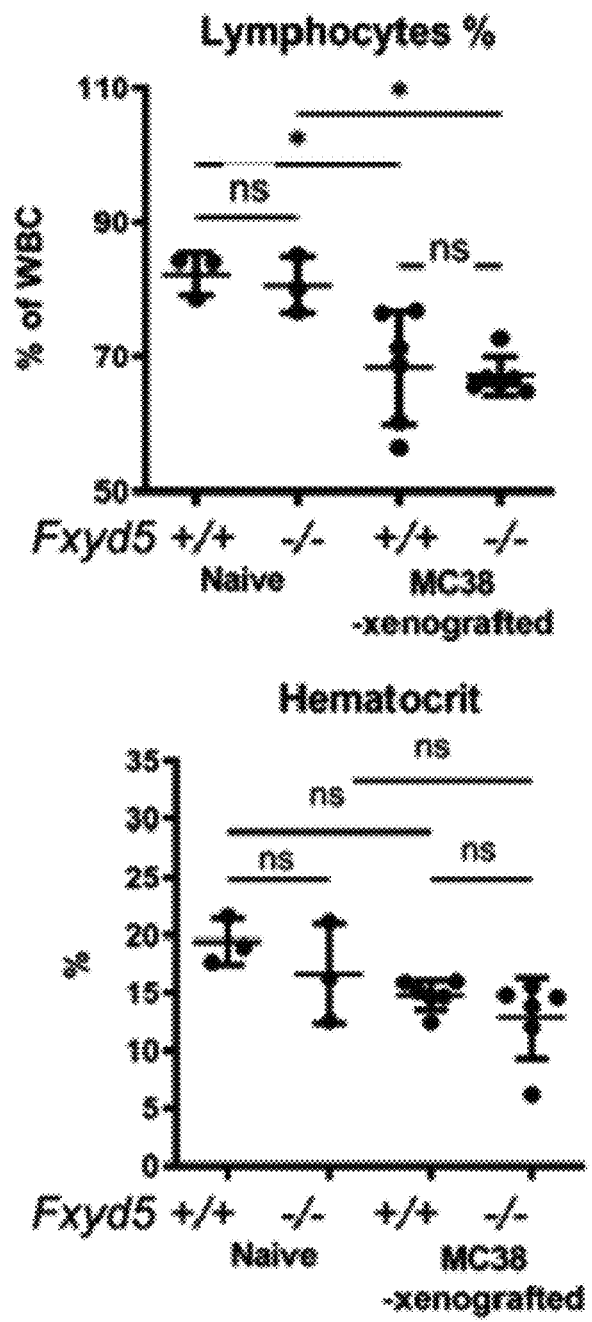
Figure 4F:
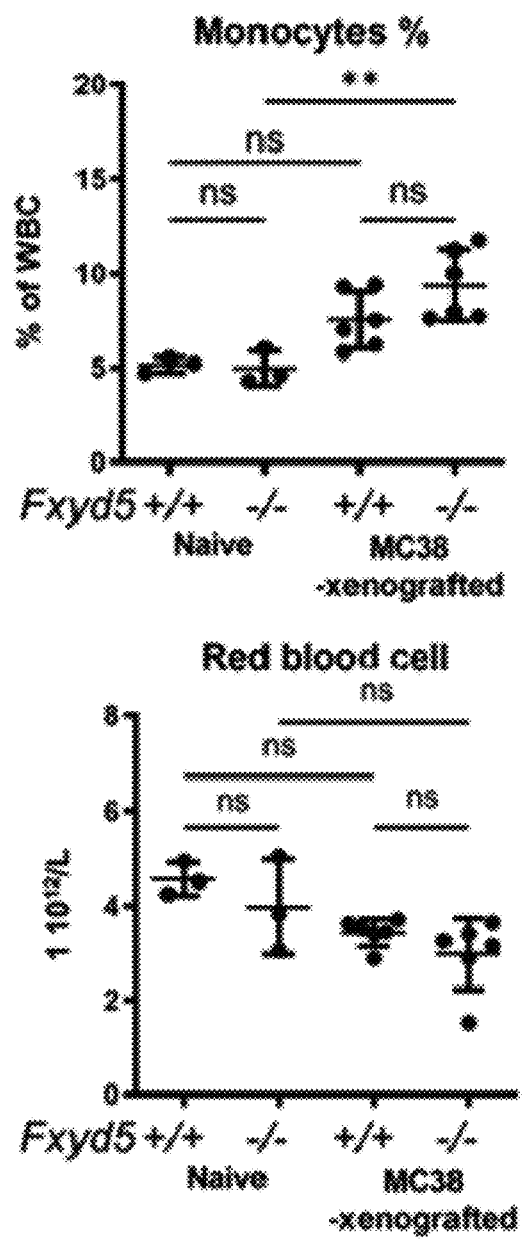
Figure 4G:
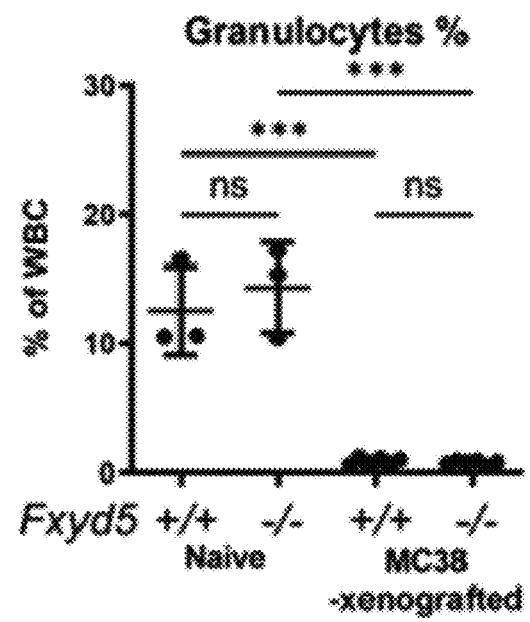
Figure 4G:
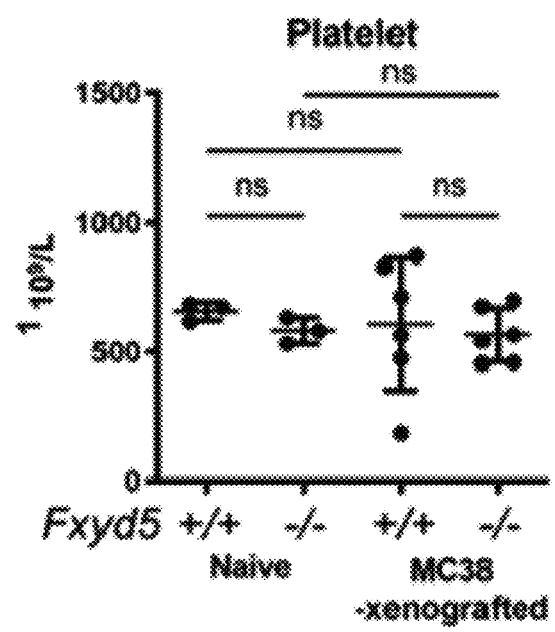
Figure 5A:
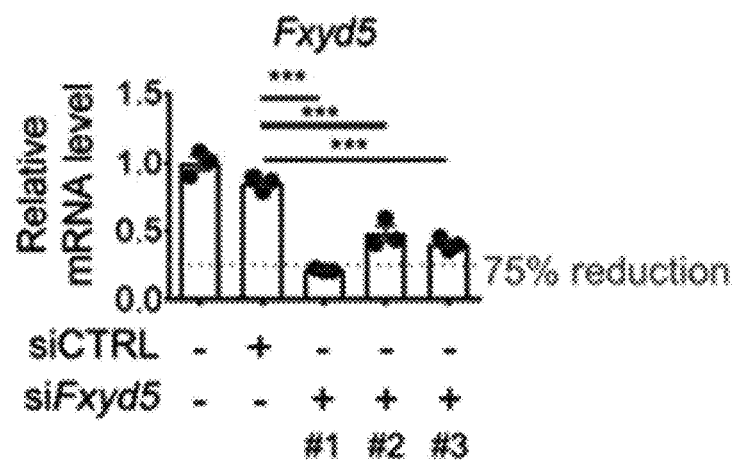
FIGS. 5A-5B illustrate validation of siRNA efficacy using MC38 cells and intestinal tumoroids derived from Apc$^{Min/+}$ mice.
Figure 5B:
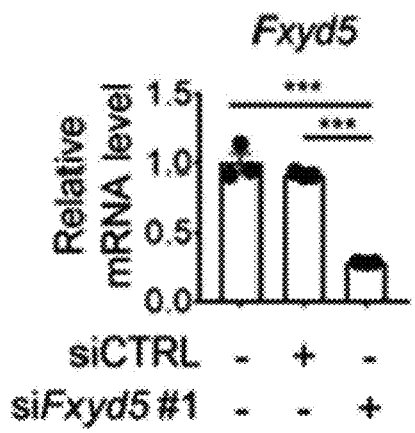

Conversely, when we explored the stromal effect of dysadherin depletion on tumorigenesis by inoculating murine intestinal tumor cells (MC38) into Fxyd5$^{+/-}$ and Fxyd5$^{-/-}$ mice, we found that dysadherin-KO physiological environment did not affect tumor seeding and growth (FIGS. 4A-4C). Additionally, blood analyses did not show hematological differences between Fxyd5$^{+/+}$ and Fxyd5$^{-/-}$ mice (FIGS. 4D-4G). Although these data cannot completely exclude the potential role of dysadherin in stromal cellular compartments during tumorigenesis, they inspired us to focus on the role of dysadherin in tumor epithelial cells in further mechanistic studies. Moreover, the majority of CRC cells are known to originate from the intestinal epithelial cells of the colorectal mucosa that acquire advantages of clonal growth and expansion during tumor development. Thus, to validate the effect of dysadherin deficiency on the growth of the tumor epithelium, we cultured intestinal tumoroids derived from the polyps of 20-week-old Apc$^{Min/+}$ mice and silenced dysadherin expression using siRNAs. First, we tested the effectiveness of siRNAs targeting mouse dysadherin (siFxyd5) in MC38 cells and chose the most effective sequence (FIGS. 5A,5B). We found that dysadherin silencing significantly suppressed the growth of intestinal tumoroids (FIGS. 2E,2F), confirming the importance of acquired dysadherin expression during growth of tumor epithelium.

Figure 6A:
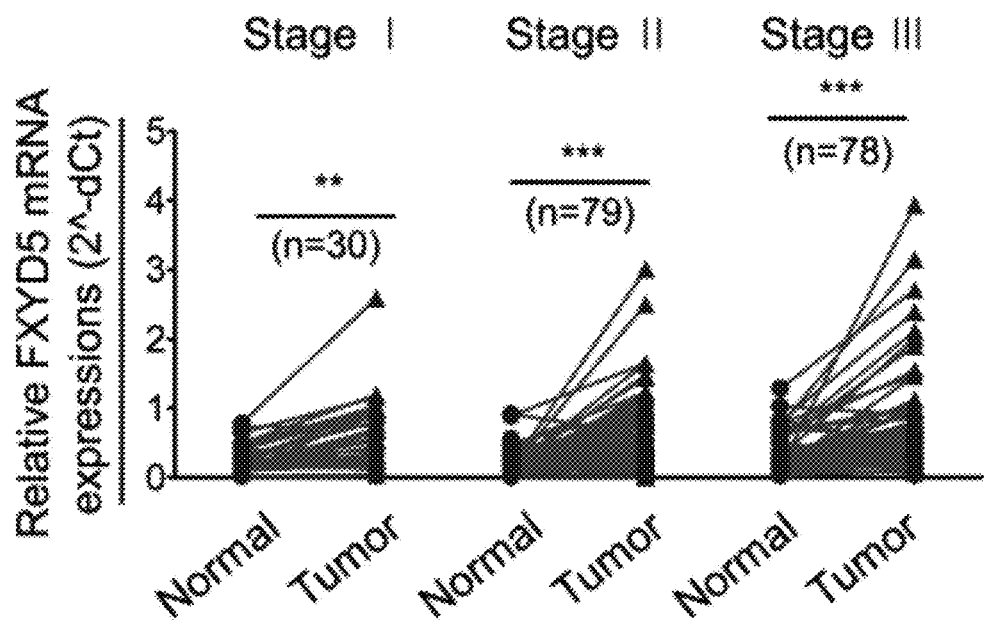
FIGS. 6A-6H illustrate clinical implications of dysadherin expression in CRC patients and it pleiotropic role within CRC cells.
Figure 6B:
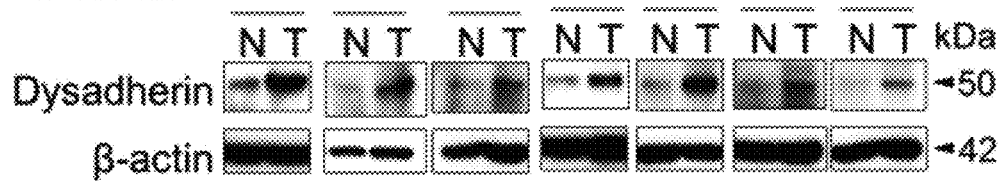
Figure 6C:
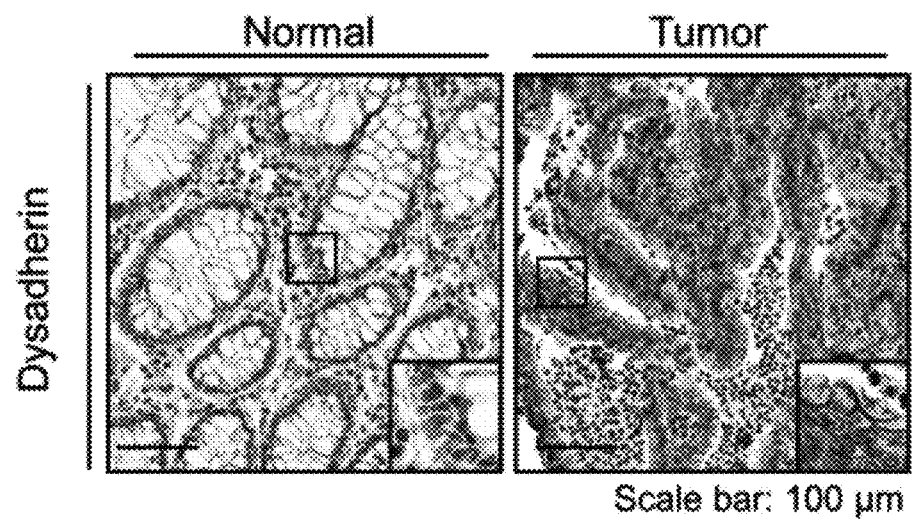
Figure 6D:
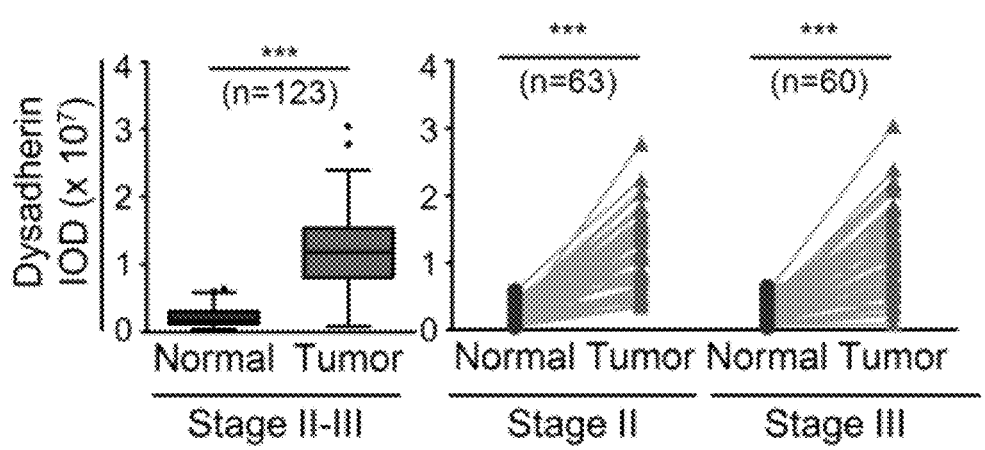
Figure 6E:
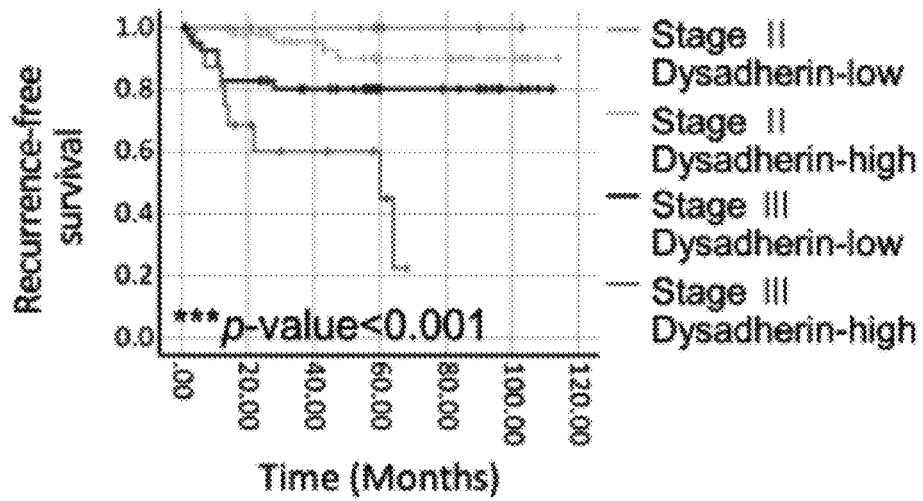
Figure 6F:
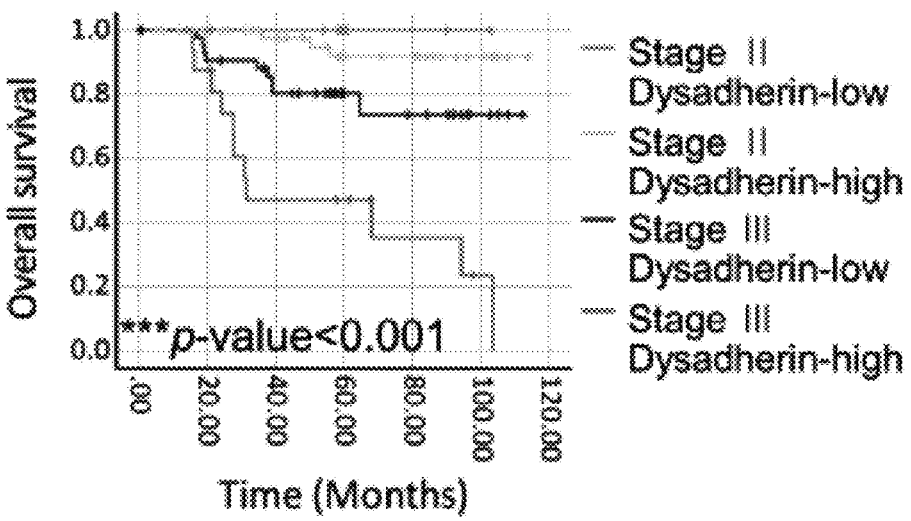
Figure 7:
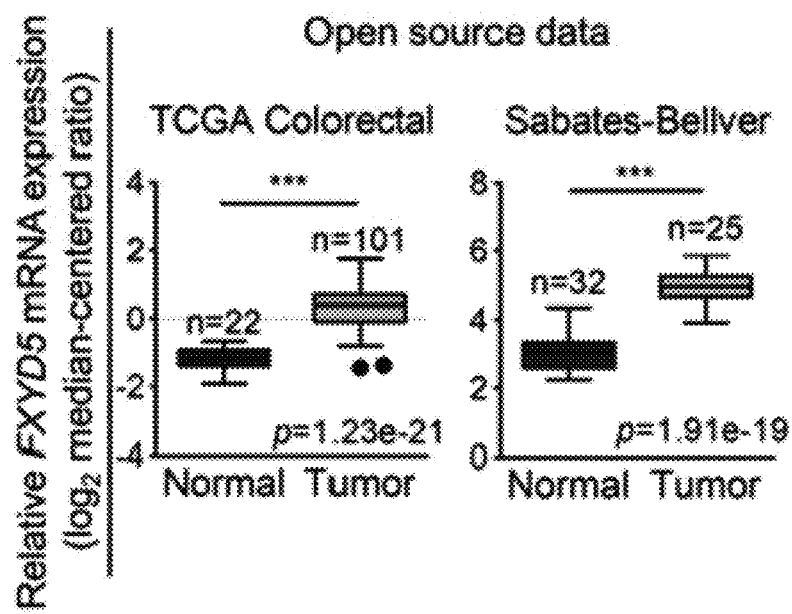
FIG. 7 illustrate evaluation of dysadherin expression in CRC patients. mRNA expression data obtained from an opensource database (R2: Genomic analysis and visualization platform) showing FXYD5 expression in normal tissues and tumor tissues. Box plots display the median values with upper and lower quartiles, and Tukey whisker plots show the ranges. Statistical significance was determined by non-paired Student's t-tests.

Consistent with the mouse experiments, our clinical investigation of 187 patients with CRC revealed an increase in dysadherin at both the mRNA and protein levels in tumor tissues versus matched normal tissues (FIGS. 6A,6B). Analysis of an open-source genomic database (R2) further confirmed the increase in dysadherin mRNA levels in tumors of CRC patients (FIG. 7). Histopathological analyses of tissues from 123 patients with CRC confirmed that dysadherin was not expressed in the normal epithelium, but its expression was increased in the tumor epithelium (FIGS. 6C,6D). Interestingly, the extent of the increase in dysadherin expression in the tumor epithelium was significantly correlated with tumor T stage and recurrence (Table 4), and dysadherin expression was an independent and significant prognostic marker of poor clinical outcomes, short OS and RFS in patients with CRC (FIGS. 6E,6F).

TABLE 4

| Variable | Dysadherin expression | | p-value |
|---|---|---|---|
| | Low (<75%, n = 96) | High (≥75%, n = 27) | |
| Age (mean ± SD) | 64.7 ± 9.92 | 67.3 ± 9.03 | 0.362 |
| Sex | | | |
| Male | 57 (59.4%) | 14 (51.9%) | 0.484 |
| Female | 39 (40.6%) | 13 (48.1%) | |

TABLE 4-continued

| Variable | Dysadherin expression | | p-value |
|---|---|---|---|
| | Low (<75%, n = 96) | High (≥75%, n = 27) | |
| T stage | | | |
| T2-3 | 86 (89.6%) | 19 (70.4%) | 0.013 |
| T4 | 10 (10.4%) | 8 (29.6%) | |
| N Stage | | | |
| N0 | 52 (54.2%) | 11 (40.7%) | 0.435 |
| N1 | 27 (28.1%) | 9 (33.3%) | |
| N2 | 17 (17.7%) | 7 (25.9%) | |
| TNM stage | | | |
| II | 52 (54.2%) | 11 (40.7%) | 0.218 |
| III | 44 (45.8%) | 16 (59.3%) | |
| Tumor differentiation | | | |
| Well | 33 (34.4%) | 8 (29.6%) | 0.770 |
| Moderately | 56 (58.3%) | 16 (59.3%) | |
| Poorly | 7 (7.3%) | 3 (11.1%) | |
| LVI | | | |
| Positive | 19 (19.8%) | 9 (33.3%) | 0.138 |
| Negative | 77 (80.2%) | 18 (66.7%) | |
| PNI | | | |
| Positive | 43 (44.8%) | 17 (63.0%) | 0.095 |
| Negative | 53 (55.2%) | 10 (37.0%) | |
| Recurrence | | | |
| Yes | 12 (12.5%) | 8 (29.6%) | 0.033 |
| No | 84 (87.5%) | 19 (70.4%) | |

Multivariate Cox analysis (low dysadherin group vs. high dysadherin group)
OS (II + III): HR 3.863 (95% CI, 1.698-8.792), p = 0.002
RFS (II + III): HR 2.569 (95% CI, 1.046-6.308), p = 0.040

2. Dysadherin Plays a Pleiotropic Role in CRC Calls

Figure 2E:
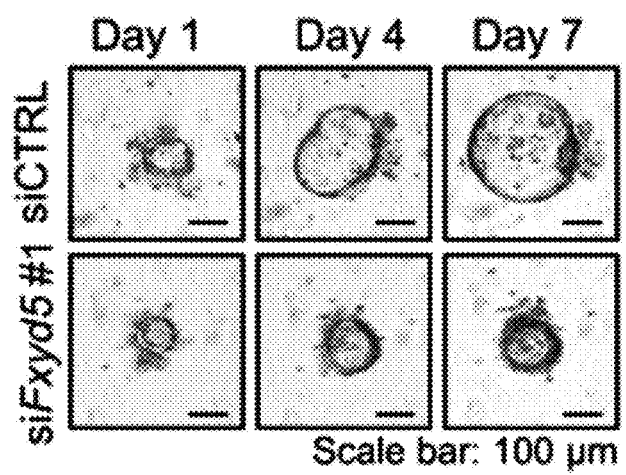
Figure 2F:
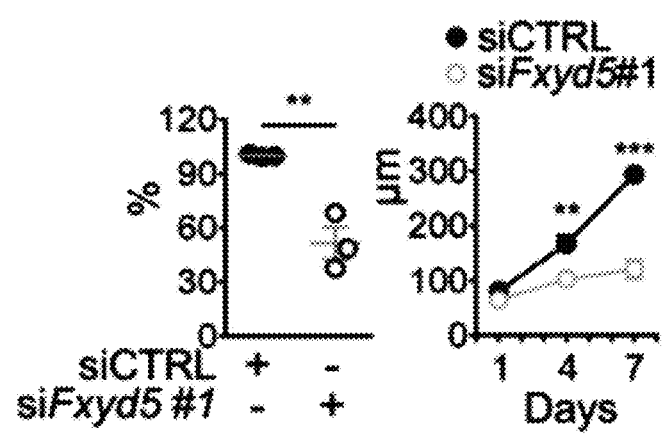
Figure 6G:
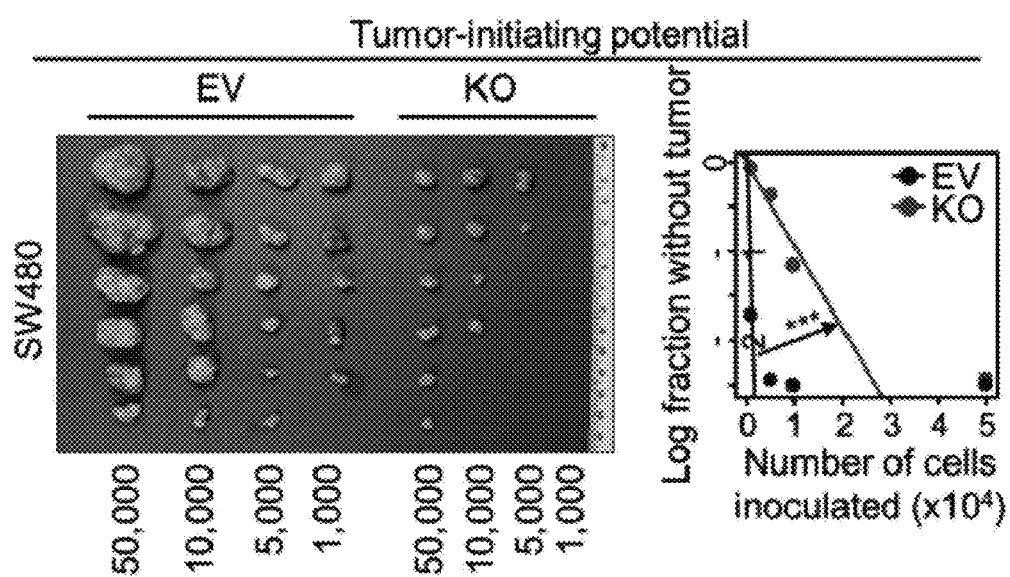
Figure 6H:
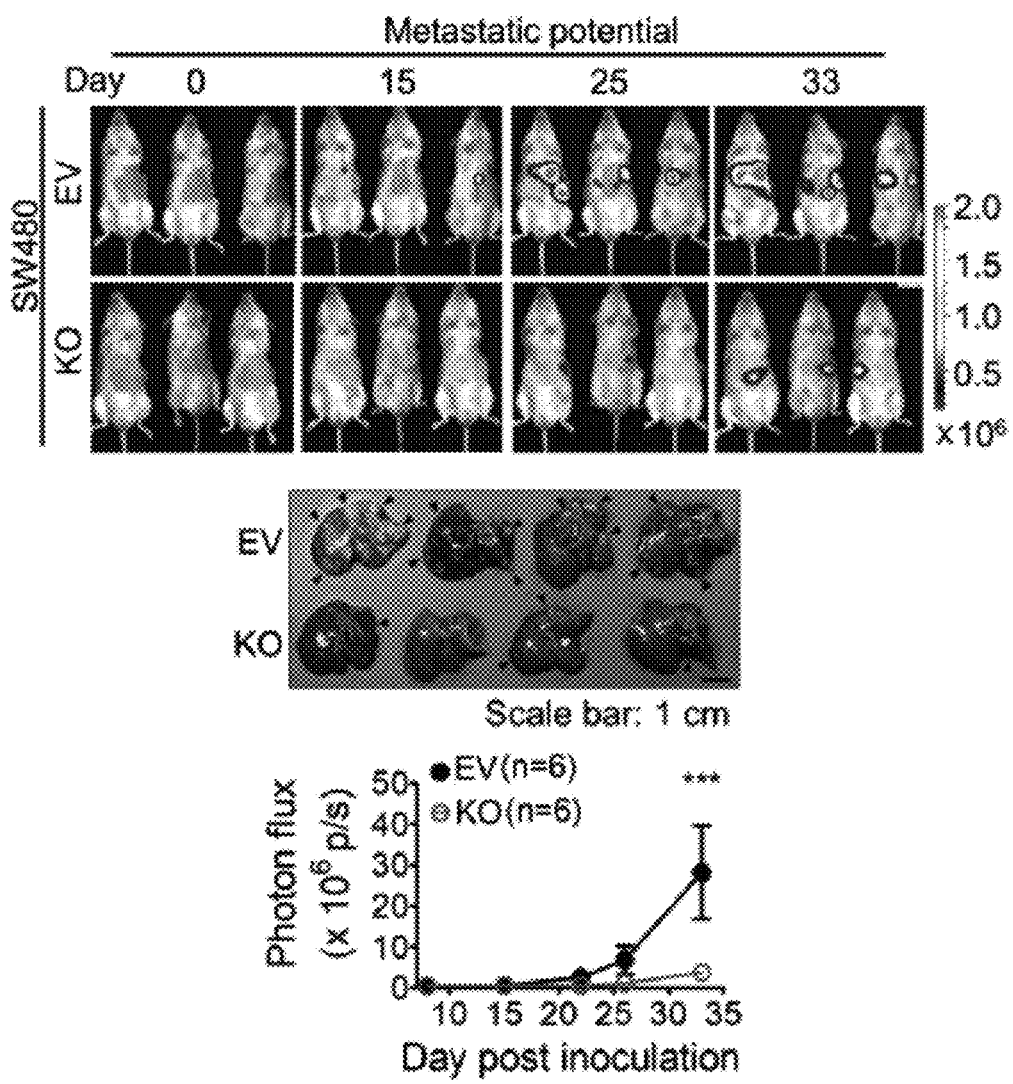
Figure 8A:
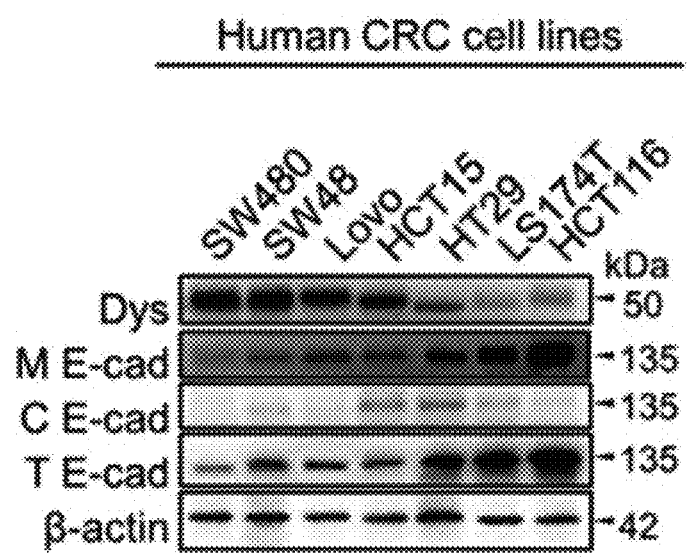
FIGS. 8A-8F illustrate effect of dysadherin expression on CRC cell behavior including cell growth, survival, apoptosis, migration, and invasion potential.
Figure 8B:
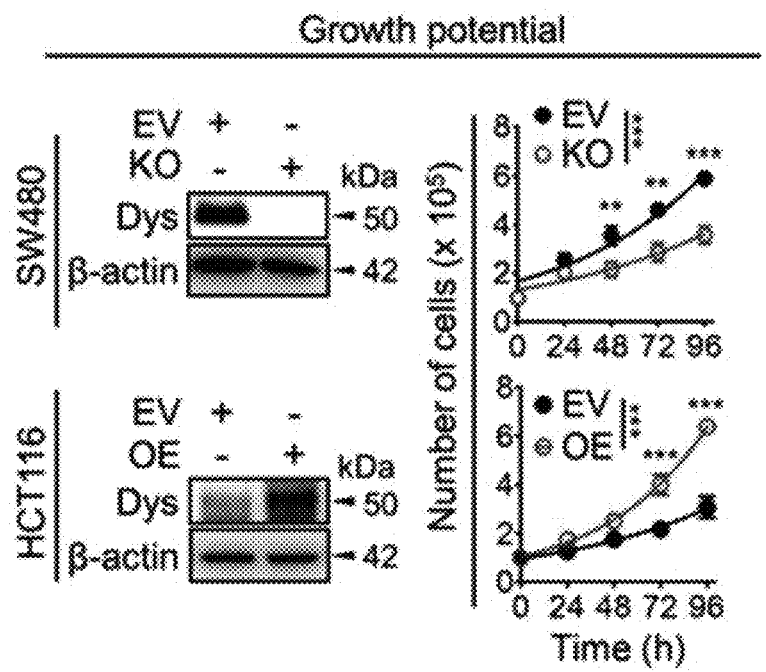
Figure 8C:
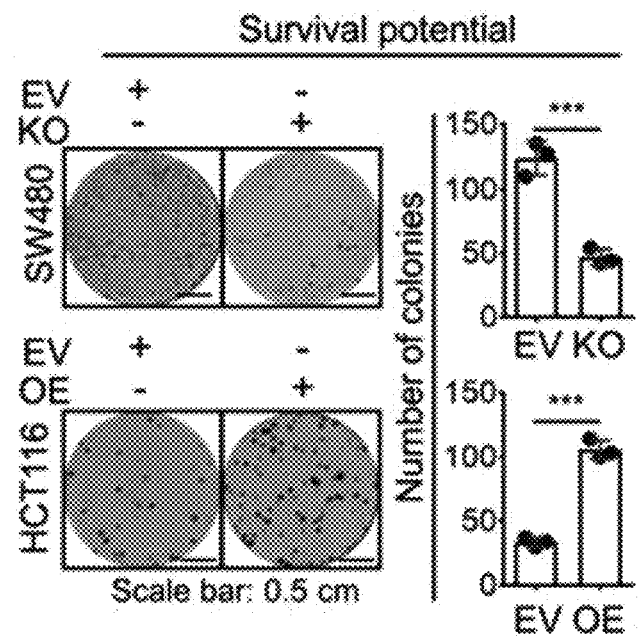
Figure 8D:
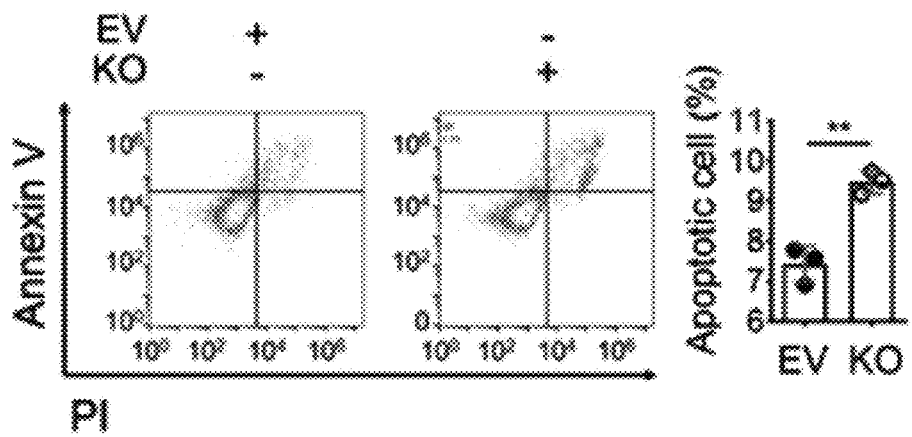
Figure 8D:
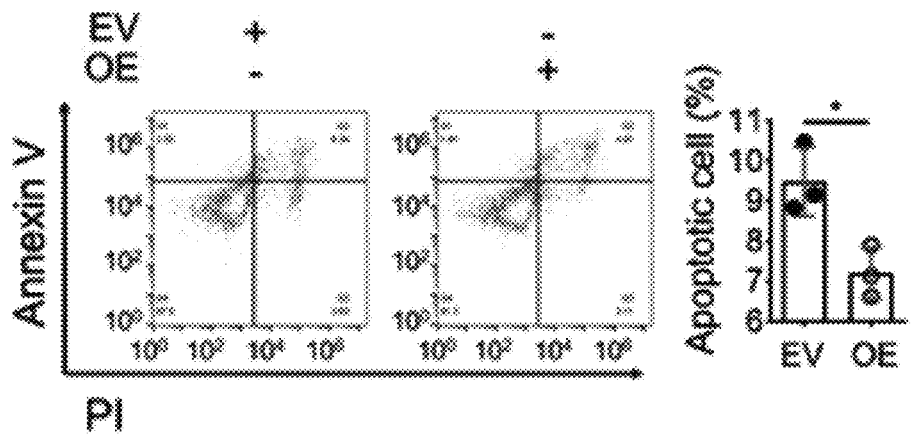
Figure 8E:
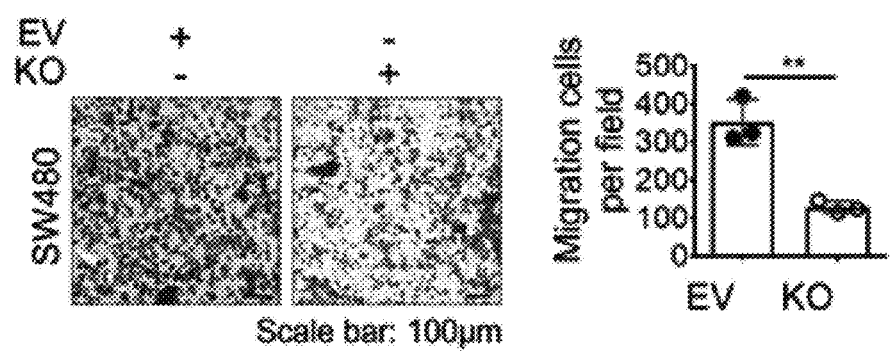
Figure 8E:
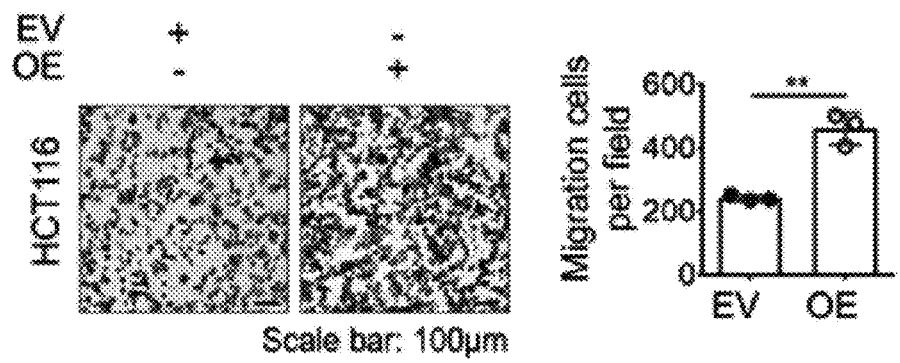
Figure 8F:
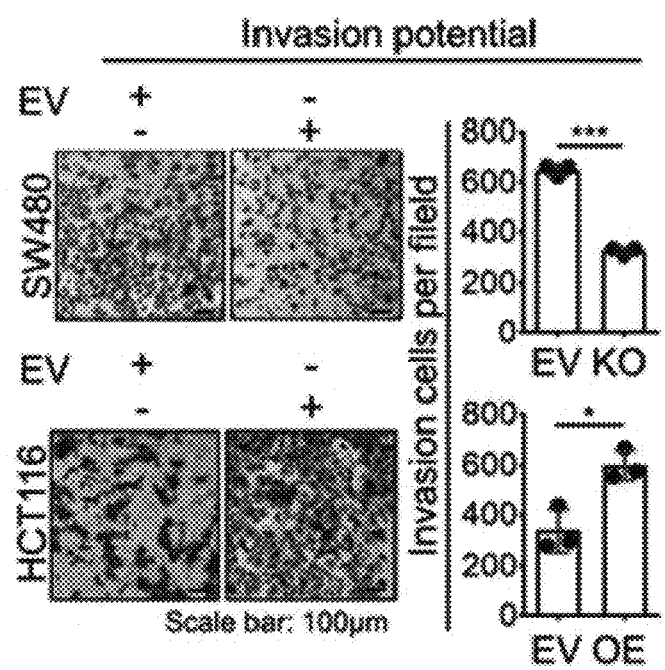

The combination of increased dysadherin expression and reduced E-cadherin expression is known to reflect tumor aggressiveness and is considered to be a prognostic marker of poor clinical outcomes in patients with a broad range of cancers. Consistent with these clinical observations, immunoblot analysis of a human CRC cell line panel showed a significant tendency towards increased dysadherin expression and decreased membrane E-cadherin expression (FIG. 8A). For our mechanistic study, we deleted dysadherin in SW480 cells, which express the highest levels of dysadherin among CRC cell lines. We also overexpressed dysadherin in HCT116 cells, which express the lowest levels of dysadherin. Dysadherin KO attenuated the growth of SW480 cells, and dysadherin OE promoted the growth of HCT116 cells (FIG. 8B). In clonogenic assays, dysadherin KO reduced the survival potential of SW480 cells, whereas dysadherin OE increased the survival potential of HCT116 cells (FIG. 8C). Also, apoptosis was increased upon dysadherin deletion and reduced upon dysadherin OE (FIG. 8D), consistent with our previous observations in breast and liver cancer cells. Moreover, Boyden chamber assays with or without Matrigel coating revealed that dysadherin OE promotes the invasive and chemotactic migration of CRC cells, whereas dysadherin KO suppresses these aggressive phenotypes (FIGS. 8E,8F). Next, we examined the in vivo function of dysadherin in CRC xenograft mouse models. A limiting dilution assay confirmed the reduction in the tumor-initiating potential of CRC cells upon dysadherin deletion (FIG. 6G). This result may reflect that dysadherin plays a critical role in determining the tumorigenic capacity of CRC cells, as observed in genetically and chemically induced CRC mouse models (FIGS. 2B-2D). In addition, a splenic injection mouse model confirmed that dysadherin deficiency reduced the metastatic potential of injected CRC cells to the liver (FIG. 6H). Collectively, these data suggest that dysadherin expression is required for diverse processes in CRC cells, including growth, survival, migration, and invasion.

3. The ECM-Integrin Pathway is a Key Dysadharin Signaling Pathway

Figure 9A:
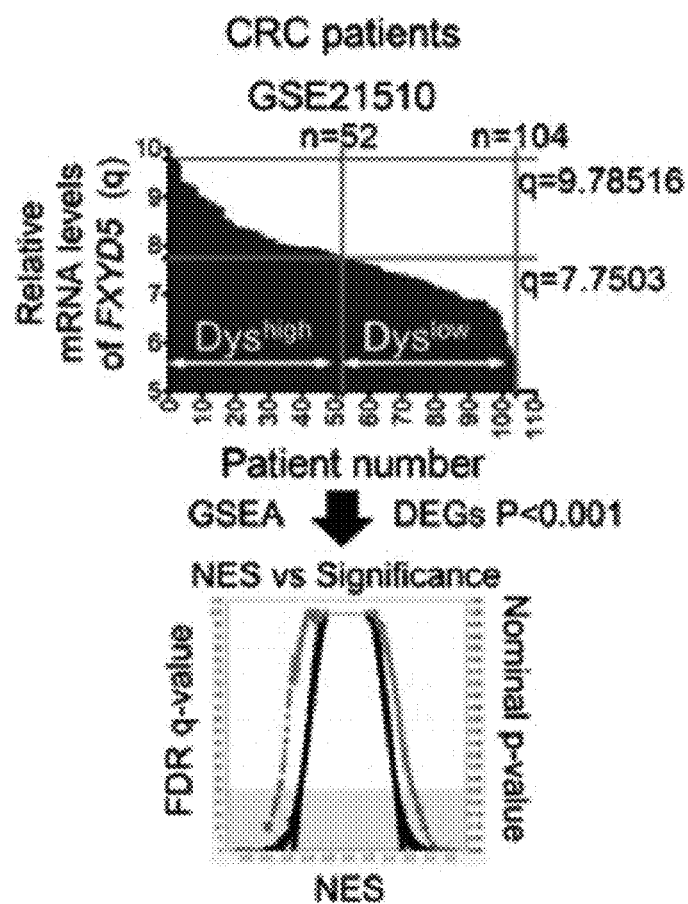
FIGS. 9A-9D illustrate bioinformatics analyses to identify dysadherin-associated mechanisms.
Figure 9B:
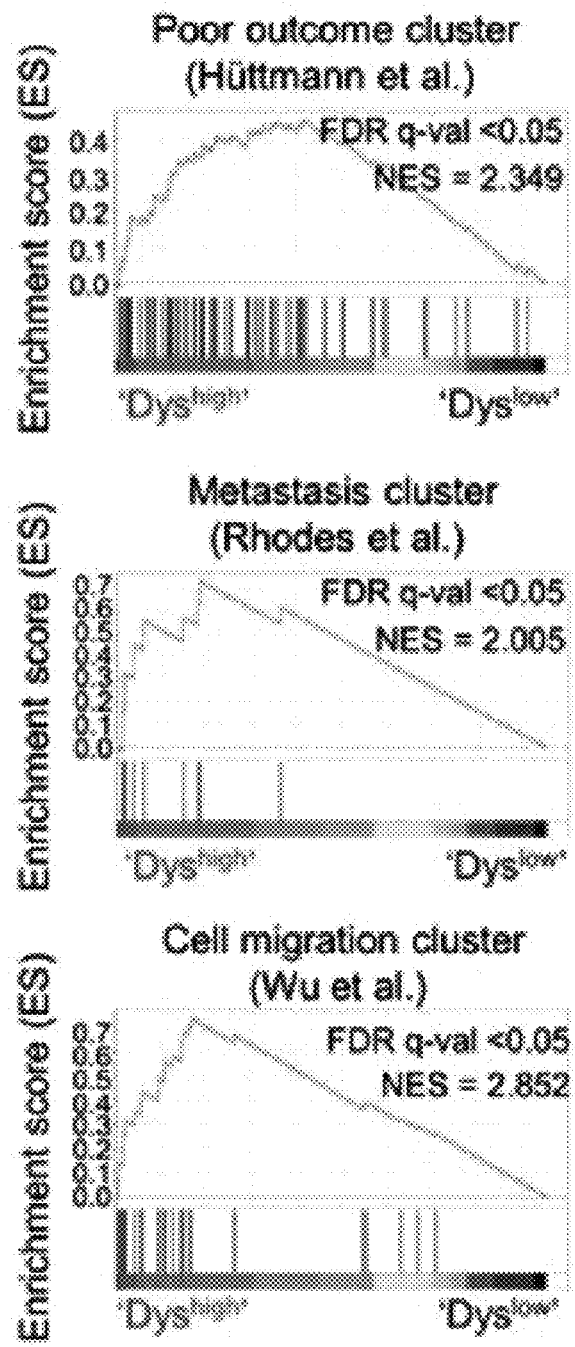
Figure 9C:
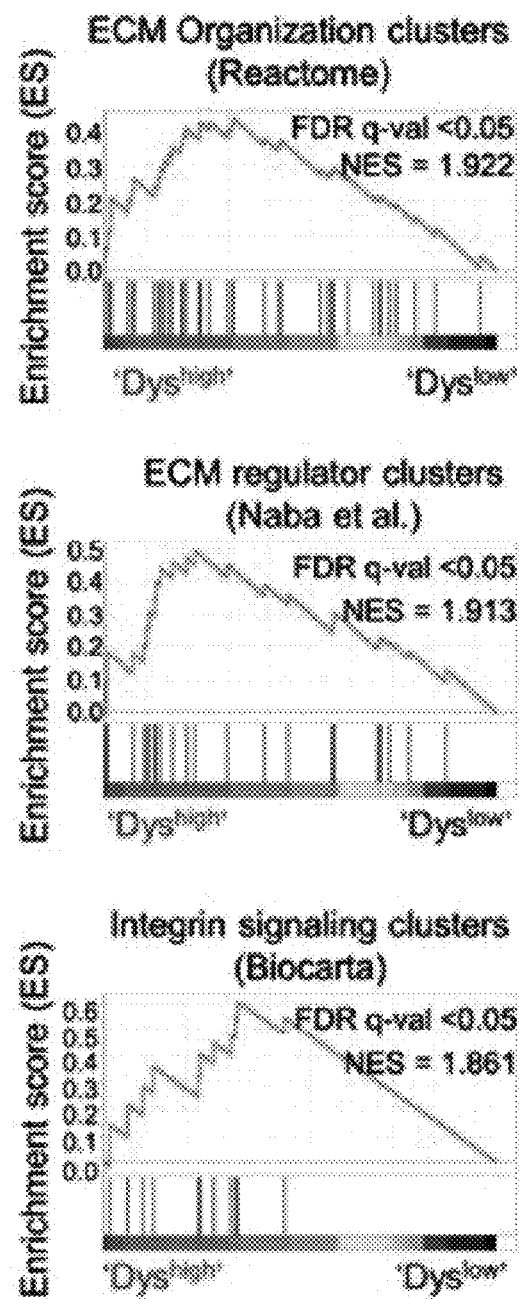
Figure 9D:
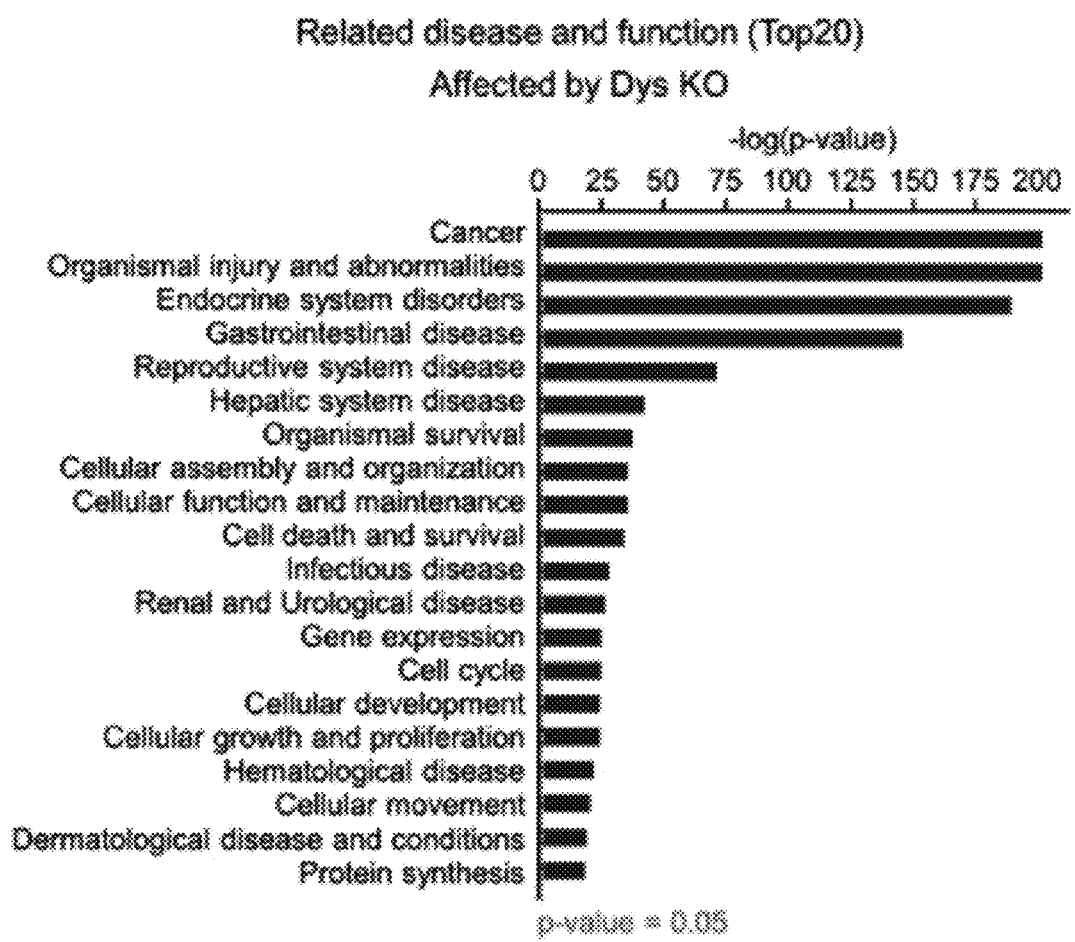
Figure 10A:
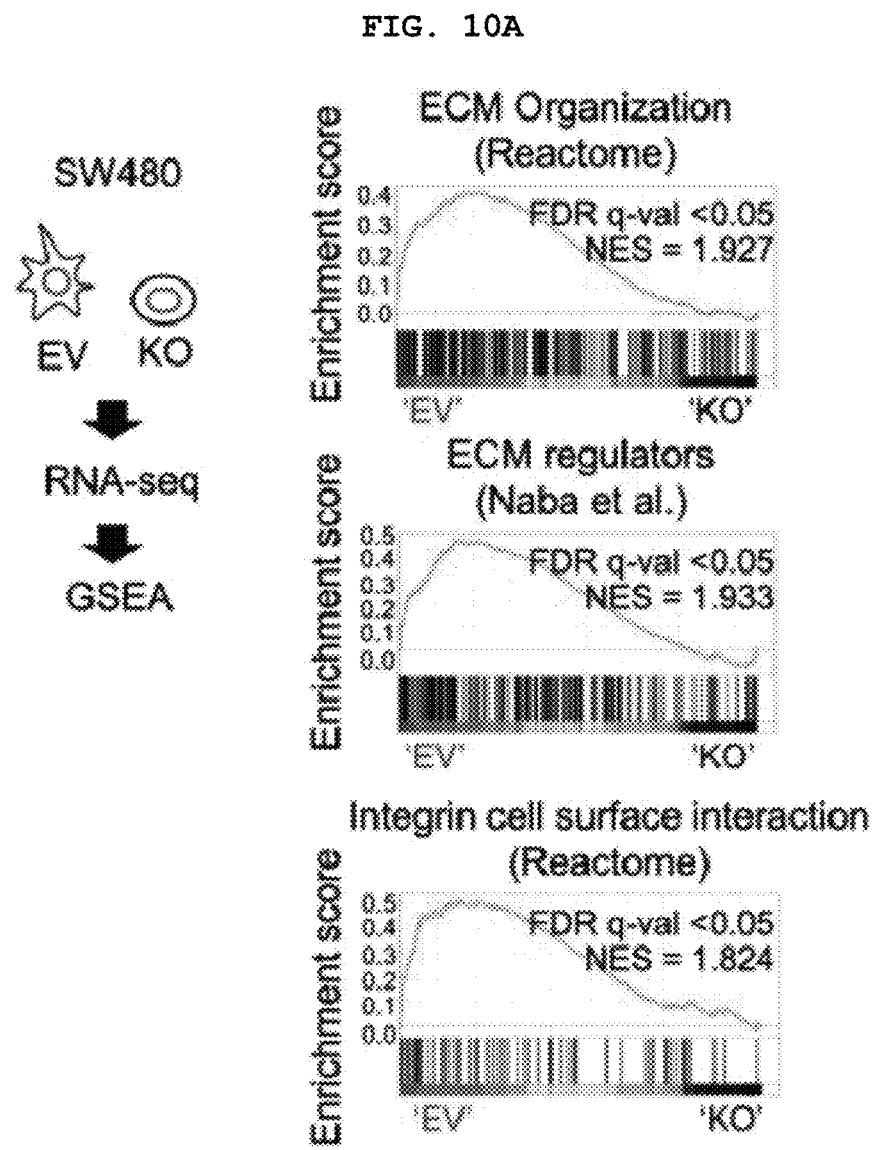
FIGS. 10A-10F illustrate the ECM-integrin pathway is a potential downstream mediator of dysadherin with tumorigenesis.
Figure 10B:
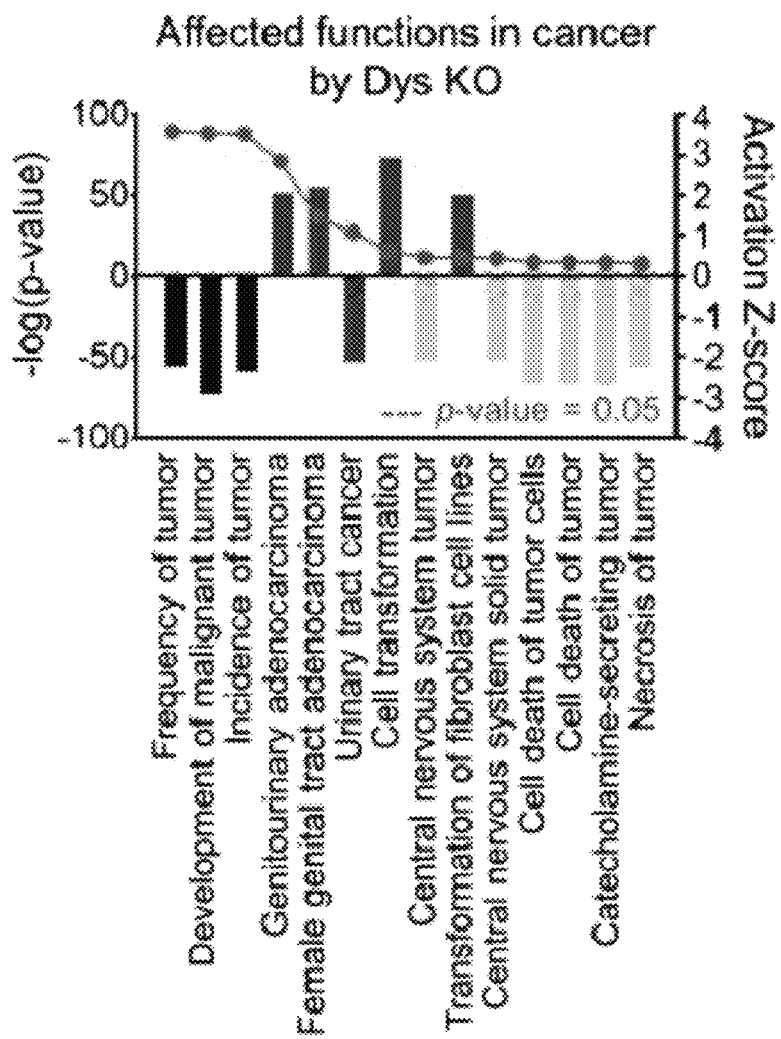
Figure 10C:
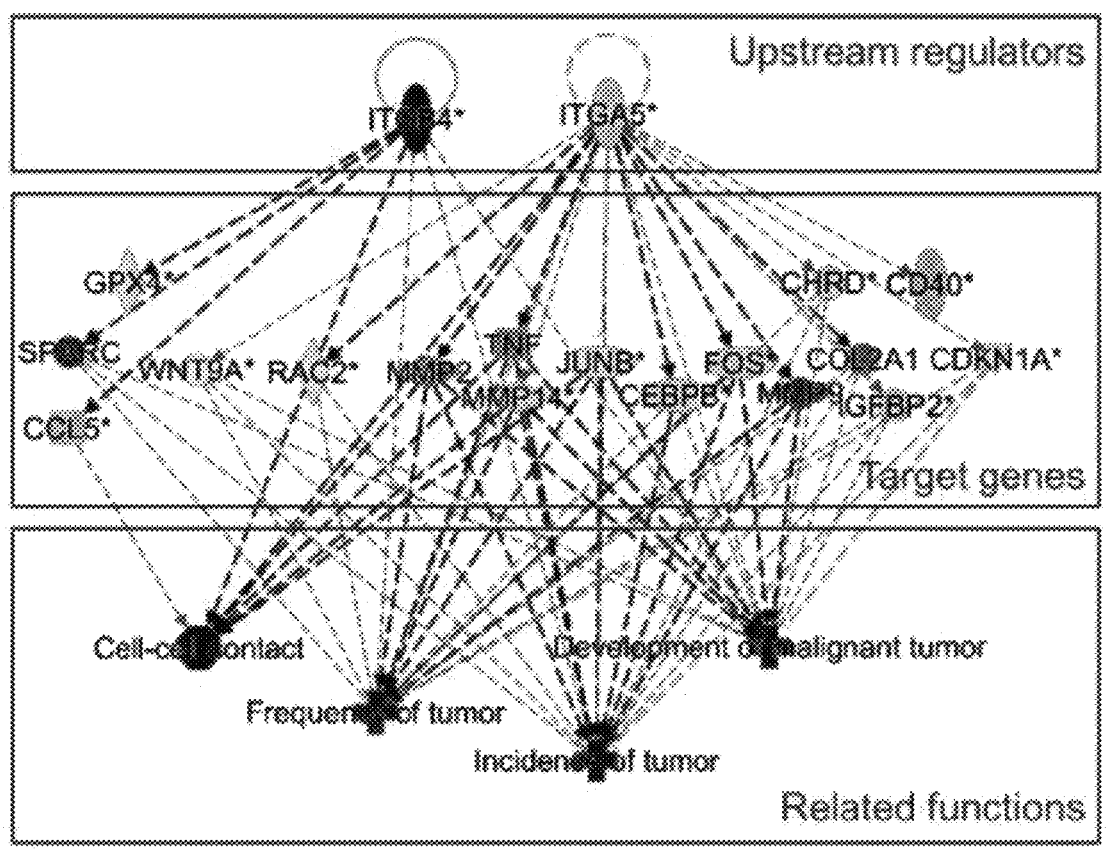
Figure 10D:
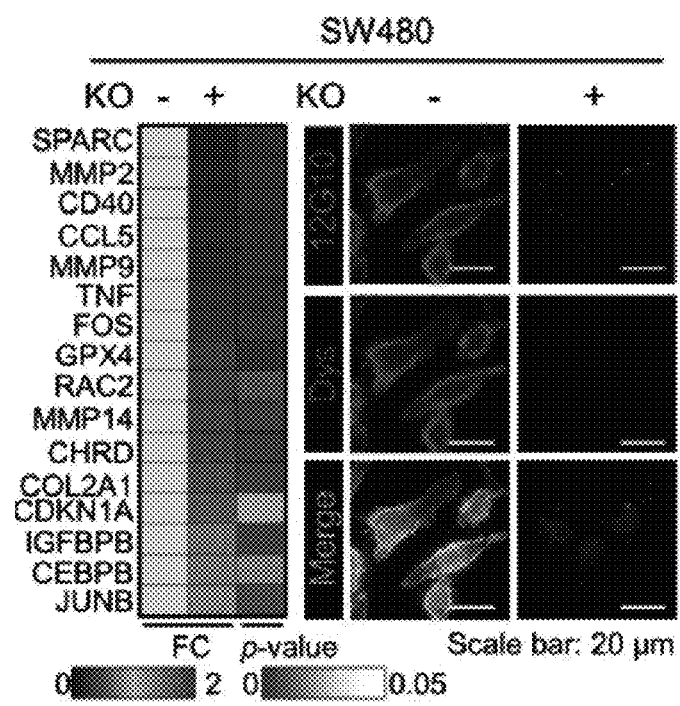
Figure 10E:
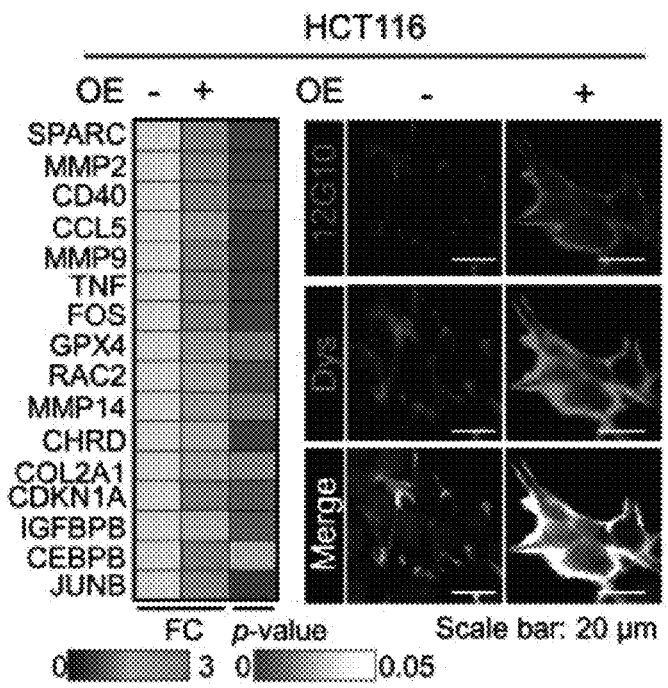
Figure 10F:
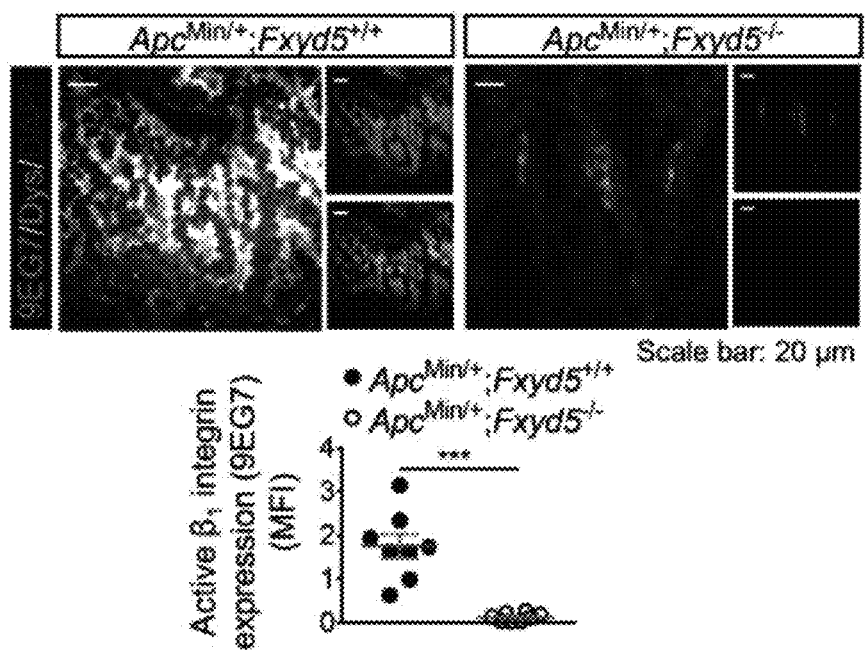

To obtain further mechanistic insights, we compared the gene expression profiles of tumors from 104 CRC patients (GSE21510) with higher dysadherin expression (dysadherin$^{high}$) versus lower dysadherin expression (dysadherin$^{low}$). The differentially expressed genes in the dysadherin$^{high}$ tumors was subjected to GSEA (FIG. 9A). Malignant gene signatures associated with poor clinical outcome, metastasis, and migration clusters were significantly enriched in the dysadherin$^{high}$ tumors (FIG. 9B). Intriguingly, gene signatures related to ECM receptor pathways such as ECM organization, ECM regulators, and integrin signaling, were also significantly up-regulated in the dysadherin-tumors (FIG. 9C). Consistent with the clinical data, GSEA of RNA-sequencing data from dysadherin-KO SW480 cells (n=4,437, p<0.05) repeatedly confirmed the link between dysadherin and the ECM receptor pathway, as indicated by enrichment gene signatures related to ECM organization, ECM regulators, and integrin-cell surface interactions (FIG. 10A). Next, we explored the potential molecular network involved in the relationship between dysadherin and ECM receptor pathways by Ingenuity Pathway Analysis of the differentially expressed genes in dysadherin-KO SW480 cells. The data revealed the diseases and functions most affected by dysadherin KO (FIG. 9D). As expected, cancer was the disease most affected by dysadherin KO, which led to robust decreases in tumor frequency, tumor incidence, and malignant tumor development (FIG. 10B). Analyses of upstream regulators further revealed that the reductions in these cancer-related functions are presumably modulated by a set of integrin signaling target genes (FIG. 10C). Validation with CRC cells confirmed that integrin target gene expression tended to decrease upon dysadherin KO and increase upon dysadherin OE. Next, we assessed integrin activation by immunofluorescence staining using an antibody that specifically recognizes the active conformation of β1 integrin (clone 12G10). The extent of active β1 integrin was strikingly reduced by dysadherin KO but increased by dysadherin OE (FIGS. 10D,10E). Using an antibody that specifically recognizes the active conformation of murine β$_1$ integrin (clone 9EG7), we confirmed the role of dysadherin in regulating β1 integrin activation in intestinal tumors of Apc$^{Min/+}$;Fxyd5$^{-/-}$ mice and Apc$^{Min/+}$;Fxyd5$^{+/+}$ mice, showing a striking reduction in β1 integrin activation in the absence of dysadherin (FIG. 10F). Collectively, these comprehensive analyses suggest the potential involvement of ECM-integrin signaling in dysadherin-mediated intestinal tumorigenesis.

4. Dysadherin Directly Binds Fibronectin Through its Extracellular Domain

Figure 11A:
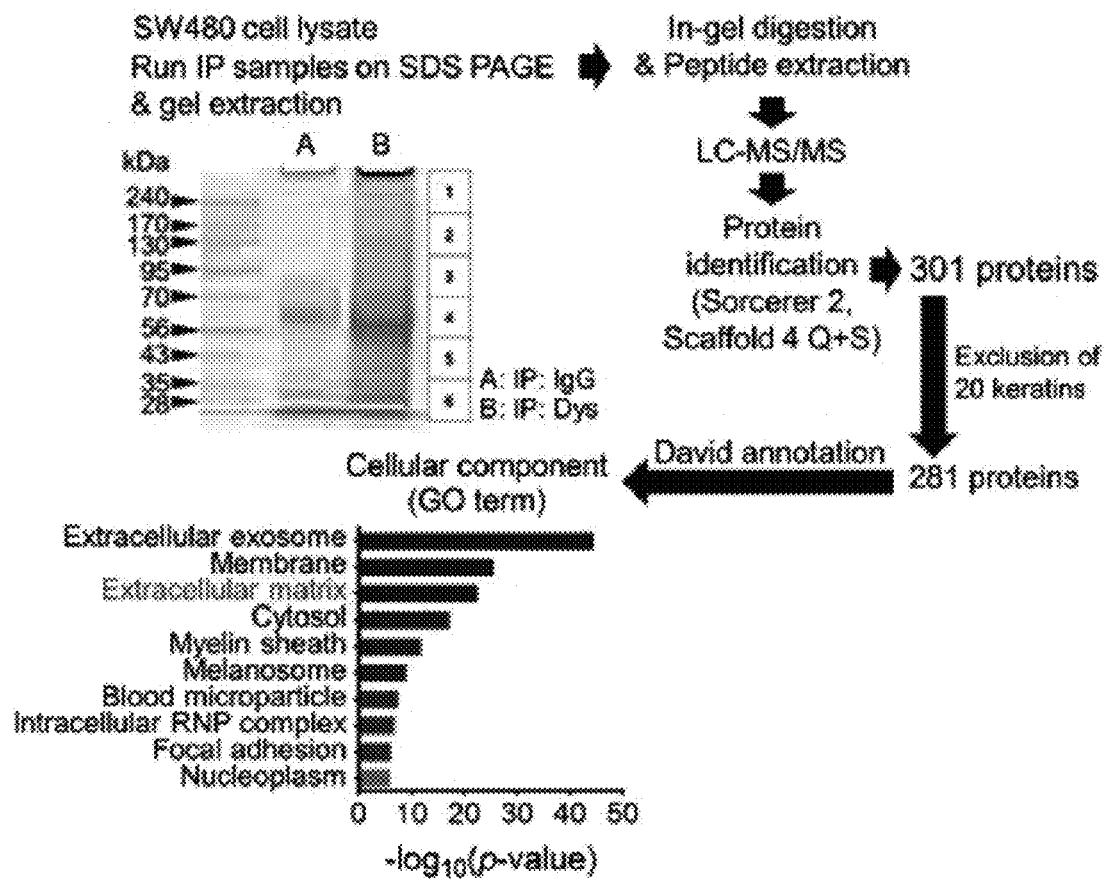
FIGS. 11A-11F illustrate identification and validation of binding between dysadherin and fibronectin.

To identify the downstream mechanisms through which dysadherin regulates intestinal tumorigenesis, potential dysadherin-interacting proteins in SW480 cell extracts were identified through co-IP with a monoclonal anti-dysadherin antibody (M53) followed by LC-MS. A total of 301 proteins were pulled down with the M53 antibody and were identified as potential dysadherin-interacting proteins (FIG. 11A). Gene ontology analysis with DAVID, a web-based functional annotation platform, revealed that ECM proteins make up one of the top clusters of dysadherin-interacting proteins. Particularly among ECM proteins, fibronectin is known to act as a ligand for various integrin receptors, linking the ECM with intracellular signaling cascades. Fibronectin was significantly enriched among the proteins co-IPed with anti-dysadherin (Table 5).

TABLE 5

| Identified proteins | Accession | Probe identification probability (Spectral counts) | |
|---|---|---|---|
| | | IP M53 | IP IgG |
| 1 Isoform 10 of Fibronectin OS = Homo sapiens GN = FN1 | FN1 | 100% (20) | 6% (0) |
| 2 Cytoplasmic dynein 1 heavy chain 1 OS = Homo sapiens | DYNC1H1 | 100% (19) | 10% (0) |
| 3 Myosin-9 OS = Homo sapiens GN = MYH9 PE = 1 SV = 4 | MYH9 | 100% (35) | 13% (0) |
| 4 Isoform 2 of Plectin OS = Homo sapiens GN = PLEC | PLEC | 100% (4) | 15% (0) |
| 5 DNA-dependent protein kinase catalytic subunit | PRKDC | 100% (26) | 72% (0) |
| 6 40S ribosomal protein S15a OS = Homo sapiens | RPS15A | 100% (6) | 75% (0) |
| 7 Dolichyl-diphosphooligosaccharide--protein | RPN1 | 100% (4) | 85% (1) |
| 8 Desmoplakin OS = Homo sapiens GN = DSP PE = 1 SV = 3 | DSP | 100% (36) | 91% (1) |
| 9 Junction plakoglobin OS = Homo sapiens GN = JUP PE = 1 | JUP | 100% (10) | 98% (0) |
| 10 Isoform 2 of Glyceraldehyde-3-phosphate | GAPDH | 100% (4) | 99% (1) |
| 11 Heat shock protein HSP 90-alpha OS = Homo sapiens | HSP90AA1 | 100% (13) | 100% (2) |
| 12 ADP/ATP translocase 3 OS = Homo sapiens GN = SLC25A6 | SLC25A6 | 100% (10) | 100% (2) |
| 13 Isoform 2 of Annexin A2 OS = Homo sapiens GN = ANXA2 | ANXA2 | 100% (4) | 100% (2) |
| 14 Isoform 2 of ATP synthase subunit alpha, mitochondrial | ATP5A1 | 100% (10) | 100% (3) |
| 15 Heat shock protein beta-1 OS = Homo sapiens | HSPB1 | 100% (13) | 100% (3) |
| 16 Histone H4 OS = Homo sapiens GN = HIST1H4A PE = 1 | HIST1H4A | 100% (5) | 100% (3) |
| 17 Isoform 2 of 40S ribosomal protein S20 OS = Homo | RPS20 | 100% (5) | 100% (3) |
| 18 ATP synthase subunit beta, mitochondrial OS = Homo | ATP5B | 100% (16) | 100% (4) |
| 19 Tubulin beta-4B chain OS = Homo sapiens GN = TUBB4B | TUBB4B | 100% (9) | 100% (4) |
| 20 40S ribosomal protein S3 OS = Homo sapiens GN = RPS3 | RPS3 | 100% (13) | 100% (6) |
| 21 Tubulin beta chain OS = Homo sapiens GN = TUBB PE = 1 | TUBB | 100% (49) | 100% (16) |
| 22 Heat shock cognate 71 kDa protein OS = Homo sapiens | HSPA8 | 100% (24) | 100% (16) |

Figure 12A:
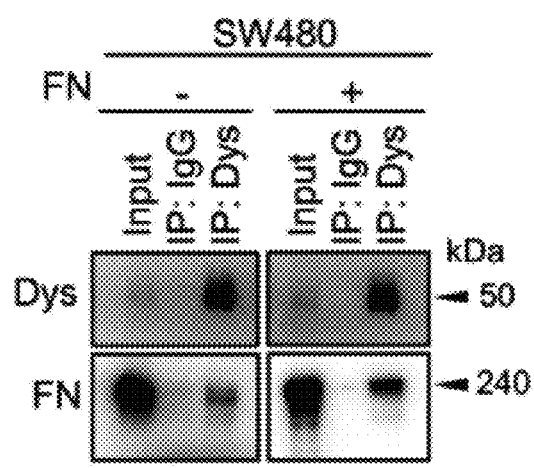
Figure 12B:
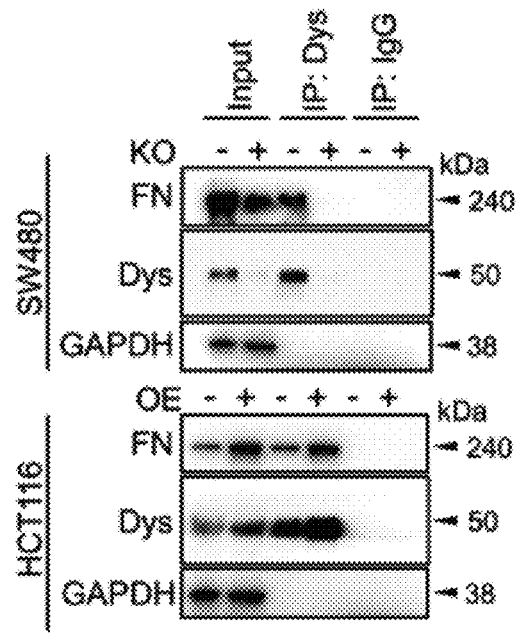
(FIG. 12B) Co-IP with M53 and subsequent immunoblot analyses confirm that the quantity of dysadherin-bound fibronectin is decreased by dysadherin KO but increased by dysadherin OE.

Thus, we conducted further investigation on the potential interaction between dysadherin and fibronectin. We confirmed a dysadherin-fibronectin interaction in SW480 cells by immunoblot analysis of anti-dysadherin co-IP samples. Additionally, when we added exogenous fibronectin prior to anti-dysadherin co-IP, the quantity of dysadherin-bound fibronectin increased (FIG. 12A). The dysadherin-fibronectin interaction was decreased upon dysadherin KO in SW480 cells, and was increased by dysadherin OE in HCT116 cells (FIG. 12B).

Figure 12C:
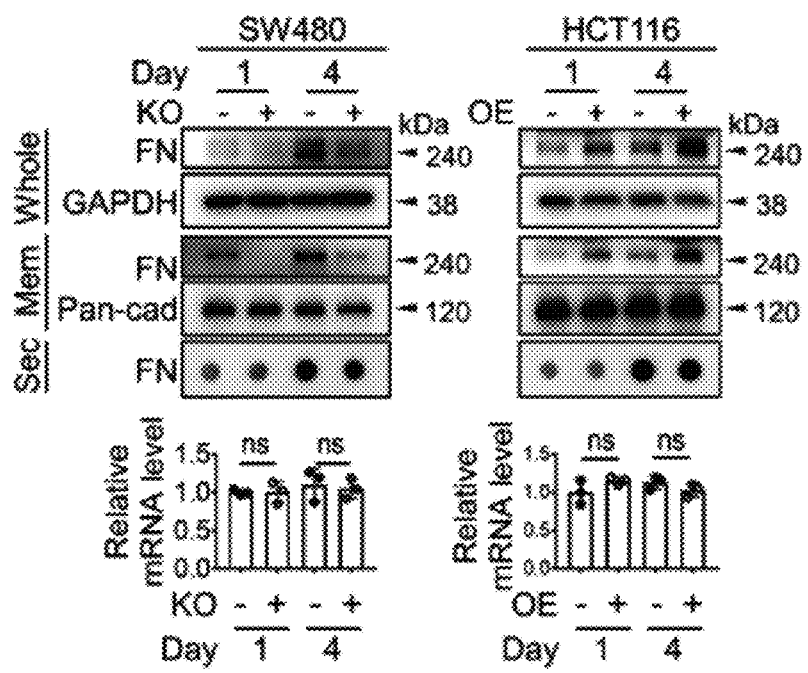
(FIG. 12C) Whole-protein lysates and membrane fractions were extracted from cells at the indicated time points. Culture media were collected and applied to dot blot assays to compare the quantities of secreted fibronectin. RT-qPCR analyses were performed to compare fibronectin mRNA transcript levels (n=3/group).

To obtain deeper insights into this phenomenon, we compared the quantity of fibronectin in total cell protein extracts, membrane fraction extracts, and the secretome in the culture media and mRNA transcripts in dysadherin-KO and dysadherin-OE CRC cells. Dysadherin-induced alteration of fibronectin protein levels was not due to changes in mRNA or secreted protein levels; rather, membrane-bound fibronectin was decreased upon dysadherin KO and increased upon dysadherin OE, suggesting that the dysadherin-fibronectin interaction enriches fibronectin at the cellular membrane. Thus, fibronectin became more abundant in CRC cell protein extracts over time (FIG. 12C).

Figure 11B:
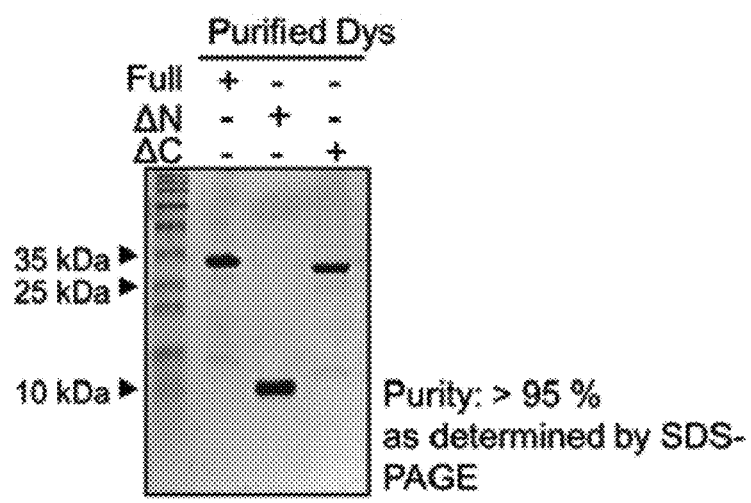
Figure 11C:
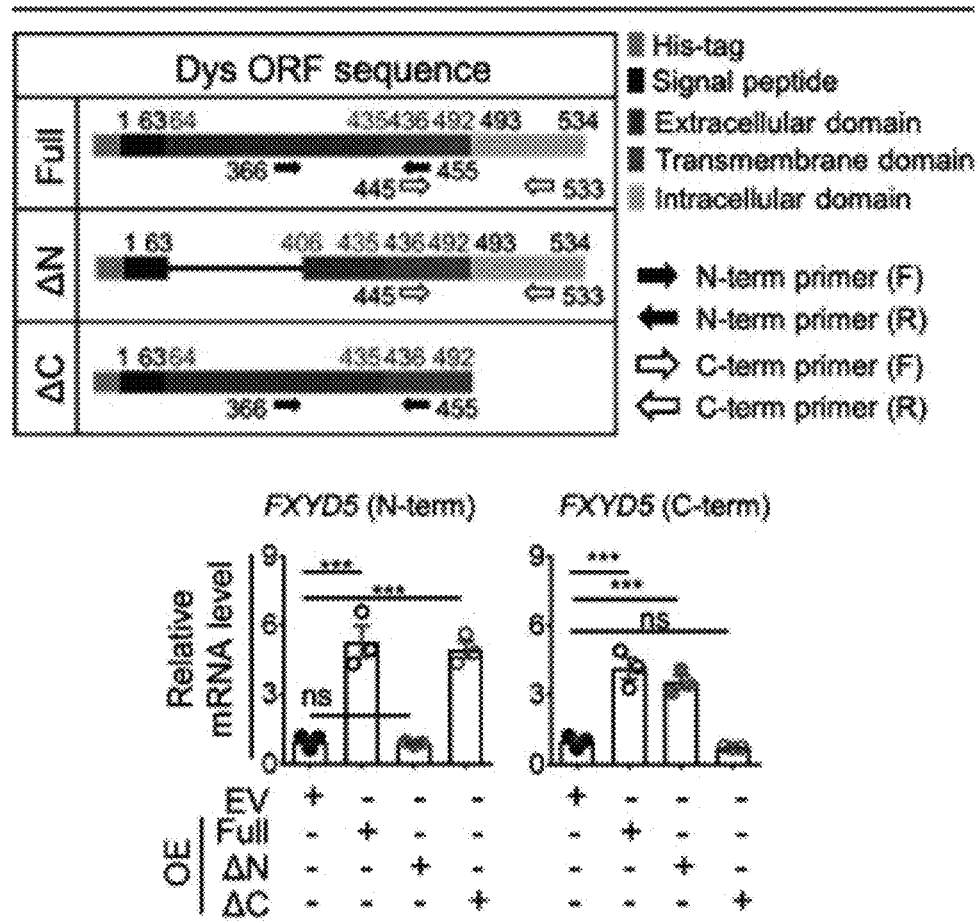
Figure 11D:
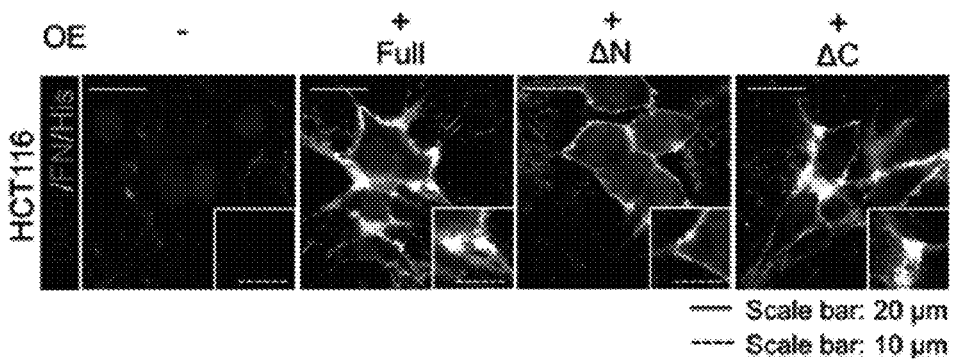
Figure 12D:
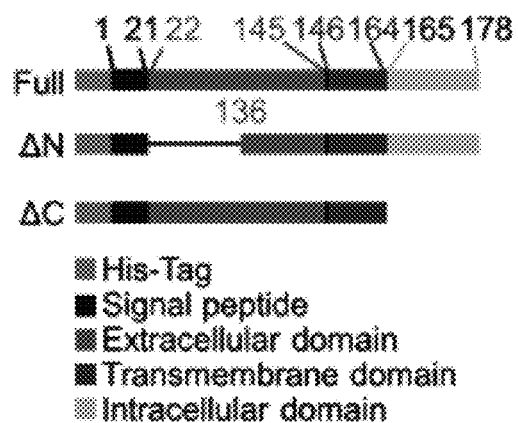
(FIG. 12D) Schematic of full-length (wild-type) and mutant dysadherin proteins purified from E. coli.
Figure 12E:
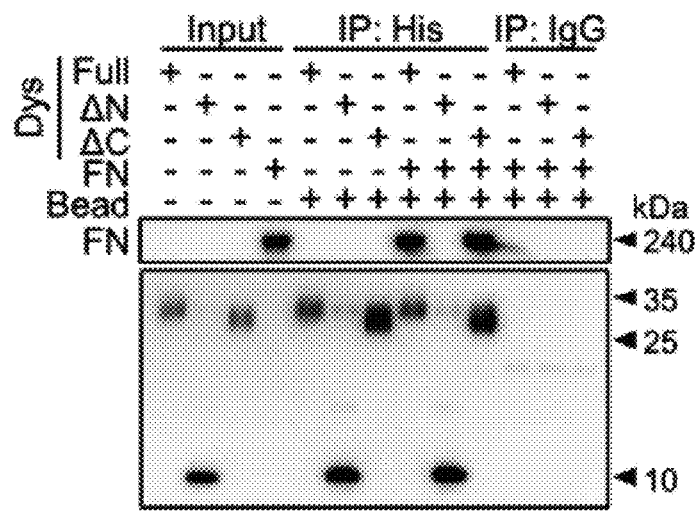
(FIG. 12E) Pull-down assay using various forms of purified His-tagged dysadherin proteins and purified fibronectin protein to determine direct protein-protein interactions. In all panels, data are reported as means±SEMs; ns indicates no significance. Statistical comparisons between 2 groups were performed using Student's t-test. Dys: dysadherin, FN: fibronectin, Mem: membrane, Sec: secreted, ΔC: ΔC-mutant, ΔN: ΔN-mutant.

Dysadherin is a membrane protein that consists of a short C-terminal cytoplasmic tail, a transmembrane domain, and a long extracellular domain. This unusually long extracellular domain may facilitate interactions with other membrane proteins or ECM components, leading to the alteration of signaling dynamics. Thus, we further investigated the interaction between dysadherin and fibronectin by generating purified recombinant His-tagged dysadherin protein (FIG. 11B). We generated 2 mutant forms of dysadherin (FIG. 12D): one without the extracellular N-terminal sequence (amino acids 22-135, ΔN-mutant), and the other without the intracellular C-terminal sequence (amino acids 165-178, ΔC-mutant). A pull-down assay of these purified His-tagged proteins validated the direct binding of dysadherin to fibronectin; while the ΔC-mutant was still able to bind fibronectin, the ΔN-mutant lost the ability to bind fibronectin (FIG. 12E). Next, we generated HCT116 cell lines that overexpressed 3 different forms of dysadherin conjugated with a His-tag: full length, ΔN-mutant, or ΔC-mutant (FIG. 11C). IF revealed binding of fibronectin to full-length dysadherin and the ΔC-mutant form, as indicated by the colocalization of fibronectin and dysadherin on the cellular membrane, but the ΔN-mutant form did not interact with fibronectin at the cellular level (FIG. 11D). In further analyses, to find the specific amino acid sequence involved in dysadherin-fibronectin binding, we synthesized several His-tagged peptides (N #1~#5) mimicking the amino acid sequences of dysadherin found in five different regions of extracellular domain (FIG. 12F) and performed a pull-down assay with purified fibronectin. Of note, we found that a peptide N #3 (PADETPQPQTQTQQLEGTDGP) (SEQ ID NO: 3) and N #4 (KAAHPTDDTTTLSERPSPST) (SEQ ID NO: 6) displayed fibronectin-binding activity, while N #1, #2 and #5 did not (FIG. 12G). In line with this result, only peptide N #3 and N #4 displayed a selective cytotoxicity against SW480 cells, while showing a limited effect against dysadherin KO SW480 cells (FIG. 12H). Although further studies are required to determine the exact physicochemical interaction between dysadherin and fibronectin, our data suggest that the middle sequences within the extracellular domain of dysadherin may be important for its binding activity to fibronectin.

Figure 11E:
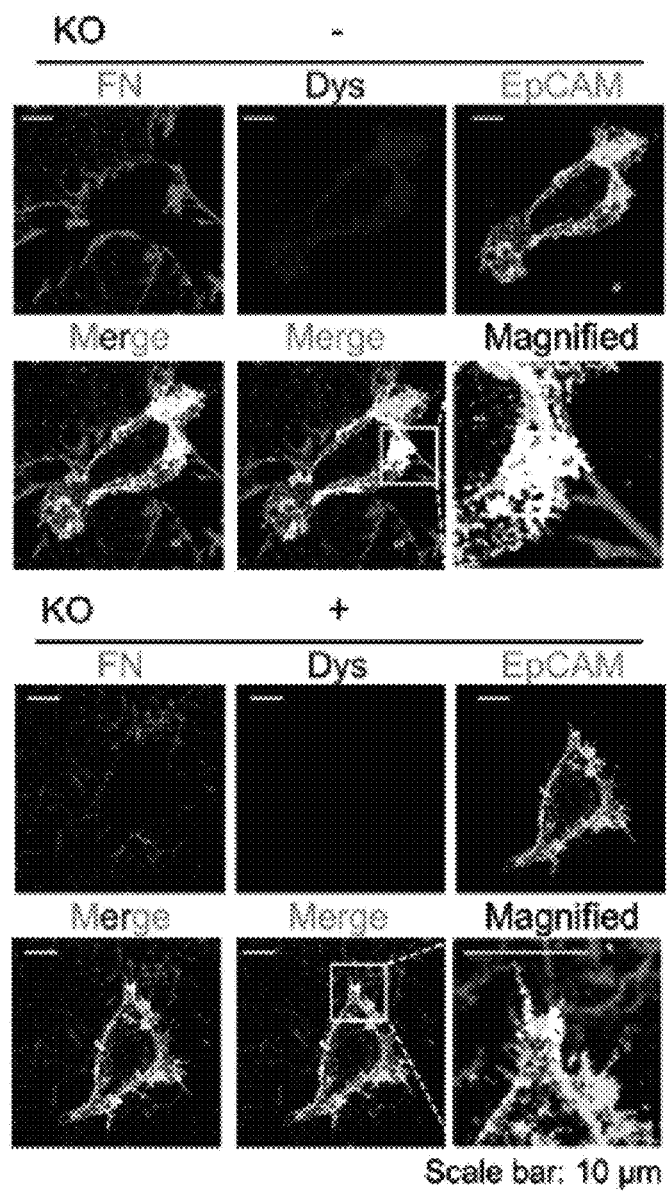
Figure 11F:
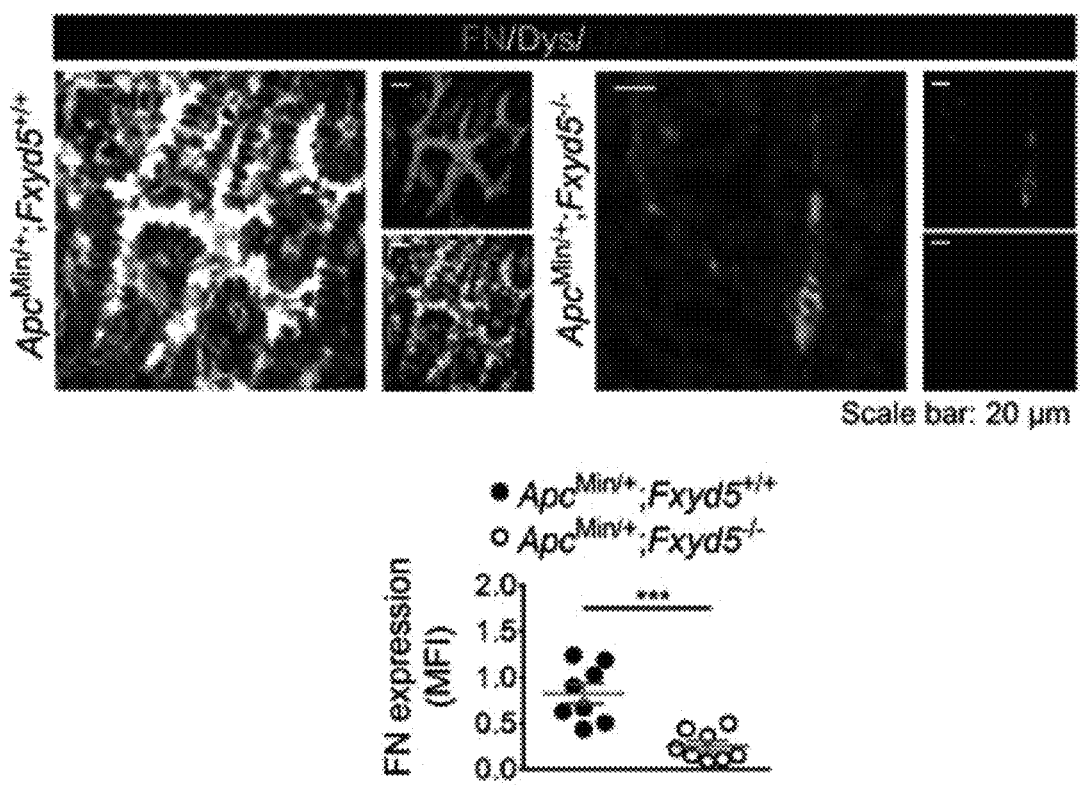

Dysadherin KO resulted in significant reduction of fibronectin on the cellular membrane in SW480 cells (FIG. 11E). Consistent with these in vitro data, fibronectin was significantly enriched on the membranes of dysadherin-expressing tumor cells within $Apc^{Min/+};Fxyd5^{+/+}$ mouse intestinal tumors, and the enrichment of fibronectin was significantly decreased in dysadherin-deficient mouse tumors (FIG. 11F). These results suggest that dysadherin and fibronectin interact in tumor cells and that the extracellular domain of dysadherin is a key regulatory element involved in fibronectin binding.

Figure 13B:
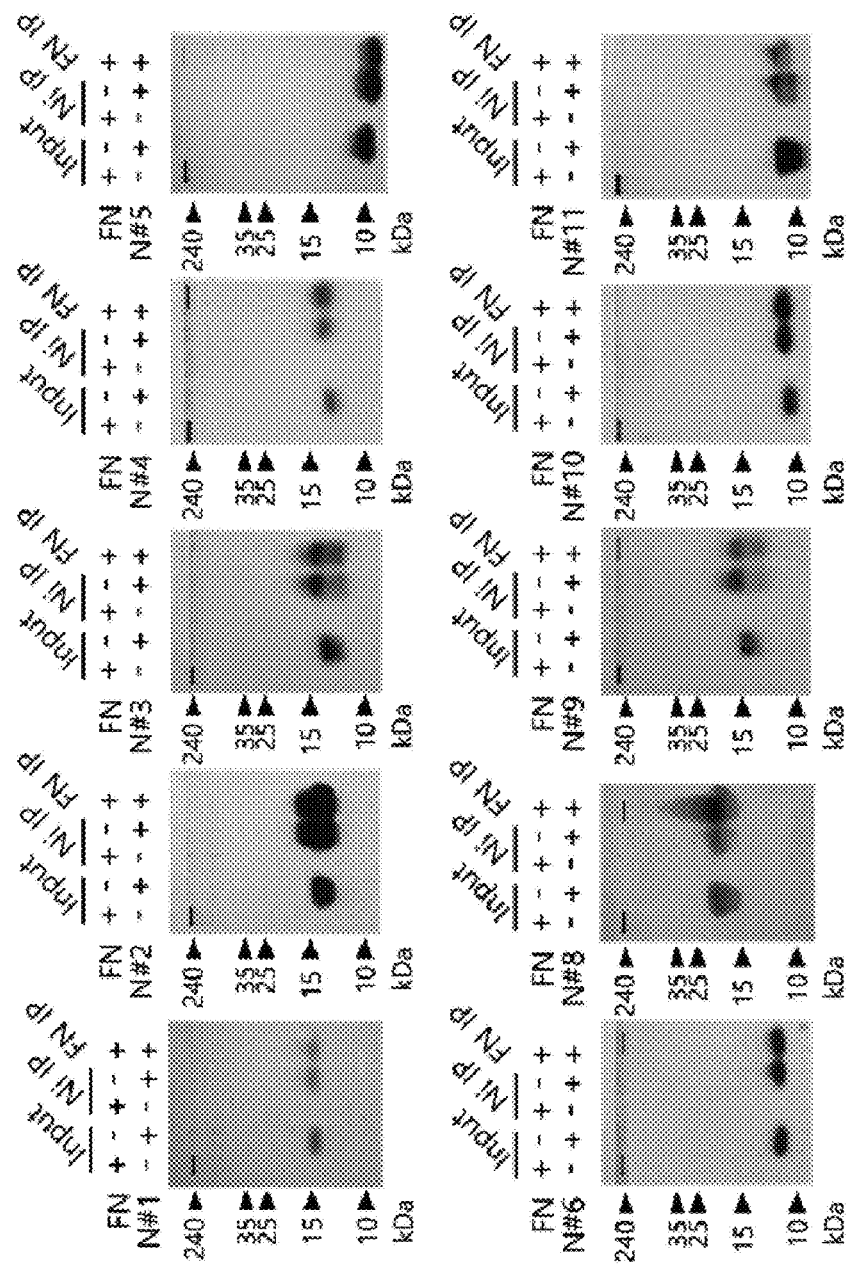
FIG. 13B illustrates pull-down assay using purified fibronectin and purified His-tagged synthesized peptides to determine the specific sequence with fibronectin-binding activity.
Figure 13C:
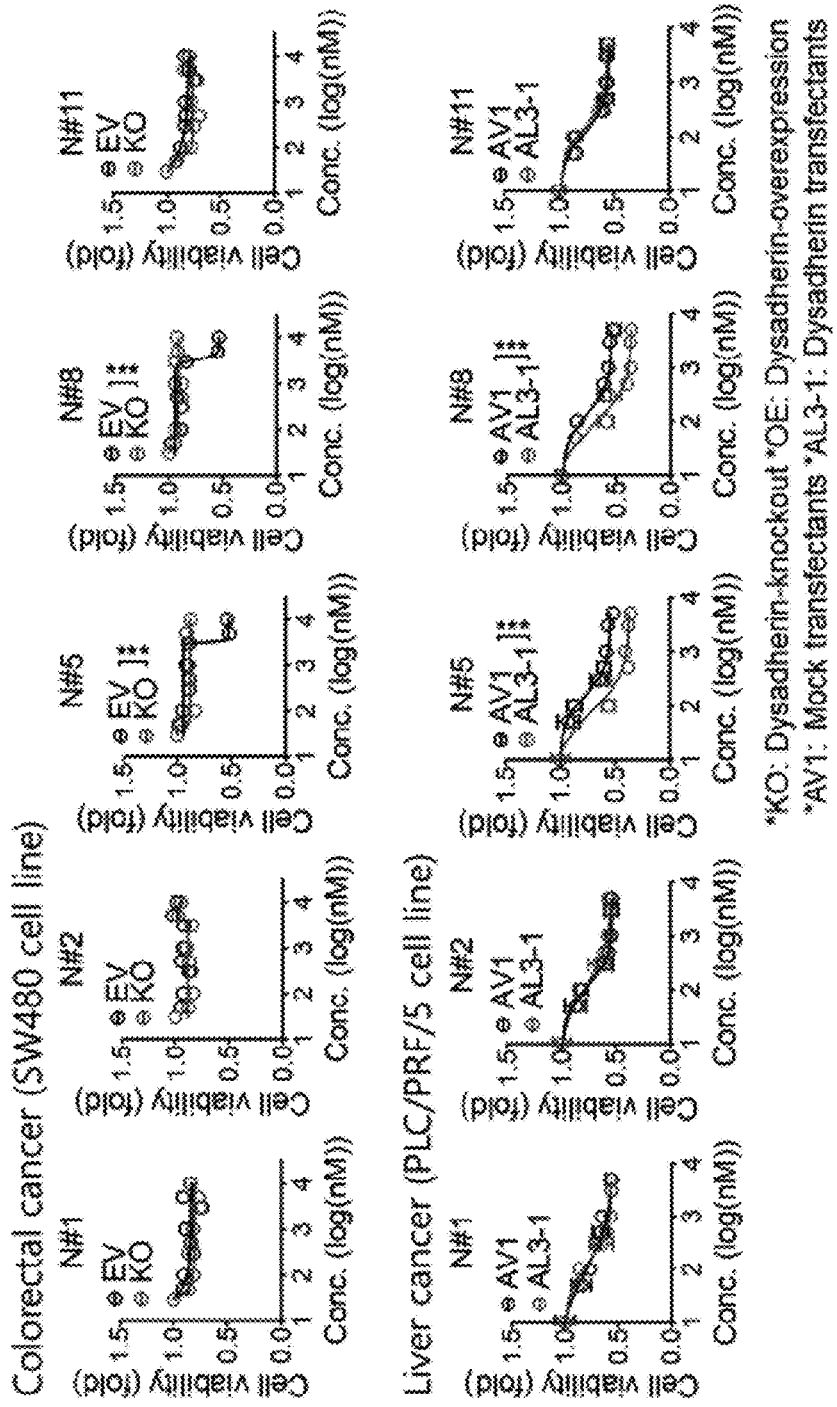
FIGS. 13C-13D illustrate cell viability were measured by an MTT assay at 48 hours after the treatment of annotated peptide in SW480 cells with and without KO of dysadherin.
Figure 13D:
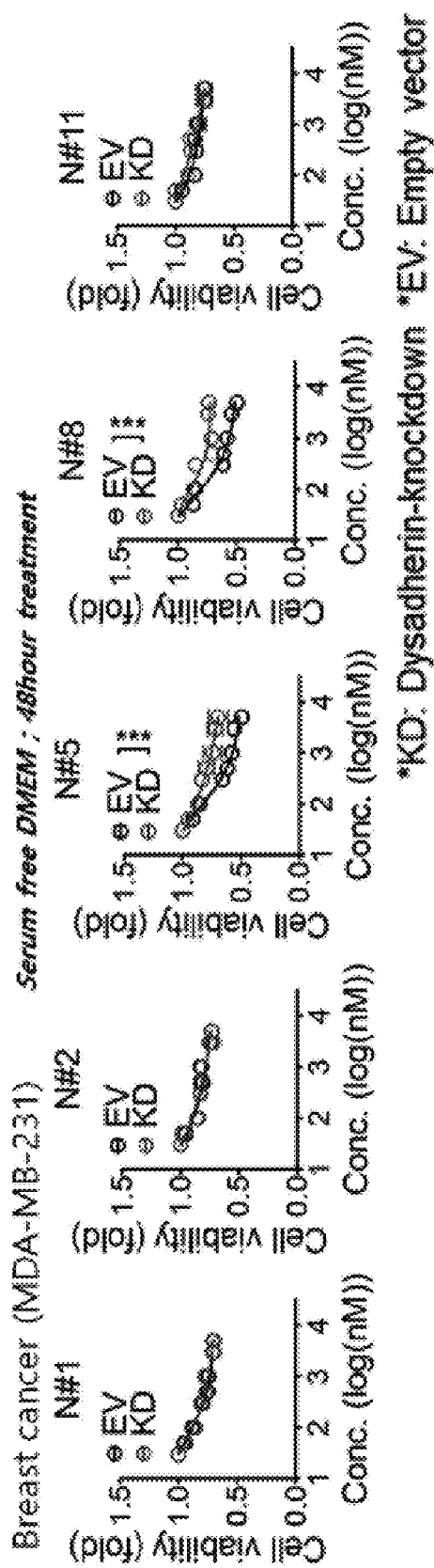

5. The Dysadherin-Fibronectin Interaction Facilitates Sustained Activation of the Fibronectin-Integrin-FAK Axis Fibronectin is a primary ECM component that mediates a wide variety of cellular interactions with the ECM and plays pleiotropic roles in diverse processes in cancer, such as cancer cell growth, migration, and invasion. Furthermore, fibronectin is an adhesive glycoprotein primarily involved in cellular adhesive interactions; thus, we investigated whether dysadherin expression affects fibronectin-mediated cell adhesion. First, we compared the adhesive capacity of dysadherin-OE HCT116 cells with various ECM protein coatings. We observed a significant tendency towards greater adhesive capacity with increasing concentrations of all tested ECM proteins (fibronectin, laminin, and collagen type I); however, dysadherin OE enhanced the adhesive capacity of HCT116 cells under fibronectin-coated conditions (FIG. 13A). Similarly, dysadherin KO reduced the capacity of SW480 cells to adhere to fibronectin without affecting their capacity to adhere to laminin or collagen type I (FIG. 13B), suggesting the specific role of dysadherin in cell-to-fibronectin adhesion.

Figure 14A:
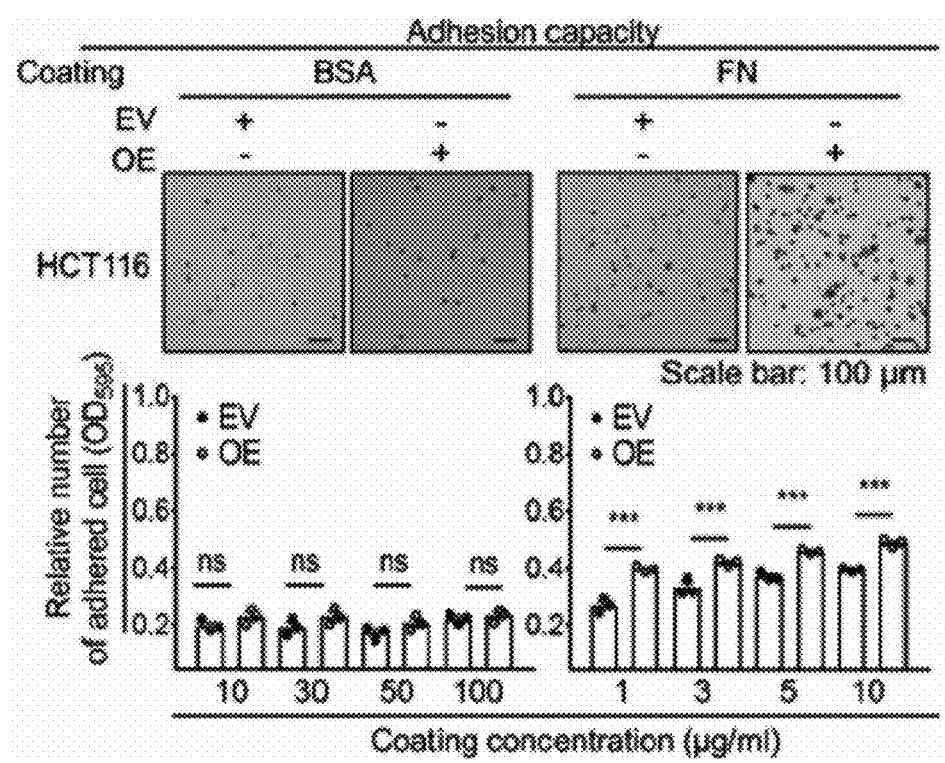
FIGS. 14A-14H illustrate effect of dysadherin on cancer cell adhesion capacity to fibronectin and confirmation of fibronectin knockdown with siRNAs.
Figure 14B:
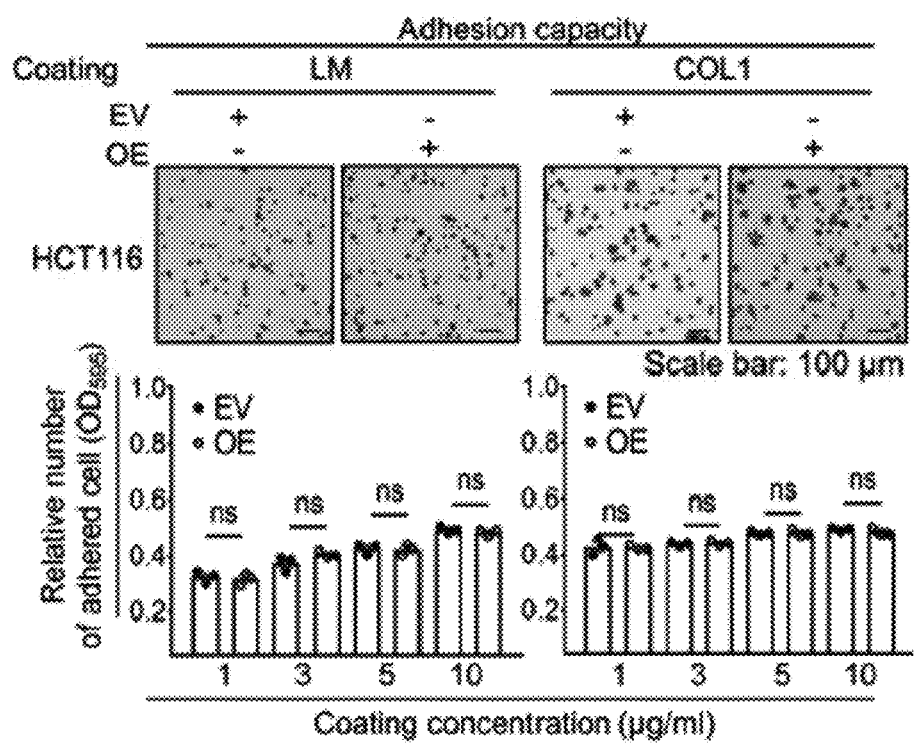
Figure 14C:
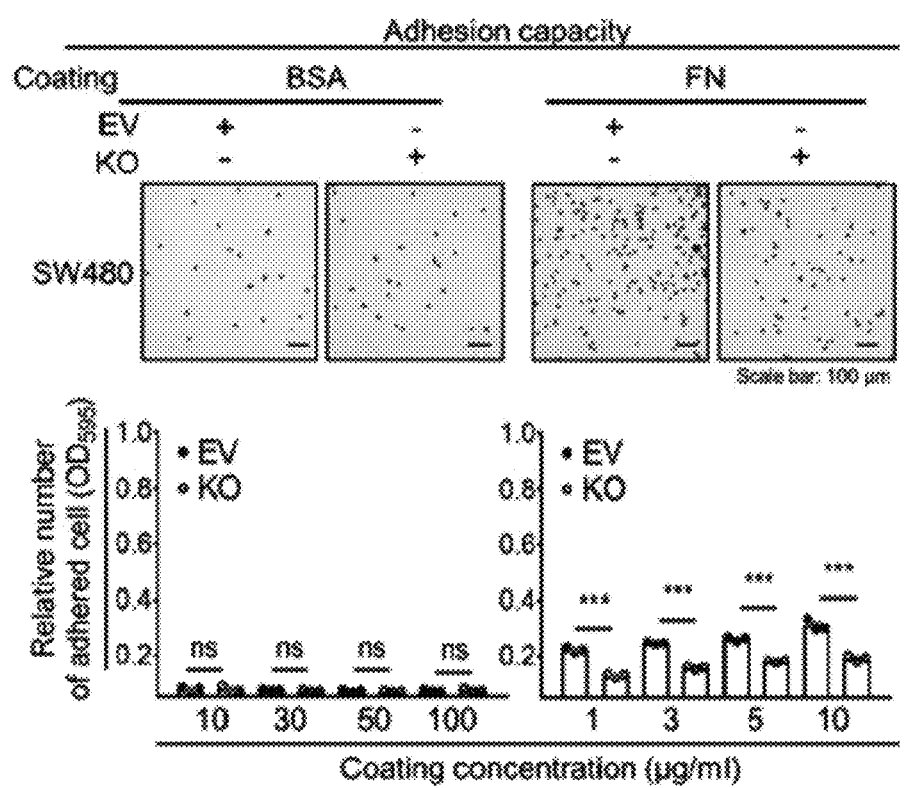
Figure 14D:
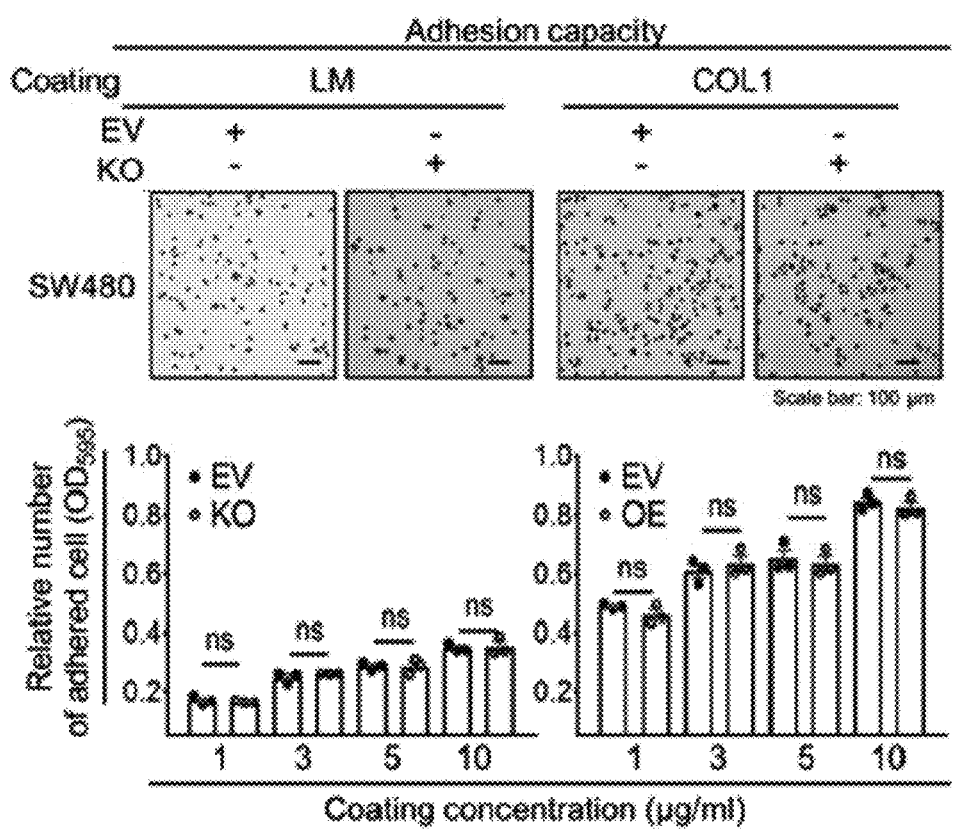
Figure 14E:
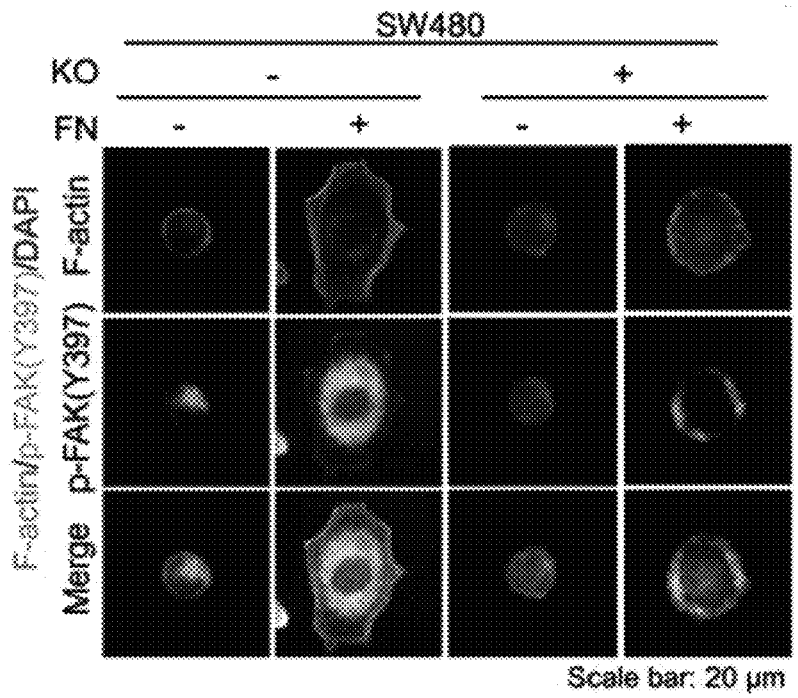
Figure 15A:
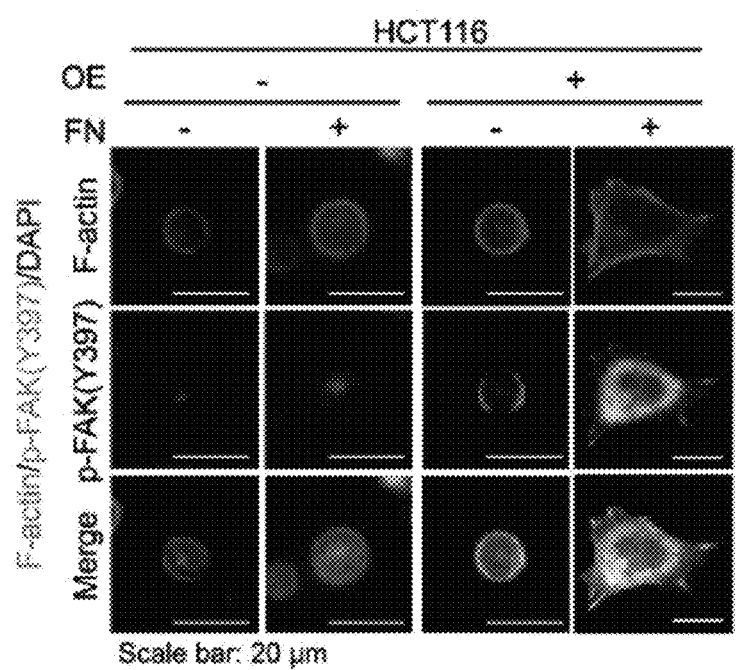
FIGS. 15A-15H illustrate dysadherin facilitates CRC adhesion to fibronectin and activates the fibronectin-integrin-FAK axis, leading to pro-tumor activity.
Figure 15B:
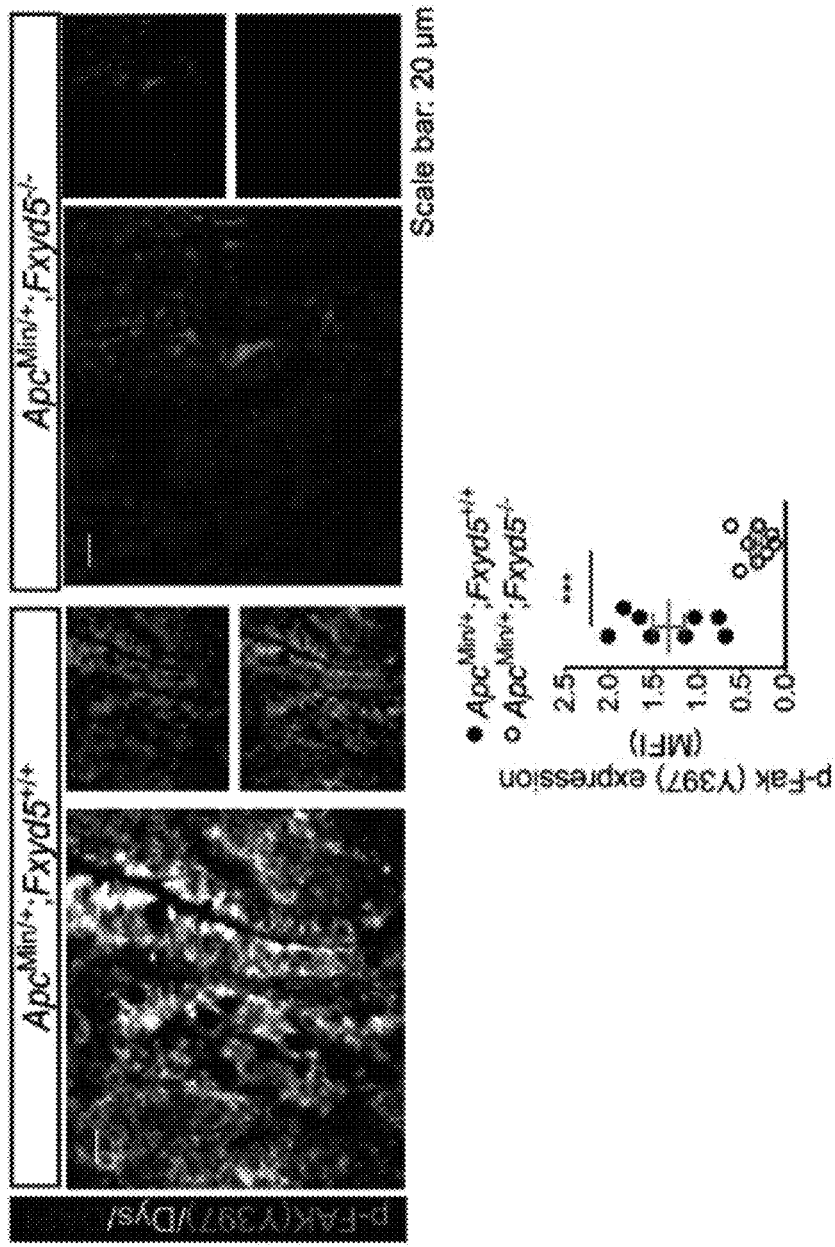
Figure 15C:
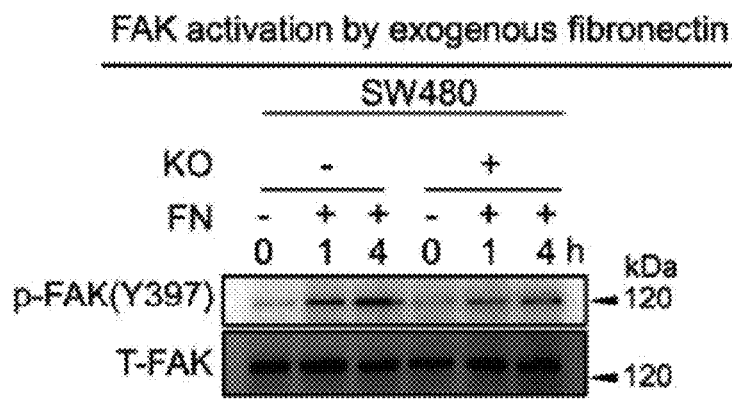
Figure 15D:
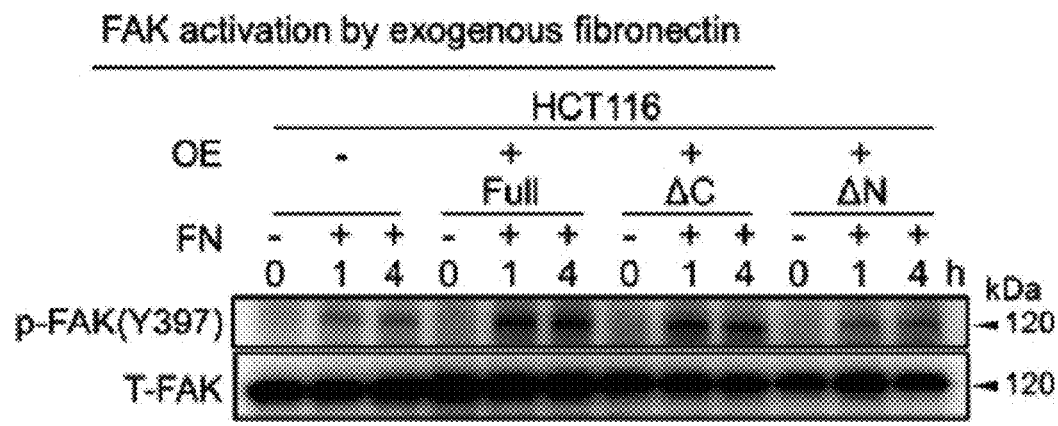
Figure 15:
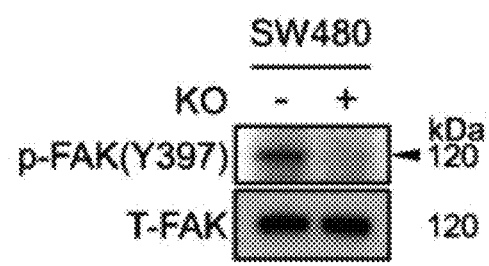

Fibronectin serves as a ligand for numerous integrins that activate the focal adhesion kinase (FAK) signaling pathway through the auto-phosphorylation of FAK at tyrosine 397 (Y397). Thus, we investigated the potential link between dysadherin and the fibronectin-integrin-FAK pathway upon cell adhesion to exogenous fibronectin coated on culture plates. Consistent with the adhesion assay, dysadherin-OE HCT116 cells showed a greater adhesive phenotype under fibronectin-coated conditions than control cells, with increased cell spreading, polymerized F-actin in their protrusions, more obvious spike-like filopodia and intercellular filaments, and an increase in FAK phosphorylation (p-FAK, FIG. 15A), while dysadherin-KO SW480 cells showed a lower adhesive phenotype with a decrease in p-FAK (FIG. 14E). Consistently, p-FAK was elevated in dysadherin-positive cells within the intestinal tumors of $Apc^{Min/+}$/$Fxyd5^{+/+}$ mice and this increase in p-FAK was significantly decreased by dysadherin deletion (FIG. 15B). An immunoblot analysis of SW480 cells showed that p-FAK was induced by cellular adhesion to fibronectin; however, the extent of p-FAK was significantly decreased by dysadherin KO (FIG. 15C). In HCT116 cells, dysadherin OE enhanced the levels of p-FAK following cell attachment to fibronectin (FIG. 15D). Of note, in this experiment, we found that deletion of the extracellular domain of dysadherin (ΔN-mutant) eliminated the effect of dysadherin on FAK activation during cell adhesion to fibronectin (FIG. 15D).

Figure 14F:
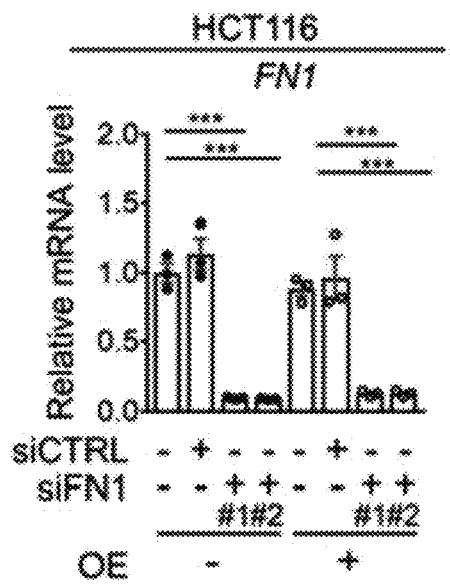
Figure 14G:
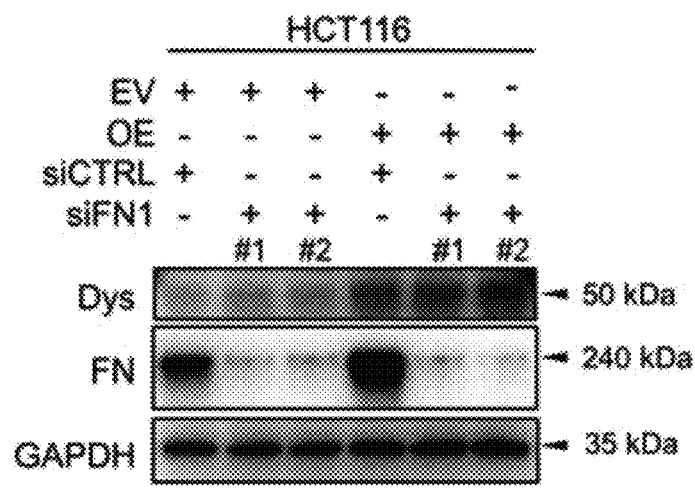
Figure 14H:
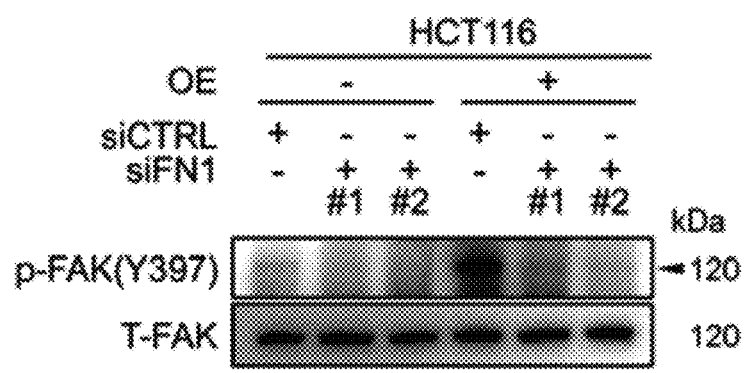
Figure 15F:
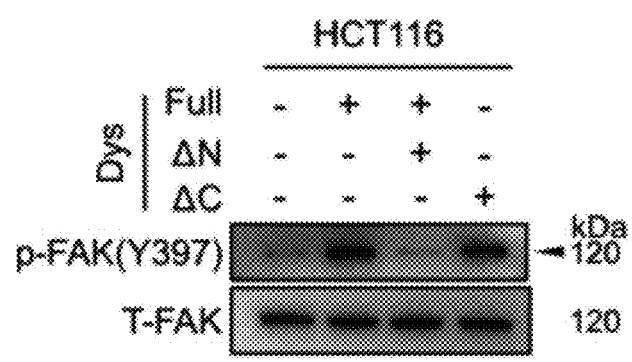

Because we observed fibronectin secretion and adhesion to CRC cell membranes during 4 days of culture in vitro (FIG. 12C), we next examined the potential effect of dysadherin on the status of endogenous FAK activation. Immunoblot analysis of CRC cells cultured for 4 days showed that the endogenous p-FAK level was attenuated or enhanced by dysadherin KO or OE, respectively (FIGS. 15E,15F). In this experiment, we repeatedly observed that the OE of the ΔN-mutant dysadherin did not increase FAK activation, indicating the indispensable role of the extracellular domain of dysadherin in FAK activation. Next, to determine whether fibronectin is involved in the dysadherin-mediated increase in FAK activation, we silenced fibronectin expression in both wild-type and dysadherin-OE HCT116 cells (FIGS. 14F,14G). The results showed that fibronectin silencing diminished the dysadherin-induced increase in p-FAK levels (FIG. 14H), suggesting that fibronectin mediates dysadherin-induced FAK activation. Collectively, these data provide evidence that the dysadherin-fibronectin interaction through the extracellular domain of dysadherin contributes to sustained activation of the fibronectin-integrin-FAK axis in CRC cells.

Figure 15G:
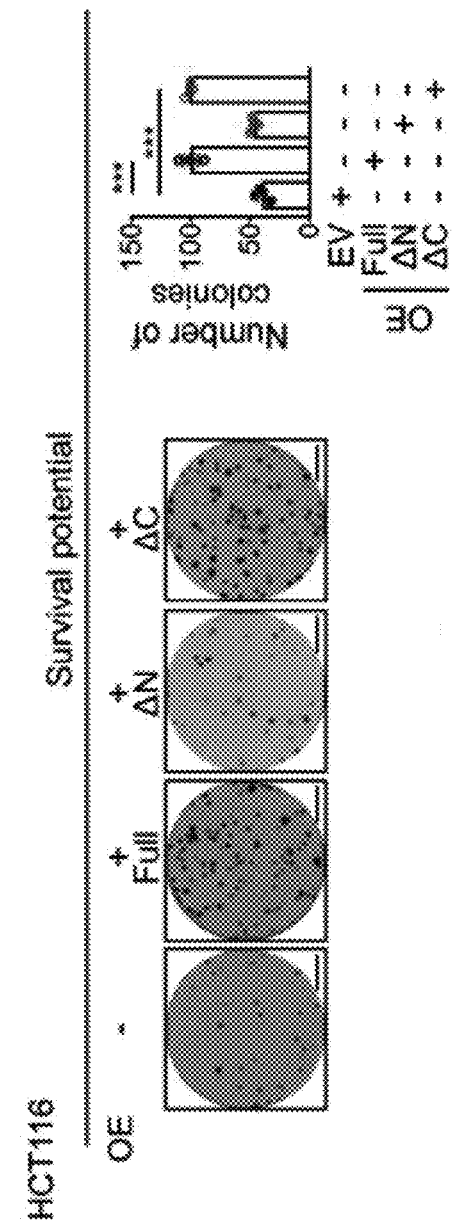
Figure 15H:
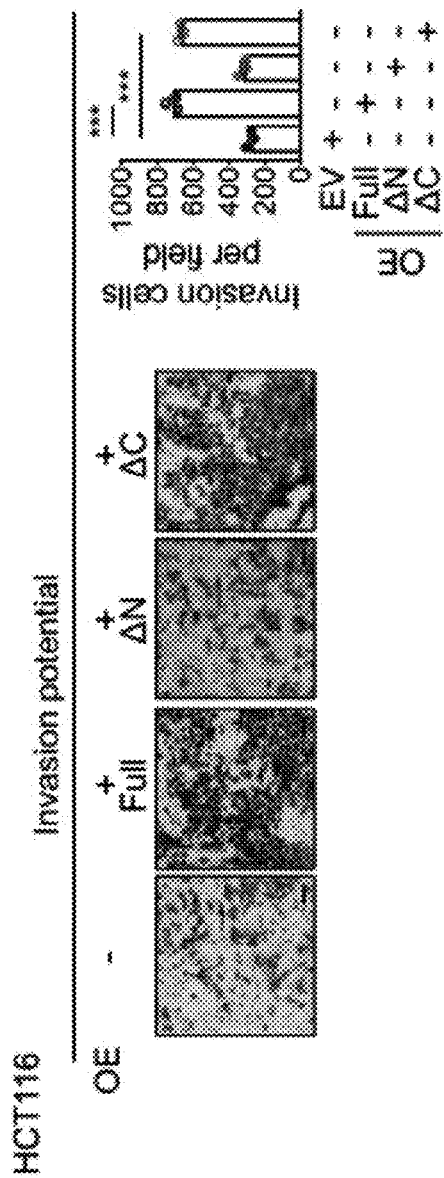
Figure 16A:
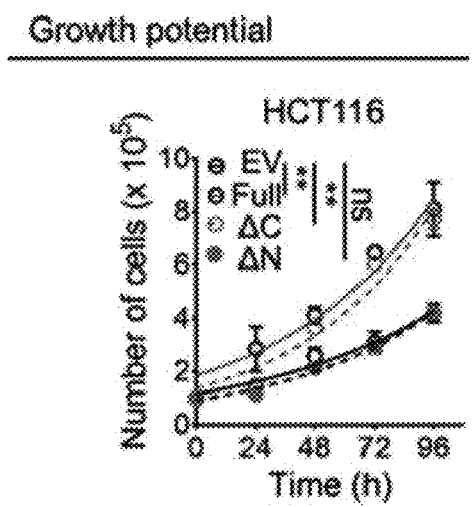
FIGS. 16A-16G illustrate functional involvement of fibronectin/integrin/FAK axis in dysadherin-mediated pro-tumor activity.
Figure 16B:
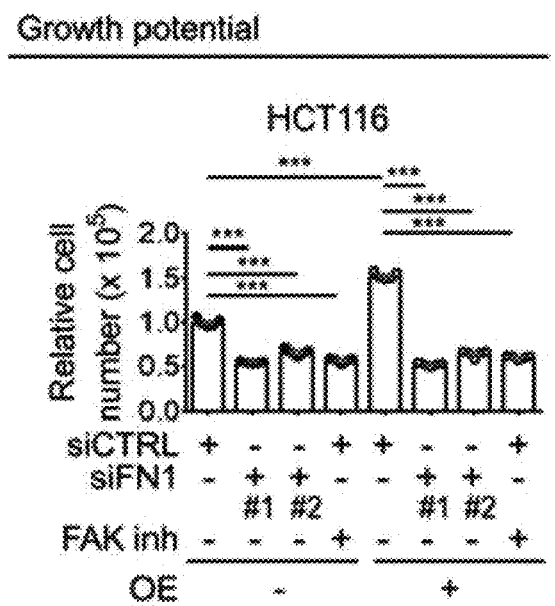
Figure 16C:
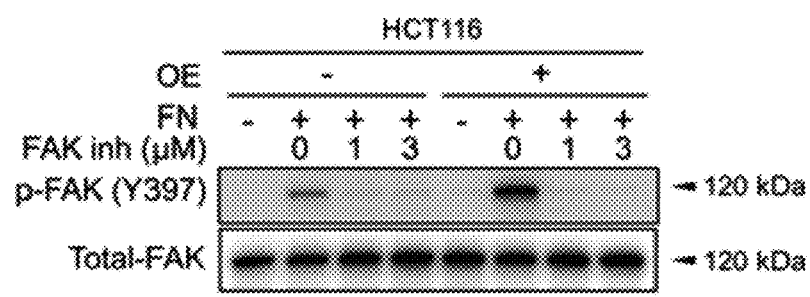
Figure 16D:
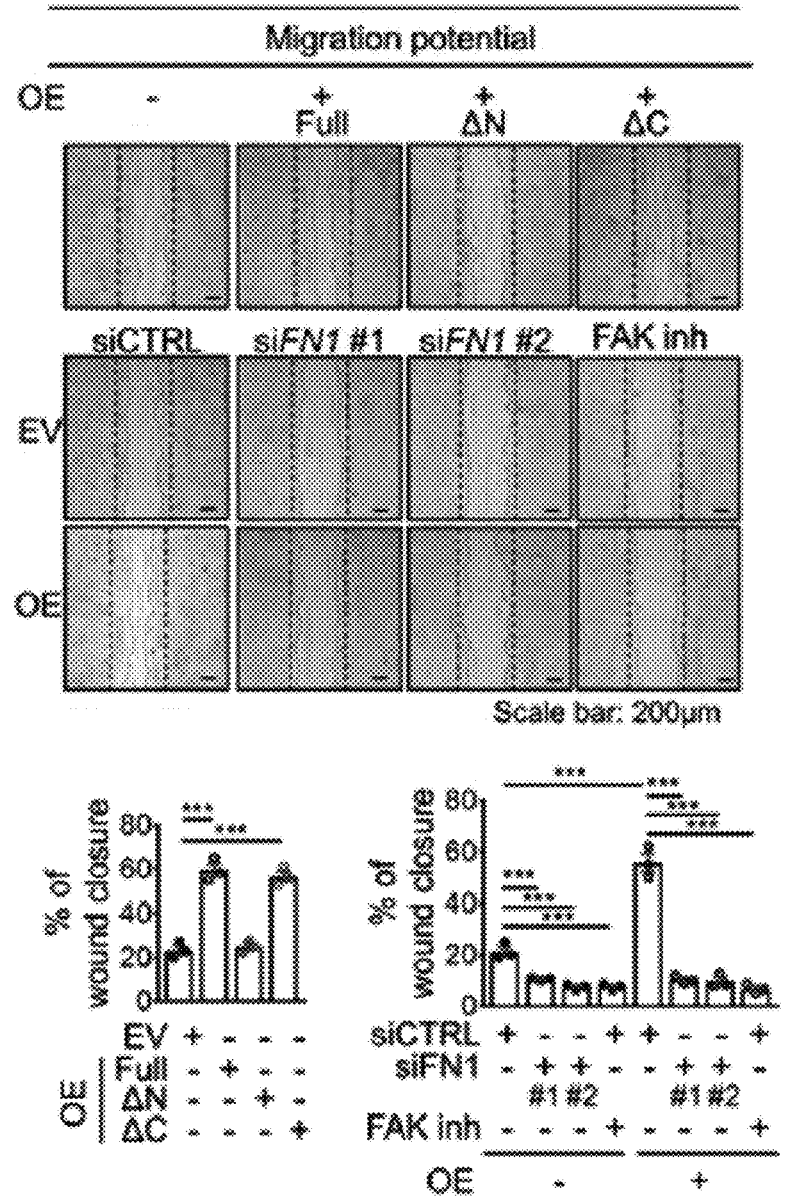
Figure 16E:
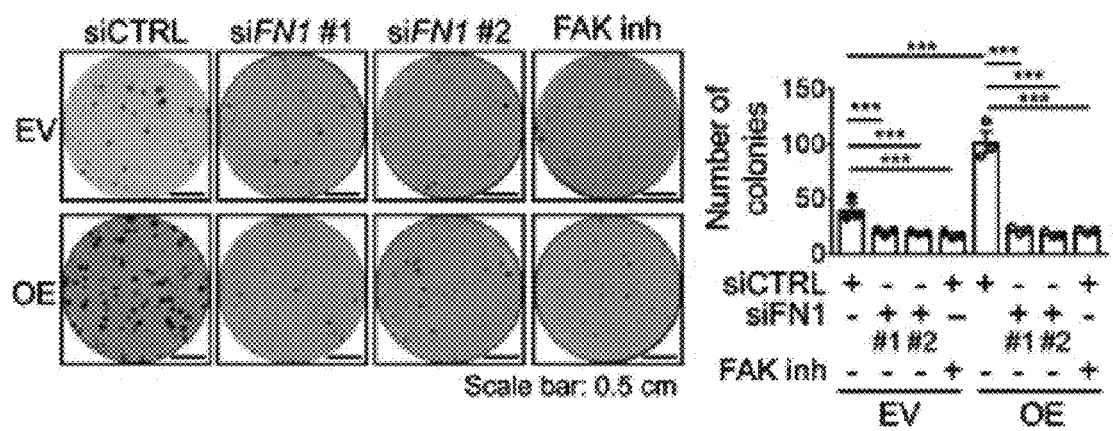
Figure 16F:
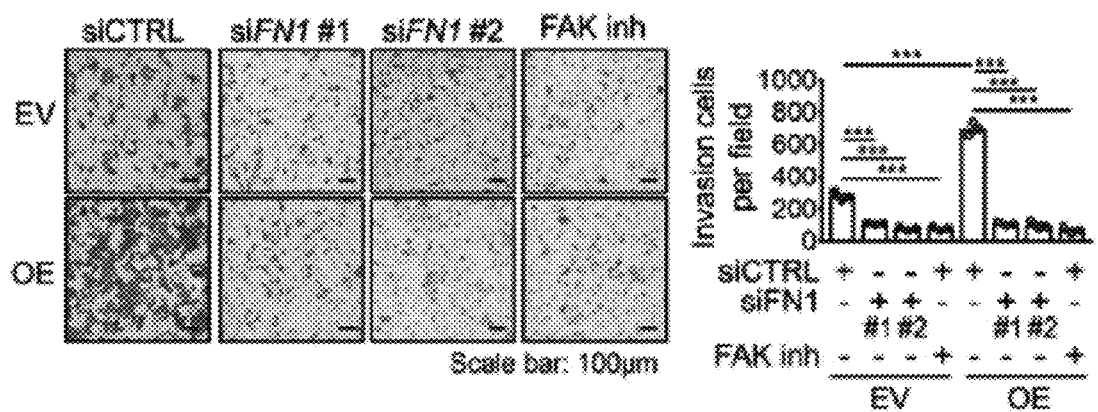
Figure 16G:
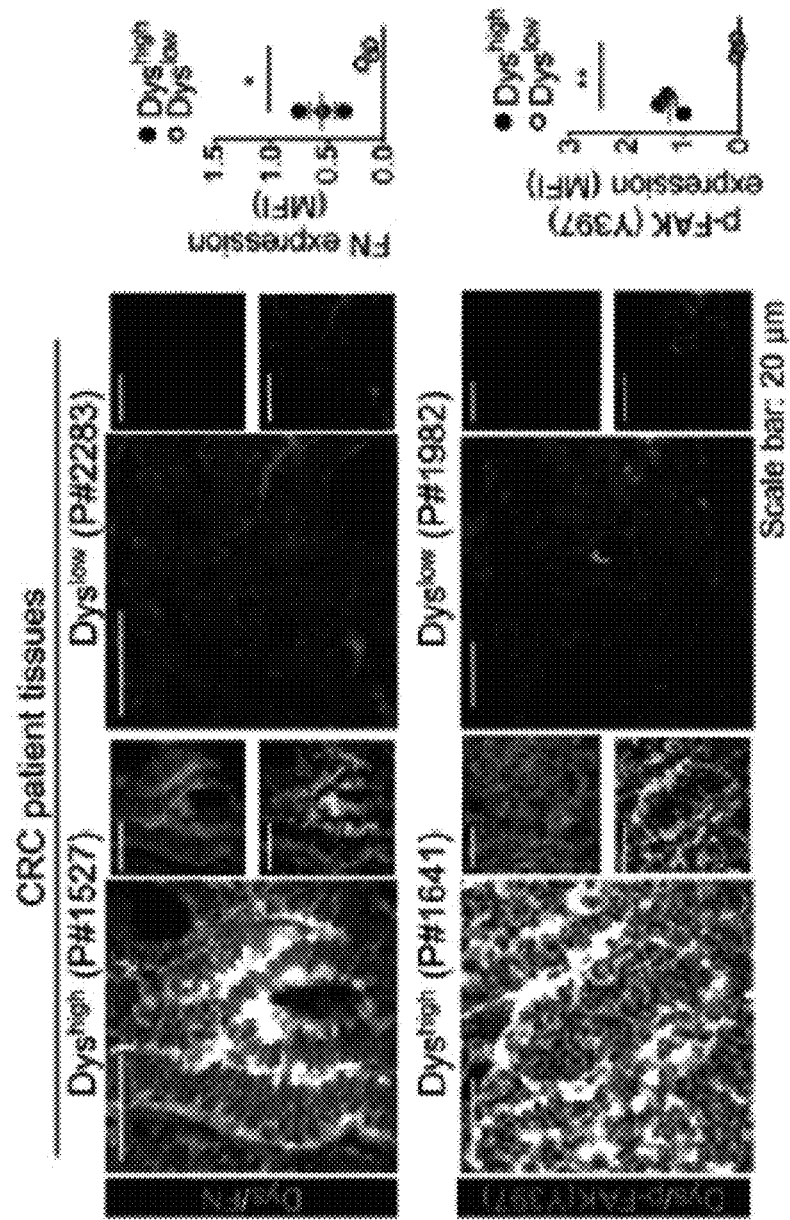

6. Inhibition of the Dysadherin-Fibronectin-FAK Axis Attenuates the Protumor Activity of Dysadherin To investigate whether dysadherin-fibronectin interaction and subsequent FAK activation are critical for dysadherin-mediated protumor activity, we disrupted the dysadherin-fibronectin-FAK axis in 3 different ways and examined the effects on diverse cellular functions: CRC growth and CRC cell survival, migration, and invasion. First, using dysadherin with the extracellular domain deleted (ΔN-mutant), we examined whether the fibronectin-binding domain is a key regulatory element that mediates the biological function of dysadherin. Second, by silencing fibronectin expression, we determined whether fibronectin binding mediates the critical step in dysadherin function. Finally, by treating cells with a FAK inhibitor, VS-4718, we examined whether the biological function of dysadherin is dependent on FAK activation. In the context of CRC growth, deletion of the fibronectin-binding domain (ΔN-mutant) abrogated the dysadherin-induced increase in tumor growth (FIG. 15A). Notably, fibronectin knockdown and FAK inhibition diminished dysadherin-induced CRC growth and also attenuated the growth of wild-type HCT116 cells (FIG. 16B). This result is consistent with the FAK activation status shown in FIGS. 14H and 16C, which show that both fibronectin knockdown and treatment with VS-4718 diminished basal p-FAK levels. Similarly, disruption of the dysadherin-fibronectin interaction by deletion of the extracellular domain of dysadherin (ΔN-mutant) abrogated the dysadherin-induced increases in CRC survival, migration, and invasion (FIGS. 15G,15H and FIG. 16D); this dysadherin-induced aggressive phenotype was attenuated by fibronectin knockdown or FAK inhibition (FIGS. 16D-16F). Collectively, these results suggest that the fibronectin-integrin-FAK pathway is a key mechanism of dysadherin-induced intestinal tumorigenesis. Consistently, IF staining of CRC tissues from patients revealed that the extent of fibronectin and p-FAK within the tumor epithelium are significantly increased in dysadherin$^{high}$ tumors compared to dysadherin$^{low}$ tumors (FIG. 16G).

Figure 17A:
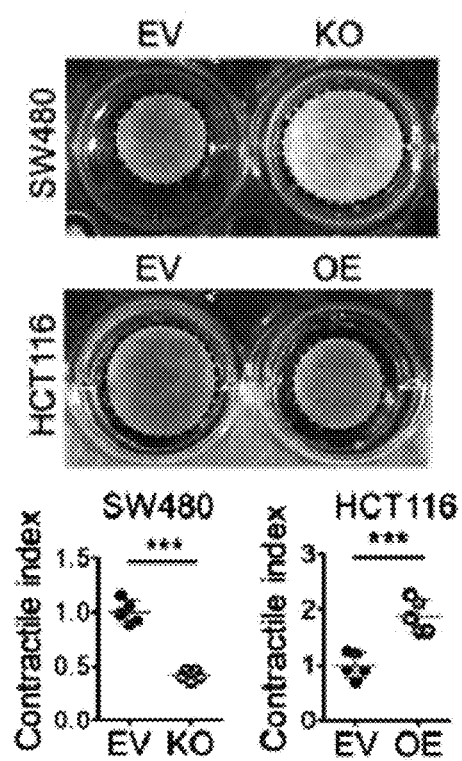
FIGS. 17A-17D illustrate dysadherin enhances mechanical force in CRC cells and facilitates YAP mechanotransduction.
Figure 17B:
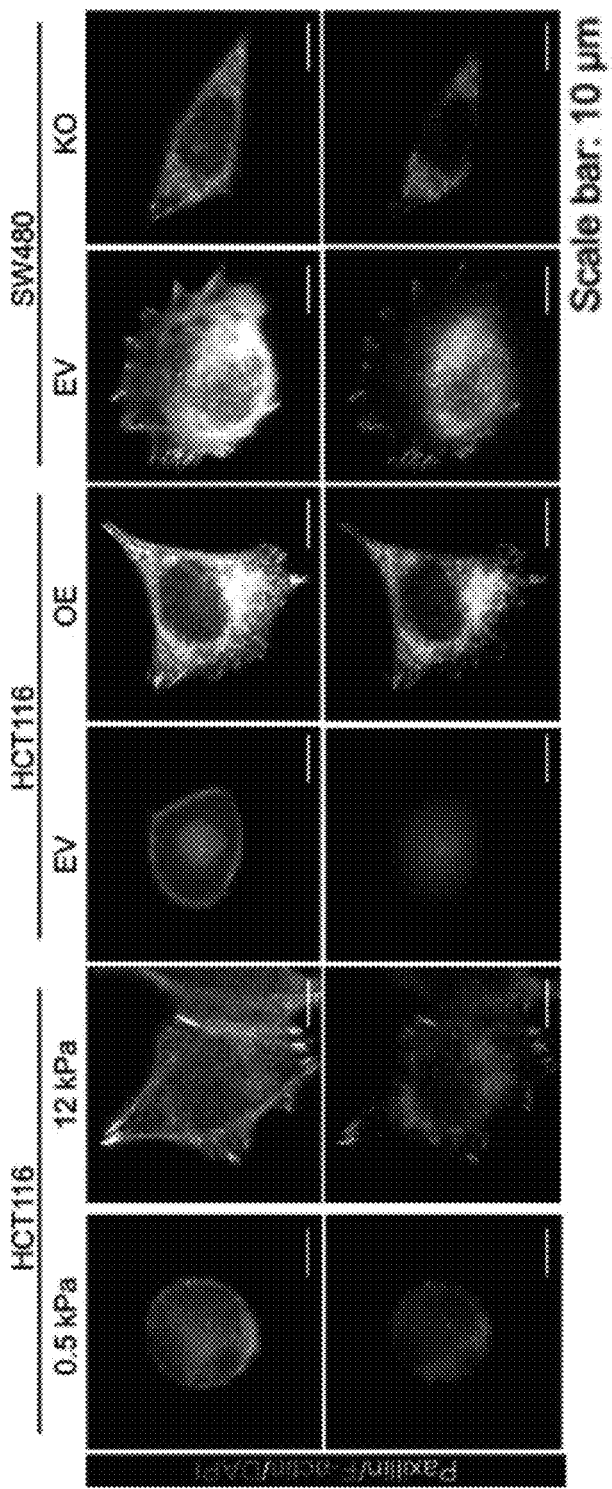
Figure 17C:
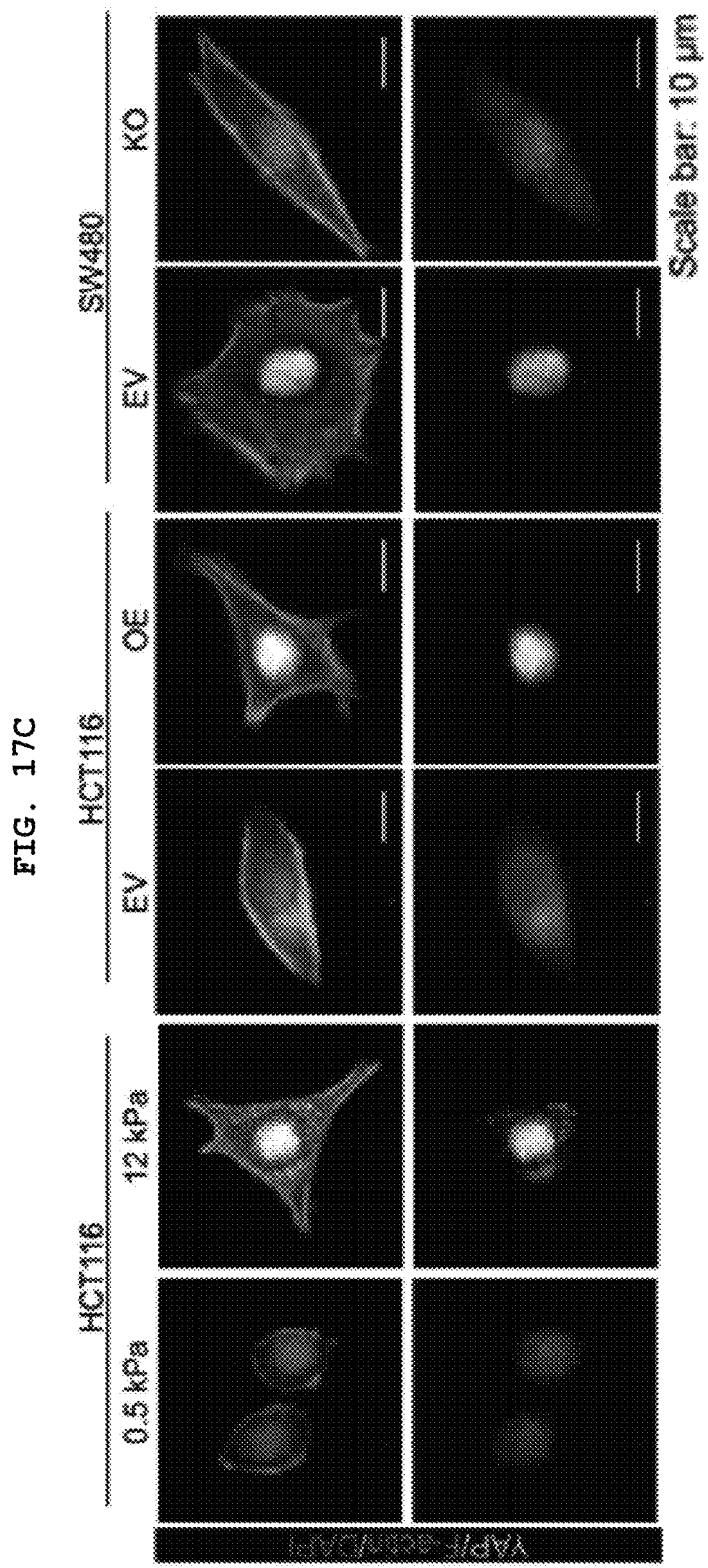
Figure 17D:
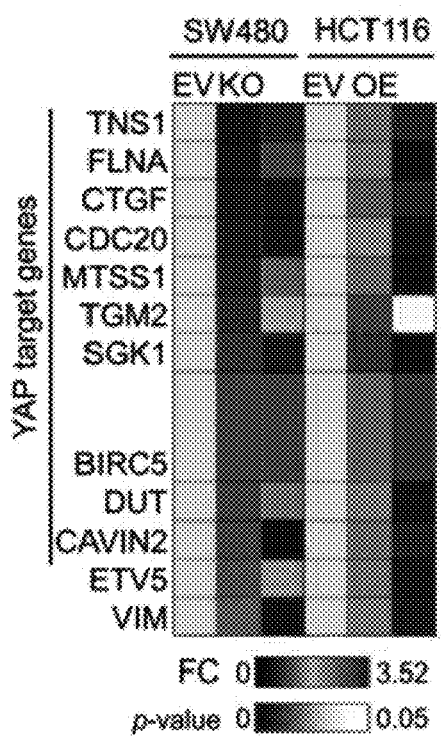
Figure 18:
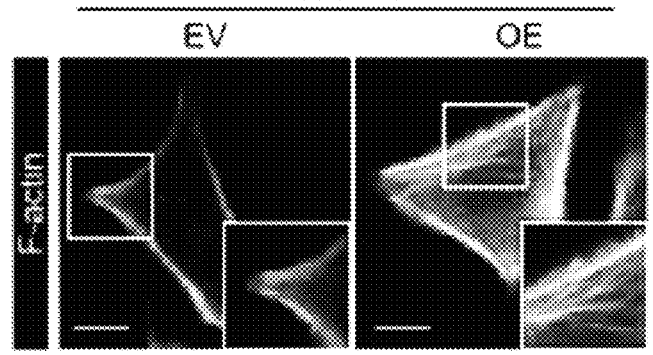
FIG. 18 illustrates effect of dysadherin on F-actin stress fibers. IF analysis of cytoskeletal tension by visualizing F-actin in CRC cells upon dysadherin OE (in HCT116 cells) or KO (in SW480 cells). CRC cells were seeded on fibronectin-coated glass slides and stained with alexa555-conjugated phalloidin.
Figure 18:
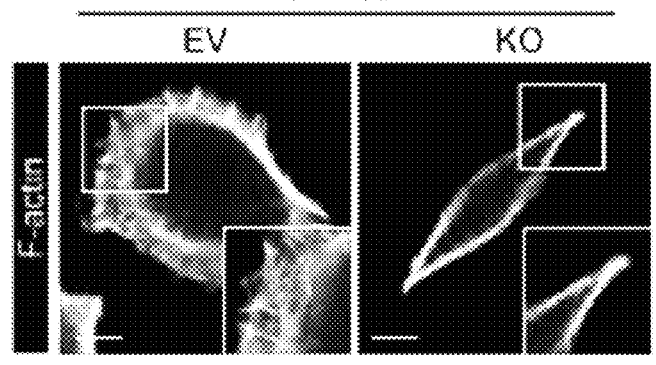
Figure 19:
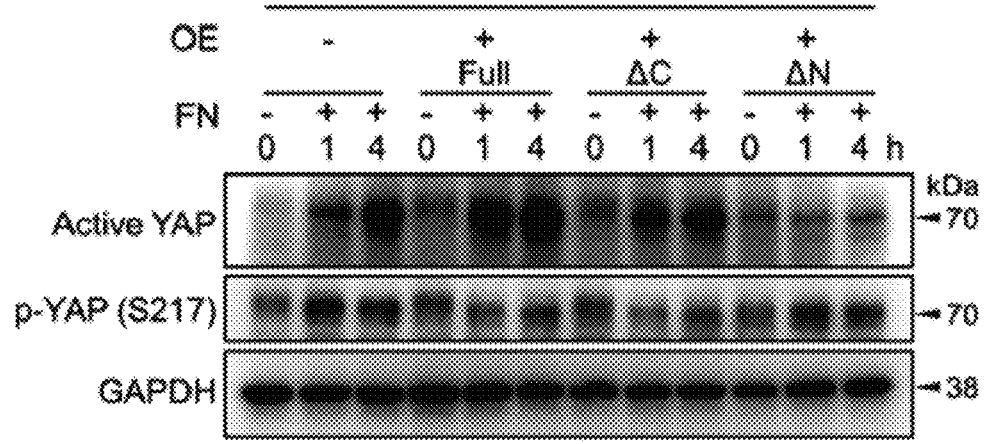
FIG. 19 illustrates potential involvement of dysadherin in YAP activation during cell adhesion to fibronectin. Immunoblot analysis was performed in HCT116 cells overexpressing (OE) wild-type (full length) or mutant dysadherin to visualize the status of YAP activation. Cells were starved for 24 h in serum-free media, then detached and reseeded onto fibronectin-coated culture plates. After the indicated times, the cells were lysed, and whole-cell extracts were subjected to immunoblot analyses to visualize YAP activation status. EV-transfected cells were used as the control group. The extent of active YAP was increased and the extent of inactive YAP (phosphorylated-YAP; p-YAP) was decreased upon cell adhesion to fibronectin, suggesting that YAP activation occurs during cell adhesion to fibronectin. Dysadherin OE enhanced fibronectin-induced YAP activation. Deletion of the extracellular domain of dysadherin (ΔN-mutant) attenuated the dysadherin-mediated increase in YAP activation, while deletion of the intracellular domain (ΔC-mutant) did not. EV: empty vector, ΔC: ΔC-mutant, ΔN: ΔN-mutant.

7. Dysadherin Transduces Mechanical Forces and Promotes YAP Signal Activation During cell adhesion, an integrin-FAK axis at focal adhesions (FAs) integrates biomechanical signals by connecting the ECM with the actin cytoskeleton to generate mechanical force in cells; this promotes reciprocal ECM remodeling. We therefore wondered whether dysadherin serves as a regulator of mechanical force. The collagen gel contraction assay has served as a classic tool in the field of mechanobiology to study cell-induced contraction of the ECM, which plays an important role in tumor progression and aggression. We analyzed the extent of gel contraction upon dysadherin OE and KO using this assay. Dysadherin OE significantly increased the gel contraction compared with the control-transfected cells, while dysadherin KO reduced the extent of gel contraction (FIG. 17A). In line with these data, we also confirmed that dysadherin expression is a positive regulator of cytoskeletal tension, indicated by an increase or decrease in F-actin stress fibers upon dysadherin OE or KO, respectively (FIG. 18). These data suggest that dysadherin generates mechanical forces in cells. To confirm whether dysadherin-driven mechanical forces activate downstream biochemical signals, we visualized signal transductions such as FA assembly and yes-associated protein 1 (YAP) activation. FA assembly was visualized by staining a FA adapter protein, paxillin. In these experiments, we used hydrogels with a defined elastic modulus as a positive control for mechanical force. Consequently, dysadherin-OE cells displayed larger cell spreading areas and greater size and number of FAs, similar to how cells grown on stiff hydrogel (12 kPa) showed greater cell spreading and FA assembly than cells grown on soft hydrogel (0.5 kPa) (FIG. 17B). Consistently, the nuclear translocation of YAP was up-regulated in cells grown on stiff hydrogel, confirming that mechanical stress enhances YAP signal activation. In line with this result, dysadherin OE significantly increased the nuclear YAP ratio during cell adhesion to fibronectin, while dysadherin KO decreased it (FIG. 17C). Moreover, validation with CRC cells confirmed that YAP target gene expression tended to increase upon dysadherin OE and decrease upon dysadherin deletion (FIG. 17D), and immunoblots confirmed that dysadherin OE facilitated activation of YAP by dephosphorylation (FIG. 19). Collectively, our data suggest that dysadherin facilitates cell adhesion to fibronectin, thus transducing mechanical forces into biochemical signals within cells.

REFERENCE TO AN ELECTRONIC SEQUENCE LISTING

A sequence listing electronically submitted on Nov. 28, 2022 as a XML file named 20221128_S03622LC91_TU_SEQ.XML, created on Nov. 23, 2022 and having a size of 102,035 bytes, is incorporated herein by reference in its entirety.

What is claimed is:

1. A method for treatment of cancer in which dysadherin is overexpressed the method comprising:
administering to a subject in need thereof a composition comprising a peptide, wherein the peptide includes a 10aa or more portion of SEQ ID NO: 1.

2. The method of claim 1, wherein the peptide is selected from the group consisting of SEQ ID NOs: 2 to 7.

3. The method of claim 1, wherein the peptide consists of sequences of SEQ ID NO: 2 or 5.

4. The method of claim 1, wherein the cancer is at least one selected from the group consisting of colorectal cancer, breast cancer, colon cancer, small intestinal cancer, rectal cancer, ovarian cancer, cervical cancer, prostate cancer, testicular cancer, penile cancer, urothelial cancer, ureteral cancer, renal pelvic cancer, esophageal cancer, laryngeal cancer, gastric cancer, gastrointestinal cancer, skin cancer, keratoacanthoma, follicular carcinoma, melanoma, lung cancer, small cell lung carcinoma, non-small cell lung carcinoma (NSCLC), lung adenocarcinoma, squamous cell carcinoma of the lung, pancreatic cancer, thyroid cancer, papillary cancer, bladder cancer, liver cancer, bile duct cancer, bone cancer, hair cell cancer, oral cancer, lip cancer, tongue cancer, salivary gland cancer, pharyngeal cancer, kidney cancer, vulvar cancer, thyroid cancer, endometrial cancer, uterine cancer, brain cancer, central nervous system cancer, peritoneal cancer, hepatocellular carcinoma, Hodgkin disease, leukemia, and a combination thereof.

5. The method of claim 1, wherein the cancer is colorectal cancer, liver cancer or breast cancer.

6. A method for treatment of colorectal cancer and/or intestinal cancer, the method comprising:
   administering to a subject in need thereof a composition comprising a peptide with SEQ ID NO: 3 and/or a peptide with SEQ ID NO: 6.

\* \* \* \* \*

```
                        SEQUENCE LISTING

Sequence total quantity: 115
SEQ ID NO: 1            moltype = AA  length = 52
FEATURE                 Location/Qualifiers
source                  1..52
                        mol_type = protein
                        organism = Homo sapiens
SEQUENCE: 1
PADETPQPQT QTQQLEGTDG PLVTDPETHK STKAAHPTDD TTTLSERPSP ST          52

SEQ ID NO: 2            moltype = AA  length = 20
FEATURE                 Location/Qualifiers
source                  1..20
                        mol_type = protein
                        organism = Homo sapiens
SEQUENCE: 2
LQPTSPTPTW PADETPQPQT                                              20

SEQ ID NO: 3            moltype = AA  length = 21
FEATURE                 Location/Qualifiers
source                  1..21
                        mol_type = protein
                        organism = Homo sapiens
SEQUENCE: 3
PADETPQPQT QTQQLEGTDG P                                            21

SEQ ID NO: 4            moltype = AA  length = 20
FEATURE                 Location/Qualifiers
source                  1..20
                        mol_type = protein
                        organism = Homo sapiens
SEQUENCE: 4
TQQLEGTDGP LVTDPETHKS                                              20

SEQ ID NO: 5            moltype = AA  length = 21
FEATURE                 Location/Qualifiers
source                  1..21
                        mol_type = protein
                        organism = Homo sapiens
SEQUENCE: 5
LVTDPETHKS TKAAHPTDDT T                                            21

SEQ ID NO: 6            moltype = AA  length = 20
FEATURE                 Location/Qualifiers
source                  1..20
                        mol_type = protein
                        organism = Homo sapiens
SEQUENCE: 6
KAAHPTDDTT TLSERPSPST                                              20

SEQ ID NO: 7            moltype = AA  length = 20
FEATURE                 Location/Qualifiers
source                  1..20
                        mol_type = protein
                        organism = Homo sapiens
SEQUENCE: 7
TLSERPSPST DVQTDPQTLK                                              20

SEQ ID NO: 8            moltype = AA  length = 11
FEATURE                 Location/Qualifiers
```

```
                            -continued source                  1..11
                        mol_type = protein
                        organism = Homo sapiens
SEQUENCE: 8
PADETPQPQT Q                                                      11

SEQ ID NO: 9            moltype = AA   length = 10
FEATURE                 Location/Qualifiers
source                  1..10
                        mol_type = protein
                        organism = Homo sapiens
SEQUENCE: 9
TQQLEGTDGP                                                        10

SEQ ID NO: 10           moltype = AA   length = 10
FEATURE                 Location/Qualifiers
source                  1..10
                        mol_type = protein
                        organism = Homo sapiens
SEQUENCE: 10
LVTDPETHKS                                                        10

SEQ ID NO: 11           moltype = AA   length = 10
FEATURE                 Location/Qualifiers
source                  1..10
                        mol_type = protein
                        organism = Homo sapiens
SEQUENCE: 11
KAAHPTDDTT                                                        10

SEQ ID NO: 12           moltype = AA   length = 10
FEATURE                 Location/Qualifiers
source                  1..10
                        mol_type = protein
                        organism = Homo sapiens
SEQUENCE: 12
TLSERPSPST                                                        10

SEQ ID NO: 13           moltype = DNA  length = 23
FEATURE                 Location/Qualifiers
source                  1..23
                        mol_type = other DNA
                        organism = synthetic construct
SEQUENCE: 13
aggctgctag gcatctcggg ggg                                         23

SEQ ID NO: 14           moltype = DNA  length = 23
FEATURE                 Location/Qualifiers
source                  1..23
                        mol_type = other DNA
                        organism = synthetic construct
SEQUENCE: 14
tcttcctggg ctcggtcacg tgg                                         23

SEQ ID NO: 15           moltype = DNA  length = 23
FEATURE                 Location/Qualifiers
source                  1..23
                        mol_type = other DNA
                        organism = synthetic construct
SEQUENCE: 15
ccccgatgag cgatacagag aca                                         23

SEQ ID NO: 16           moltype = DNA  length = 25
FEATURE                 Location/Qualifiers
source                  1..25
                        mol_type = other DNA
                        organism = synthetic construct
SEQUENCE: 16
gcagttagtt ctgttctgtg cctcg                                       25

SEQ ID NO: 17           moltype = DNA  length = 25
FEATURE                 Location/Qualifiers
source                  1..25
                        mol_type = other DNA
                        organism = synthetic construct
SEQUENCE: 17
atggtgactg aggatcaggg tcttg                                       25

SEQ ID NO: 18           moltype = DNA  length = 25
```

```
                       -continued

FEATURE                Location/Qualifiers
source                 1..25
                       mol_type = other DNA
                       organism = synthetic construct
SEQUENCE: 18
gcacacctat aacctcaagc ctcag                                           25

SEQ ID NO: 19          moltype = DNA   length = 21
FEATURE                Location/Qualifiers
source                 1..21
                       mol_type = other DNA
                       organism = synthetic construct
SEQUENCE: 19
gcctaagatg agcgcaagtt g                                               21

SEQ ID NO: 20          moltype = DNA   length = 21
FEATURE                Location/Qualifiers
source                 1..21
                       mol_type = other DNA
                       organism = synthetic construct
SEQUENCE: 20
tactaggcag atggccacag g                                               21

SEQ ID NO: 21          moltype = DNA   length = 20
FEATURE                Location/Qualifiers
source                 1..20
                       mol_type = other DNA
                       organism = synthetic construct
SEQUENCE: 21
gaaaggtacc cctgcagtct                                                 20

SEQ ID NO: 22          moltype = DNA   length = 18
FEATURE                Location/Qualifiers
source                 1..18
                       mol_type = other DNA
                       organism = synthetic construct
SEQUENCE: 22
accagcagtc cccgtttc                                                   18

SEQ ID NO: 23          moltype = DNA   length = 20
FEATURE                Location/Qualifiers
source                 1..20
                       mol_type = other DNA
                       organism = synthetic construct
SEQUENCE: 23
tcccactgat gacaccacga                                                 20

SEQ ID NO: 24          moltype = DNA   length = 19
FEATURE                Location/Qualifiers
source                 1..19
                       mol_type = other DNA
                       organism = synthetic construct
SEQUENCE: 24
aaaccagatg gcttgaggg                                                  19

SEQ ID NO: 25          moltype = DNA   length = 20
FEATURE                Location/Qualifiers
source                 1..20
                       mol_type = other DNA
                       organism = synthetic construct
SEQUENCE: 25
gtcgcagctg tgctgttcat                                                 20

SEQ ID NO: 26          moltype = DNA   length = 22
FEATURE                Location/Qualifiers
source                 1..22
                       mol_type = other DNA
                       organism = synthetic construct
SEQUENCE: 26
ctgcaatgat tccggcataa cc                                              22

SEQ ID NO: 27          moltype = DNA   length = 19
FEATURE                Location/Qualifiers
source                 1..19
                       mol_type = other DNA
                       organism = synthetic construct
SEQUENCE: 27
agacaggggt acctgtggg                                                  19
```

```
SEQ ID NO: 28          moltype = DNA   length = 20
FEATURE                Location/Qualifiers
source                 1..20
                       mol_type = other DNA
                       organism = synthetic construct
SEQUENCE: 28
cacatggggg tgttgctctc                                                    20

SEQ ID NO: 29          moltype = DNA   length = 20
FEATURE                Location/Qualifiers
source                 1..20
                       mol_type = other DNA
                       organism = synthetic construct
SEQUENCE: 29
aaggatggca agtacggctt                                                    20

SEQ ID NO: 30          moltype = DNA   length = 20
FEATURE                Location/Qualifiers
source                 1..20
                       mol_type = other DNA
                       organism = synthetic construct
SEQUENCE: 30
aaacttgcag ggctgtcctt                                                    20

SEQ ID NO: 31          moltype = DNA   length = 20
FEATURE                Location/Qualifiers
source                 1..20
                       mol_type = other DNA
                       organism = synthetic construct
SEQUENCE: 31
aatgccttcc ttgcggtgaa                                                    20

SEQ ID NO: 32          moltype = DNA   length = 20
FEATURE                Location/Qualifiers
source                 1..20
                       mol_type = other DNA
                       organism = synthetic construct
SEQUENCE: 32
tctcacaggc ctcactcgta                                                    20

SEQ ID NO: 33          moltype = DNA   length = 20
FEATURE                Location/Qualifiers
source                 1..20
                       mol_type = other DNA
                       organism = synthetic construct
SEQUENCE: 33
tcaagacagc acgtggacct                                                    20

SEQ ID NO: 34          moltype = DNA   length = 20
FEATURE                Location/Qualifiers
source                 1..20
                       mol_type = other DNA
                       organism = synthetic construct
SEQUENCE: 34
cgggcaatgt aggcaaagca                                                    20

SEQ ID NO: 35          moltype = DNA   length = 20
FEATURE                Location/Qualifiers
source                 1..20
                       mol_type = other DNA
                       organism = synthetic construct
SEQUENCE: 35
gtcgaaatct ctggggcctg                                                    20

SEQ ID NO: 36          moltype = DNA   length = 20
FEATURE                Location/Qualifiers
source                 1..20
                       mol_type = other DNA
                       organism = synthetic construct
SEQUENCE: 36
atgttgtggt ggtgccactt                                                    20

SEQ ID NO: 37          moltype = DNA   length = 22
FEATURE                Location/Qualifiers
source                 1..22
                       mol_type = other DNA
                       organism = synthetic construct
SEQUENCE: 37
caggcaggtt ctcttcctct ca                                                 22
```

```
SEQ ID NO: 38            moltype = DNA   length = 22
FEATURE                  Location/Qualifiers
source                   1..22
                         mol_type = other DNA
                         organism = synthetic construct
SEQUENCE: 38
aggagaagag gctgaggaac aa                                                22

SEQ ID NO: 39            moltype = DNA   length = 20
FEATURE                  Location/Qualifiers
source                   1..20
                         mol_type = other DNA
                         organism = synthetic construct
SEQUENCE: 39
cagactacga ggcgtcatcc                                                   20

SEQ ID NO: 40            moltype = DNA   length = 20
FEATURE                  Location/Qualifiers
source                   1..20
                         mol_type = other DNA
                         organism = synthetic construct
SEQUENCE: 40
cgtgggaatg aagttggcac                                                   20

SEQ ID NO: 41            moltype = DNA   length = 18
FEATURE                  Location/Qualifiers
source                   1..18
                         mol_type = other DNA
                         organism = synthetic construct
SEQUENCE: 41
acgcccgata cgctgagt                                                     18

SEQ ID NO: 42            moltype = DNA   length = 23
FEATURE                  Location/Qualifiers
source                   1..23
                         mol_type = other DNA
                         organism = synthetic construct
SEQUENCE: 42
tcacgcagat cttgctgaac ata                                               23

SEQ ID NO: 43            moltype = DNA   length = 20
FEATURE                  Location/Qualifiers
source                   1..20
                         mol_type = other DNA
                         organism = synthetic construct
SEQUENCE: 43
atcagctaca ccaccaacgc                                                   20

SEQ ID NO: 44            moltype = DNA   length = 20
FEATURE                  Location/Qualifiers
source                   1..20
                         mol_type = other DNA
                         organism = synthetic construct
SEQUENCE: 44
acgtccgtct gtggatagga                                                   20

SEQ ID NO: 45            moltype = DNA   length = 22
FEATURE                  Location/Qualifiers
source                   1..22
                         mol_type = other DNA
                         organism = synthetic construct
SEQUENCE: 45
ccttggactg tcaggaatga gg                                                22

SEQ ID NO: 46            moltype = DNA   length = 22
FEATURE                  Location/Qualifiers
source                   1..22
                         mol_type = other DNA
                         organism = synthetic construct
SEQUENCE: 46
ttctccgtgt ccatccactg gt                                                22

SEQ ID NO: 47            moltype = DNA   length = 20
FEATURE                  Location/Qualifiers
source                   1..20
                         mol_type = other DNA
                         organism = synthetic construct
SEQUENCE: 47
```

```
cgcatcagtg gacacattgc                                               20

SEQ ID NO: 48            moltype = DNA   length = 20
FEATURE                  Location/Qualifiers
source                   1..20
                         mol_type = other DNA
                         organism = synthetic construct
SEQUENCE: 48
cctcactgct tgtccctacc                                               20

SEQ ID NO: 49            moltype = DNA   length = 20
FEATURE                  Location/Qualifiers
source                   1..20
                         mol_type = other DNA
                         organism = synthetic construct
SEQUENCE: 49
catcccaccc tctcacagtt                                               20

SEQ ID NO: 50            moltype = DNA   length = 20
FEATURE                  Location/Qualifiers
source                   1..20
                         mol_type = other DNA
                         organism = synthetic construct
SEQUENCE: 50
gtctctgcct tgacccaaag                                               20

SEQ ID NO: 51            moltype = DNA   length = 20
FEATURE                  Location/Qualifiers
source                   1..20
                         mol_type = other DNA
                         organism = synthetic construct
SEQUENCE: 51
actttgtcac cgagacacca                                               20

SEQ ID NO: 52            moltype = DNA   length = 19
FEATURE                  Location/Qualifiers
source                   1..19
                         mol_type = other DNA
                         organism = synthetic construct
SEQUENCE: 52
cagcagagca ggtgaggtg                                                19

SEQ ID NO: 53            moltype = DNA   length = 20
FEATURE                  Location/Qualifiers
source                   1..20
                         mol_type = other DNA
                         organism = synthetic construct
SEQUENCE: 53
tgcacatccc caactgtgac                                               20

SEQ ID NO: 54            moltype = DNA   length = 22
FEATURE                  Location/Qualifiers
source                   1..22
                         mol_type = other DNA
                         organism = synthetic construct
SEQUENCE: 54
tgtagaagag atgacactcg gg                                            22

SEQ ID NO: 55            moltype = DNA   length = 23
FEATURE                  Location/Qualifiers
source                   1..23
                         mol_type = other DNA
                         organism = synthetic construct
SEQUENCE: 55
tgataaactc tctgcttctc cct                                           23

SEQ ID NO: 56            moltype = DNA   length = 18
FEATURE                  Location/Qualifiers
source                   1..18
                         mol_type = other DNA
                         organism = synthetic construct
SEQUENCE: 56
gttgcgtcag tcccgtgt                                                 18

SEQ ID NO: 57            moltype = DNA   length = 21
FEATURE                  Location/Qualifiers
source                   1..21
                         mol_type = other DNA
                         organism = synthetic construct
```

-continued

```
SEQUENCE: 57
accacgacga ctcatacaca g                                              21

SEQ ID NO: 58          moltype = DNA   length = 20
FEATURE                Location/Qualifiers
source                 1..20
                       mol_type = other DNA
                       organism = synthetic construct
SEQUENCE: 58
cgagccctga ccagaaaagt                                                20

SEQ ID NO: 59          moltype = DNA   length = 20
FEATURE                Location/Qualifiers
source                 1..20
                       mol_type = other DNA
                       organism = synthetic construct
SEQUENCE: 59
agcaagcccg gttgttatga                                                20

SEQ ID NO: 60          moltype = DNA   length = 20
FEATURE                Location/Qualifiers
source                 1..20
                       mol_type = other DNA
                       organism = synthetic construct
SEQUENCE: 60
cccactcggt aagtgttccc                                                20

SEQ ID NO: 61          moltype = DNA   length = 19
FEATURE                Location/Qualifiers
source                 1..19
                       mol_type = other DNA
                       organism = synthetic construct
SEQUENCE: 61
tgccatcgcc aaggagtag                                                 19

SEQ ID NO: 62          moltype = DNA   length = 20
FEATURE                Location/Qualifiers
source                 1..20
                       mol_type = other DNA
                       organism = synthetic construct
SEQUENCE: 62
tgcacagacg gtcactcaaa                                                20

SEQ ID NO: 63          moltype = DNA   length = 24
FEATURE                Location/Qualifiers
source                 1..24
                       mol_type = other DNA
                       organism = synthetic construct
SEQUENCE: 63
cggaatgttc tgttgaagaa tgtg                                           24

SEQ ID NO: 64          moltype = DNA   length = 24
FEATURE                Location/Qualifiers
source                 1..24
                       mol_type = other DNA
                       organism = synthetic construct
SEQUENCE: 64
tgtcagcagt ctggaaagag aagt                                           24

SEQ ID NO: 65          moltype = DNA   length = 21
FEATURE                Location/Qualifiers
source                 1..21
                       mol_type = other DNA
                       organism = synthetic construct
SEQUENCE: 65
agcccttct caaggaccac c                                               21

SEQ ID NO: 66          moltype = DNA   length = 23
FEATURE                Location/Qualifiers
source                 1..23
                       mol_type = other DNA
                       organism = synthetic construct
SEQUENCE: 66
ttgaagcaga agaaacactg ggc                                            23

SEQ ID NO: 67          moltype = DNA   length = 22
FEATURE                Location/Qualifiers
source                 1..22
                       mol_type = other DNA
```

```
                                     -continued
                       organism = synthetic construct
SEQUENCE: 67
cagtcaactt caagaggctt gg                                              22

SEQ ID NO: 68          moltype = DNA  length = 21
FEATURE                Location/Qualifiers
source                 1..21
                       mol_type = other DNA
                       organism = synthetic construct
SEQUENCE: 68
tgctcatggc tacaagacga c                                               21

SEQ ID NO: 69          moltype = DNA  length = 20
FEATURE                Location/Qualifiers
source                 1..20
                       mol_type = other DNA
                       organism = synthetic construct
SEQUENCE: 69
accatcatca gcgacatgaa                                                 20

SEQ ID NO: 70          moltype = DNA  length = 20
FEATURE                Location/Qualifiers
source                 1..20
                       mol_type = other DNA
                       organism = synthetic construct
SEQUENCE: 70
cacatcctgg tgagagcaga                                                 20

SEQ ID NO: 71          moltype = DNA  length = 20
FEATURE                Location/Qualifiers
source                 1..20
                       mol_type = other DNA
                       organism = synthetic construct
SEQUENCE: 71
acccgcacca acgagaaggt                                                 20

SEQ ID NO: 72          moltype = DNA  length = 21
FEATURE                Location/Qualifiers
source                 1..21
                       mol_type = other DNA
                       organism = synthetic construct
SEQUENCE: 72
attctgctgc tccaggaagc g                                               21

SEQ ID NO: 73          moltype = DNA  length = 18
FEATURE                Location/Qualifiers
source                 1..18
                       mol_type = other DNA
                       organism = synthetic construct
SEQUENCE: 73
aagatggcgg actgtggc                                                   18

SEQ ID NO: 74          moltype = DNA  length = 17
FEATURE                Location/Qualifiers
source                 1..17
                       mol_type = other DNA
                       organism = synthetic construct
SEQUENCE: 74
tcaggcgggt catgcta                                                    17

SEQ ID NO: 75          moltype = DNA  length = 24
FEATURE                Location/Qualifiers
source                 1..24
                       mol_type = other DNA
                       organism = synthetic construct
SEQUENCE: 75
tcaagtggaa gaacttgttt gctt                                            24

SEQ ID NO: 76          moltype = DNA  length = 23
FEATURE                Location/Qualifiers
source                 1..23
                       mol_type = other DNA
                       organism = synthetic construct
SEQUENCE: 76
cacgacaata tagtggaggc aca                                             23

SEQ ID NO: 77          moltype = DNA  length = 20
FEATURE                Location/Qualifiers
source                 1..20
```

```
                            mol_type = other DNA
                            organism = synthetic construct
SEQUENCE: 77
gcccaccaag aaggaacatc                                                   20

SEQ ID NO: 78               moltype = DNA  length = 20
FEATURE                     Location/Qualifiers
source                      1..20
                            mol_type = other DNA
                            organism = synthetic construct
SEQUENCE: 78
ttttccactg agccgaagga                                                   20

SEQ ID NO: 79               moltype = DNA  length = 19
FEATURE                     Location/Qualifiers
source                      1..19
                            mol_type = other DNA
                            organism = synthetic construct
SEQUENCE: 79
gtctcctcgc tcgccttct                                                    19

SEQ ID NO: 80               moltype = DNA  length = 19
FEATURE                     Location/Qualifiers
source                      1..19
                            mol_type = other DNA
                            organism = synthetic construct
SEQUENCE: 80
ggtgaaatgg cgggtgtct                                                    19

SEQ ID NO: 81               moltype = DNA  length = 22
FEATURE                     Location/Qualifiers
source                      1..22
                            mol_type = other DNA
                            organism = synthetic construct
SEQUENCE: 81
agaagagcga agggacgtac tg                                                22

SEQ ID NO: 82               moltype = DNA  length = 22
FEATURE                     Location/Qualifiers
source                      1..22
                            mol_type = other DNA
                            organism = synthetic construct
SEQUENCE: 82
agtctaccac gtcggcattg ac                                                22

SEQ ID NO: 83               moltype = DNA  length = 19
FEATURE                     Location/Qualifiers
source                      1..19
                            mol_type = other DNA
                            organism = synthetic construct
SEQUENCE: 83
ccaatgacaa cgcctcctg                                                    19

SEQ ID NO: 84               moltype = DNA  length = 19
FEATURE                     Location/Qualifiers
source                      1..19
                            mol_type = other DNA
                            organism = synthetic construct
SEQUENCE: 84
tggtgcagcc agaaagctc                                                    19

SEQ ID NO: 85               moltype = DNA  length = 20
FEATURE                     Location/Qualifiers
source                      1..20
                            mol_type = other DNA
                            organism = synthetic construct
SEQUENCE: 85
aagagcgcat ggataggcag                                                   20

SEQ ID NO: 86               moltype = DNA  length = 20
FEATURE                     Location/Qualifiers
source                      1..20
                            mol_type = other DNA
                            organism = synthetic construct
SEQUENCE: 86
aagagcgcat ggataggcag                                                   20

SEQ ID NO: 87               moltype = DNA  length = 20
FEATURE                     Location/Qualifiers
```

```
source                        1..20
                              mol_type = other DNA
                              organism = synthetic construct
SEQUENCE: 87
catcaagtac ggtggtgacg                                                    20

SEQ ID NO: 88                 moltype = DNA  length = 20
FEATURE                       Location/Qualifiers
source                        1..20
                              mol_type = other DNA
                              organism = synthetic construct
SEQUENCE: 88
acatccacct ctgagccatc                                                    20

SEQ ID NO: 89                 moltype = RNA  length = 19
FEATURE                       Location/Qualifiers
source                        1..19
                              mol_type = other RNA
                              organism = synthetic construct
SEQUENCE: 89
ctcactagtg ggaagtgta                                                     19

SEQ ID NO: 90                 moltype = RNA  length = 19
FEATURE                       Location/Qualifiers
source                        1..19
                              mol_type = other RNA
                              organism = synthetic construct
SEQUENCE: 90
tacacttccc actagtgag                                                     19

SEQ ID NO: 91                 moltype = RNA  length = 18
FEATURE                       Location/Qualifiers
source                        1..18
                              mol_type = other RNA
                              organism = synthetic construct
SEQUENCE: 91
cacatggtct ctctccat                                                      18

SEQ ID NO: 92                 moltype = RNA  length = 19
FEATURE                       Location/Qualifiers
source                        1..19
                              mol_type = other RNA
                              organism = synthetic construct
SEQUENCE: 92
atggaagaga gaccatgtg                                                     19

SEQ ID NO: 93                 moltype = RNA  length = 19
FEATURE                       Location/Qualifiers
source                        1..19
                              mol_type = other RNA
                              organism = synthetic construct
SEQUENCE: 93
ctggattcga atgagaaca                                                     19

SEQ ID NO: 94                 moltype = RNA  length = 19
FEATURE                       Location/Qualifiers
source                        1..19
                              mol_type = other RNA
                              organism = synthetic construct
SEQUENCE: 94
tgttctcatt cgaatccag                                                     19

SEQ ID NO: 95                 moltype = RNA  length = 18
FEATURE                       Location/Qualifiers
source                        1..18
                              mol_type = other RNA
                              organism = synthetic construct
SEQUENCE: 95
ctccatgatc tgggactg                                                      18

SEQ ID NO: 96                 moltype = RNA  length = 18
FEATURE                       Location/Qualifiers
source                        1..18
                              mol_type = other RNA
                              organism = synthetic construct
SEQUENCE: 96
acagtcccag atcatgga                                                      18

SEQ ID NO: 97                 moltype = RNA  length = 19
```

-continued

| FEATURE | Location/Qualifiers | |
|---|---|---|
| source | 1..19 mol_type = other RNA organism = synthetic construct | |
| SEQUENCE: 97 | | |
| cagacttacg gtggcaact | | 19 |
| | | |
| SEQ ID NO: 98 | moltype = RNA length = 18 | |
| FEATURE | Location/Qualifiers | |
| source | 1..18 mol_type = other RNA organism = synthetic construct | |
| SEQUENCE: 98 | | |
| agttgccacc gtaagtct | | 18 |
| | | |
| SEQ ID NO: 99 | moltype = DNA length = 20 | |
| FEATURE | Location/Qualifiers | |
| source | 1..20 mol_type = other DNA organism = synthetic construct | |
| SEQUENCE: 99 | | |
| gagatgggtc ttacctctgg | | 20 |
| | | |
| SEQ ID NO: 100 | moltype = AA length = 27 | |
| FEATURE | Location/Qualifiers | |
| source | 1..27 mol_type = protein organism = synthetic construct | |
| SEQUENCE: 100 | | |
| HHHHHHQTLK DTTSSSSADS TIMDIQV | | 27 |
| | | |
| SEQ ID NO: 101 | moltype = AA length = 25 | |
| FEATURE | Location/Qualifiers | |
| source | 1..25 mol_type = protein organism = synthetic construct | |
| SEQUENCE: 101 | | |
| HHHHHHADST IMDIQVPTRA PDVYT | | 25 |
| | | |
| SEQ ID NO: 102 | moltype = AA length = 27 | |
| FEATURE | Location/Qualifiers | |
| source | 1..27 mol_type = protein organism = synthetic construct | |
| SEQUENCE: 102 | | |
| HHHHHHPTRA PDAVYTELQP TSPTPTW | | 27 |
| | | |
| SEQ ID NO: 103 | moltype = AA length = 26 | |
| FEATURE | Location/Qualifiers | |
| source | 1..26 mol_type = protein organism = synthetic construct | |
| SEQUENCE: 103 | | |
| HHHHHHLQPT SPTPTWPADE TPQPQT | | 26 |
| | | |
| SEQ ID NO: 104 | moltype = AA length = 27 | |
| FEATURE | Location/Qualifiers | |
| source | 1..27 mol_type = protein organism = synthetic construct | |
| SEQUENCE: 104 | | |
| HHHHHHPADE TPQPQTQTQQ LEGTDGP | | 27 |
| | | |
| SEQ ID NO: 105 | moltype = AA length = 26 | |
| FEATURE | Location/Qualifiers | |
| source | 1..26 mol_type = protein organism = synthetic construct | |
| SEQUENCE: 105 | | |
| HHHHHHTQQL EGTDGPLVTD PETHKS | | 26 |
| | | |
| SEQ ID NO: 106 | moltype = AA length = 27 | |
| FEATURE | Location/Qualifiers | |
| source | 1..27 mol_type = protein organism = synthetic construct | |
| SEQUENCE: 106 | | |
| HHHHHHLVTD PETHKSTKAA HPTDDTT | | 27 |

```
SEQ ID NO: 107            moltype = AA   length = 26
FEATURE                   Location/Qualifiers
source                    1..26
                          mol_type = protein
                          organism = synthetic construct
SEQUENCE: 107
HHHHHHKAAH PTDDTTTLSE RPSPST                                        26

SEQ ID NO: 108            moltype = AA   length = 26
FEATURE                   Location/Qualifiers
source                    1..26
                          mol_type = protein
                          organism = synthetic construct
SEQUENCE: 108
HHHHHHTLSE RPSPSTDVQT DPQTLK                                        26

SEQ ID NO: 109            moltype = AA   length = 26
FEATURE                   Location/Qualifiers
source                    1..26
                          mol_type = protein
                          organism = synthetic construct
SEQUENCE: 109
HHHHHHDVQT DPQTLKPSGF HEDDPF                                        26

SEQ ID NO: 110            moltype = AA   length = 26
FEATURE                   Location/Qualifiers
source                    1..26
                          mol_type = protein
                          organism = synthetic construct
SEQUENCE: 110
HHHHHHPSGF HEDDPFFYDE HTLRKR                                        26

SEQ ID NO: 111            moltype = DNA   length = 34
FEATURE                   Location/Qualifiers
source                    1..34
                          mol_type = genomic DNA
                          organism = Mus musculus
SEQUENCE: 111
ggctgcaaag gctgctaggc atctcggggg gggg                               34

SEQ ID NO: 112            moltype = DNA   length = 60
FEATURE                   Location/Qualifiers
source                    1..60
                          mol_type = genomic DNA
                          organism = Mus musculus
SEQUENCE: 112
tttcttcctg ggctcggtca cgtggtagtg ccccgatgag cgatacagag acacacagga   60

SEQ ID NO: 113            moltype = DNA   length = 25
FEATURE                   Location/Qualifiers
source                    1..25
                          mol_type = other DNA
                          organism = synthetic construct
SEQUENCE: 113
ggctgcaaag gctgctaggc atctc                                         25

SEQ ID NO: 114            moltype = DNA   length = 24
FEATURE                   Location/Qualifiers
source                    1..24
                          mol_type = other DNA
                          organism = synthetic construct
SEQUENCE: 114
tgagcgatac agagacacac agga                                          24

SEQ ID NO: 115            moltype = DNA   length = 30
FEATURE                   Location/Qualifiers
source                    1..30
                          mol_type = other DNA
                          organism = synthetic construct
SEQUENCE: 115
ccccgatgag cgatacagag acacacagga                                    30
```